US012649791B2

(12) United States Patent
Baliga et al.

(10) Patent No.: US 12,649,791 B2
(45) Date of Patent: Jun. 9, 2026

(54) IgM Fc AND J-CHAIN MUTATIONS THAT AFFECT IgM SERUM HALF-LIFE

(71) Applicant: IGM Biosciences, Inc., Mountain View, CA (US)

(72) Inventors: Ramesh Baliga, Redwood City, CA (US); Bruce Keyt, Hillsborough, CA (US); Dean Ng, San Francisco, CA (US)

(73) Assignee: IGM BIOSCIENCES, INC., Mountain View, CA (US)

( * ) Notice: Subject to any disclaimer, the term of this patent is extended or adjusted under 35 U.S.C. 154(b) by 0 days.

(21) Appl. No.: 18/400,974

(22) Filed: Dec. 29, 2023

(65) Prior Publication Data

US 2024/0124584 A1     Apr. 18, 2024

Related U.S. Application Data

(60) Continuation of application No. 17/110,550, filed on Dec. 3, 2020, now abandoned, and a division of application No. 16/827,100, filed on Mar. 23, 2020, now Pat. No. 10,899,835, which is a continuation of application No. PCT/US2019/020374, filed on Mar. 1, 2019.

(60) Provisional application No. 62/637,186, filed on Mar. 1, 2018.

(51) Int. Cl.
C07K 16/28      (2006.01)
A61K 39/00      (2006.01)
G01N 33/68      (2006.01)

(52) U.S. Cl.
CPC ..... *C07K 16/2809* (2013.01); *G01N 33/6854* (2013.01); *A61K 2039/505* (2013.01); *C07K 2317/21* (2013.01); *C07K 2317/35* (2013.01); *C07K 2317/52* (2013.01); *C07K 2317/56* (2013.01); *C07K 2317/622* (2013.01); *C07K 2317/624* (2013.01); *C07K 2317/94* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 7,022,309 | B2 | 4/2006 | Hiatt |
| 7,311,912 | B1 | 12/2007 | Hein |
| 7,601,351 | B1 | 10/2009 | Rosen |
| 8,377,435 | B2 | 2/2013 | Bhat |
| 9,409,976 | B2 | 8/2016 | Teng |
| 9,458,241 | B2 | 10/2016 | Bhat |
| 9,938,347 | B2 | 4/2018 | Wang |
| 9,951,134 | B2 | 4/2018 | Keyt |
| 10,351,631 | B2 | 7/2019 | Keyt |
| 10,400,038 | B2 | 9/2019 | Keyt |
| 10,570,191 | B2 | 2/2020 | Keyt |
| 10,604,559 | B2 | 3/2020 | Carroll |
| 10,618,978 | B2 | 4/2020 | Keyt |
| 10,689,449 | B2 | 6/2020 | Wang |
| 10,787,520 | B2 | 9/2020 | Keyt |
| 10,899,835 | B2 | 1/2021 | Baliga |
| 10,954,302 | B2 | 3/2021 | Keyt |
| 10,975,147 | B2 | 4/2021 | Keyt |
| 11,192,941 | B2 | 12/2021 | Keyt |
| 11,401,337 | B2 | 8/2022 | Baliga |
| 11,535,664 | B2 | 12/2022 | Carroll |
| 11,542,342 | B2 | 1/2023 | Keyt |
| 11,555,075 | B2 | 1/2023 | Keyt |
| 11,578,131 | B2 | 2/2023 | Wang |
| 11,639,389 | B2 | 5/2023 | Keyt |
| 2005/0129616 | A1 | 6/2005 | Salcedo |
| 2006/0153854 | A1 | 7/2006 | Bhat |
| 2007/0111228 | A1 | 5/2007 | Jayasena |
| 2007/0111281 | A1 | 5/2007 | Sondermann |
| 2012/0219551 | A1 | 8/2012 | Johnson |
| 2013/0164283 | A1 | 6/2013 | Bhat |
| 2014/0044739 | A1 | 2/2014 | Teng |
| 2016/0222132 | A1 | 8/2016 | Keyt |
| 2016/0368971 | A1 | 12/2016 | Keyt |
| 2017/0183409 | A1 | 6/2017 | Keyt |
| 2017/0283510 | A1 | 10/2017 | Keyt |
| 2017/0320955 | A1 | 11/2017 | Wang |
| 2018/0009897 | A1 | 1/2018 | Wang |
| 2018/0118814 | A1 | 5/2018 | Carroll |
| 2018/0118816 | A1 | 5/2018 | Keyt |
| 2018/0265596 | A1 | 9/2018 | Keyt |
| 2019/0002566 | A1 | 1/2019 | Keyt |
| 2019/0100597 | A1 | 4/2019 | Keyt |
| 2019/0185570 | A1 | 6/2019 | Keyt |

(Continued)

FOREIGN PATENT DOCUMENTS

| | | |
|---|---|---|
| JP | 2000507816 A | 6/2000 |
| JP | 2001511122 | 8/2001 |

(Continued)

OTHER PUBLICATIONS

Poosarla et al., Biotechn. Bioeng., 114(6): 1331-1342 (Year: 2017).*
Akula, S., et al., (2017), "The Appearance and Diversification of Receptors for IgM During Vertebrate Evolution", Curr. Top. Microbiol. Immunol, 408: 23 pages.
Braathen, R., et al., (2002), "The Carboxyl-terminal Domains of IgA and IgM Direct Isotype-specific Polymerization and Interaction with the Polymeric Immunoglobulin Receptor", The Journal of Biological Chemistry, 277(45): 42755-42762.
Braathen, R., et al., (2007), "Secretory Antibody Formation: Conserved Binding Interactions between J Chain and Polymeric Ig Receptor from Humans and Amphibians", The Journal of Immunology, 178: 1589-1597.

(Continued)

*Primary Examiner* — Phuong Huynh
(74) *Attorney, Agent, or Firm* — STERNE, KESSLER, GOLDSTEIN & FOX P.L.L.C.; Cynthia DeRenzo

(57) ABSTRACT

This disclosure provides an IgM antibody or IgM-like antibody comprising a variant J-chain and/or variant IgM heavy chain constant regions that can confer increased serum half-life upon the antibody.

26 Claims, 7 Drawing Sheets

Figures 3A, 3B, 3C, 3D, 3E:
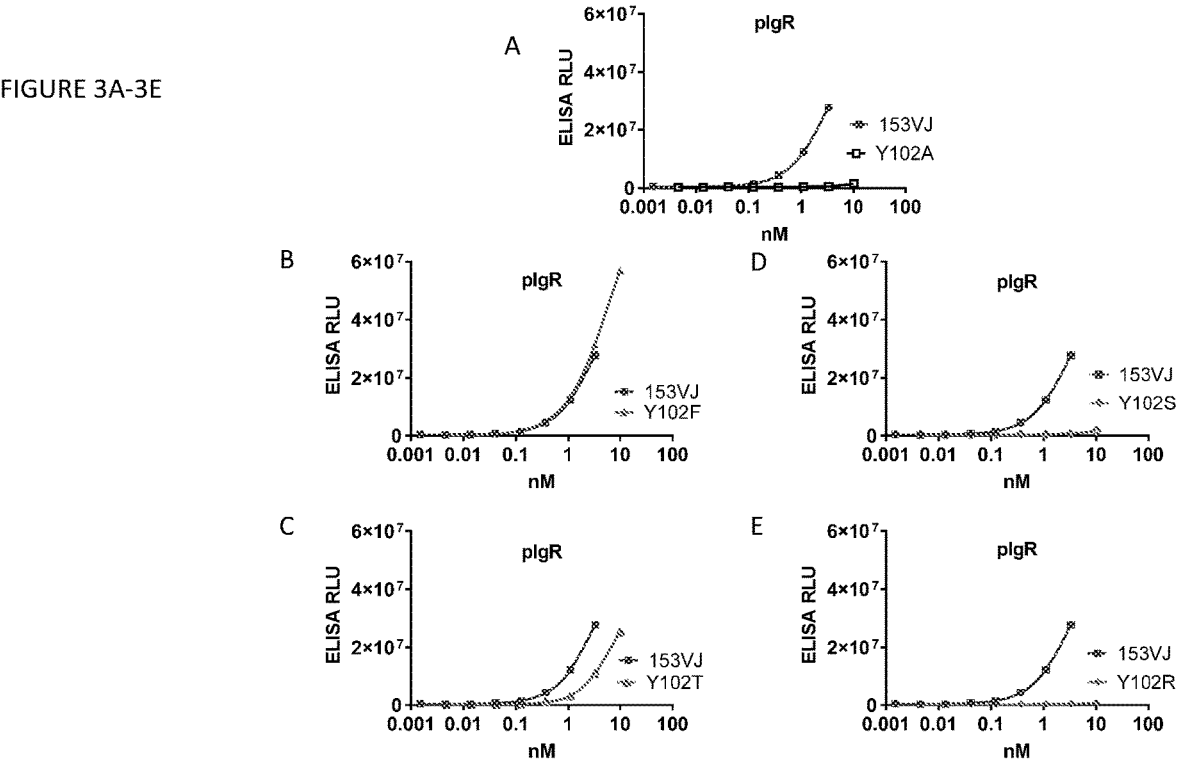

Specification includes a Sequence Listing.

(56) References Cited

U.S. PATENT DOCUMENTS

| | | |
|---|---|---|
| 2019/0330360 A1 | 10/2019 | Wang |
| 2019/0330374 A1 | 10/2019 | Wang |
| 2019/0338031 A1 | 11/2019 | Keyt |
| 2019/0338040 A1 | 11/2019 | Keyt |
| 2019/0338041 A1 | 11/2019 | Baliga |
| 2020/0190190 A1 | 6/2020 | Keyt |
| 2020/0239572 A1 | 7/2020 | Baliga |
| 2020/0255546 A1 | 8/2020 | Keyt |
| 2021/0032357 A1 | 2/2021 | Keyt |
| 2021/0147567 A1 | 5/2021 | Baliga |
| 2021/0163600 A1 | 6/2021 | Keyt |
| 2021/0380701 A1 | 12/2021 | Baliga |
| 2021/0388098 A1 | 12/2021 | Keyt |
| 2022/0106398 A1 | 4/2022 | Baliga |
| 2022/0106399 A1 | 4/2022 | Baliga |
| 2022/0169751 A1 | 6/2022 | Wang |
| 2022/0177595 A1 | 6/2022 | Wang |
| 2022/0267415 A1 | 8/2022 | Ku |
| 2022/0289856 A1 | 9/2022 | Amoury |
| 2022/0306760 A1 | 9/2022 | Keyt |
| 2022/0340676 A1 | 10/2022 | Baliga |
| 2022/0372142 A1 | 11/2022 | Baliga |
| 2022/0403009 A1 | 12/2022 | Hinton |
| 2023/0058162 A1 | 2/2023 | Hinton |
| 2023/0073926 A1 | 3/2023 | Keyt |
| 2023/0174660 A1 | 6/2023 | Wang |
| 2023/0203119 A1 | 6/2023 | Baliga |
| 2023/0203173 A1 | 6/2023 | Wang |
| 2023/0203201 A1 | 6/2023 | Keyt |
| 2023/0212293 A1 | 7/2023 | Keyt |
| 2023/0279111 A1 | 9/2023 | Keyt |
| 2024/0002514 A1 | 1/2024 | Keyt |
| 2024/0002526 A1 | 1/2024 | Chen |
| 2024/0076392 A1 | 3/2024 | Hinton |
| 2025/0051473 A1 | 2/2025 | Li |

FOREIGN PATENT DOCUMENTS

| | | |
|---|---|---|
| JP | 2011528035 | 11/2011 |
| JP | 2016514675 | 5/2016 |
| WO | WO-9734631 A1 | 9/1997 |
| WO | 1998030591 | 7/1998 |
| WO | 1998030592 | 7/1998 |
| WO | 2004110143 | 12/2004 |
| WO | 2006052641 | 5/2006 |
| WO | 2010008690 | 1/2010 |
| WO | 2013120012 | 8/2013 |
| WO | 2014144061 | 9/2014 |
| WO | 2015053887 | 4/2015 |
| WO | 2015120474 | 8/2015 |
| WO | 2015153912 | 10/2015 |
| WO | 2016118641 | 7/2016 |
| WO | 2016141303 | 9/2016 |
| WO | 2016154593 | 9/2016 |
| WO | 2016168758 | 10/2016 |
| WO | 2017059380 | 4/2017 |
| WO | 2017059387 | 4/2017 |
| WO | 2017196867 | 11/2017 |
| WO | 2018017761 | 1/2018 |
| WO | 2018017763 | 1/2018 |
| WO | 2018017888 | 1/2018 |
| WO | 2018017889 | 1/2018 |
| WO | 2018187702 | 10/2018 |
| WO | 2019165340 | 8/2019 |
| WO | 2019169314 | 9/2019 |
| WO | 2020086745 | 4/2020 |
| WO | 2020163646 | 8/2020 |
| WO | 2021030688 | 2/2021 |
| WO | 2021034646 | 2/2021 |
| WO | 2021041250 | 3/2021 |
| WO | 2021055765 | 3/2021 |
| WO | 2021141902 | 7/2021 |
| WO | 2021216756 | 10/2021 |
| WO | 2021231639 | 11/2021 |
| WO | 2022026475 | 2/2022 |
| WO | 2022109023 | 5/2022 |
| WO | 2022177870 | 8/2022 |
| WO | 2022178047 | 8/2022 |
| WO | 2023064766 | 4/2023 |
| WO | 2023064900 | 4/2023 |
| WO | 2023150677 | 8/2023 |
| WO | 2023178253 | 9/2023 |
| WO | 2024073700 | 4/2024 |
| WO | 2024138072 | 6/2024 |
| WO | 2024148336 | 7/2024 |
| WO | 2024148339 | 7/2024 |
| WO | 2024229151 | 11/2024 |

OTHER PUBLICATIONS

Brekke, O., et al., (2003), "Therapeutic antibodies for human diseases at the dawn of the twenty-first century", Nature Review Drug Discovery, 2: 52-62.

Brüggemann, M., et al., (1987), "Comparison of the effector functions of human immunoglobulins using a matched set of chimeric antibodies", J. Exp. Med, 166: 1351-1361.

Brummell, D., et al., (1993), "Probing the Combining Site of an Anti-Carbohydrate Antibody by Saturation-Mutagenesis: Role of the Heavy-Chain CDR3 Residues", Biochemistry, 32: 1180-1187.

Burks, E., et al., (1997), "In vitro Scanning Saturation Mutagenesis of an Antibody Binding Pocket", Proceedings of the National Academy of Sciences USA, vol. 94: 412-417.

Castro, C., et al., (2014), "Putting J chain back on the map: how might its expression define plasma cell development?", The Journal of Immunology, 193: 3248-3255.

Duramad, O., et al., (2014), "IGM-55.5, a novel monoclonal human recombinant IgM antibody with potent activity against B cell leukemia and lymphoma", IGM Biosciences, Inc.—Research and Development, SRI International—Cancer Pharmacology, Stanford—Department of Obstetrics and Gynecology, Abstract No. 645, AACR Annual Meeting, Apr. 5-9, 2014, San Diego CA.

Edwards, B., et al., (2003), "The Remarkable Flexibility of the Human Antibody Repertoire; Isolation of Over One Thousand Different Antibodies to a Single Protein, BLyS", J. Mol. Biol, 334: 103-118.

Ghumra, A., et al., (2009), "Structural requirements for the interaction of human IgM and IgA with the human Fcα/μ receptor", Eur J. Immunol, 39(4): 1147-1156.

Grevys. A., et al., (2015), "Fc Engineering of Human IgG1 for Altered Binding to the Neonatal Fc Receptor Affects Fc Effector Functions", The Journal of Immunology, 194: 5497-5508.

Hensel, F., et al., (2013), "Early development of PAT-SM6 for the treatment of melanoma", Melanoma Research, 23 (4): 264-275.

Honjo, K., et al., (2013), "Is Toso/IgM Fc receptor (FcμR) expressed by innate immune cells?", PNAS, 110(28): E2540-E2541.

Honjo, K., et al., (2015), "Unique Ligand-Binding Property of the Human IgM Fc Receptor", The Journal of Immunology, 194: 1975-1982.

Horton, R., et al., (2013), "Antibodies and their receptors: different potential roles in mucosal defense", frontiers in immunology, 4(200): 12 pages.

International Search Report and Written Opinion Dated May 28, 2019 issued in PCT Patent Application No. PCT/US2019/020374.

Johansen et al. "The J chain is essential for polymeric lg receptor-mediated epithelial transport of lgA," J Immunol. Nov. 1, 2001;167(9):5185-92.

Kikuno, K., et al., (2007), "Unusual biochemical features and follicular dendritic cell expression of human Fcα/μ receptor", Eur J Immunol., 37(12): 3540-3550.

Klimovich, V. B., (2011), "IgM and Its Receptors: Structural and Functional Aspects", Biochemistry, 76(5): 534-549.

Kobayashi, H., et al. (1999), "Tryptophan H33 Plays an Important Role in Pyrimidine (6-4) Pyrimidone Photoproduct Binding by a High-Affinity Antibody", Protein Engineering, vol. 12(10): 879-884.

Kubagawa, H., et al., (2009), "Identity of the elusive IgM Fc receptor (FcμR) in humans", JEM, 206(12): 2779-2793.

(56)         References Cited

OTHER PUBLICATIONS

Kubagawa, H., et al., (2017), "Authentic IgM Fc Receptor (FcμR)", Curr Top Microbiol Immunol, DOI 10.1007/82_2017_23, 21 Pages.

Liu, L., (2018), "Pharmacokinetics of monoclonal antibodies and Fc-fusion proteins", Protein Cell, 9(1): 15-32.

Lloyd, C., et al., (2009), "Modelling the human immune response: performance of a 10″ human antibody repertoire against a broad panel of therapeutically relevant antigens", Protein Engineering, Design & Selection, 22(3), 159-168.

Nguyen, T., et al., (2017), "The IgM receptor FcμR limits tonic BCR signaling by regulating expression of the IgM BCR", Nature Immunology, 18(3):321-333.

Norderhaug, I., et al., (1999), "Domain deletions in the human polymeric Ig receptor disclose differences between its dimeric IgA and pentameric IgM interaction" Eur J. Immunol, 29: 3401-3409.

Rasche, L., et al., (2015), "GRP78-directed immunotherapy in relapsed or refractory multiple myeloma—results from a phase 1 trial with the monoclonal immunoglobulin M antibody PAT-SM6", Haematologica, 100(3): 377-384.

Rudikoff, S., et al., (1982), "Single amino acid substitution altering antigen-binding specificity", Proc. Natl. Acad. Sci. USA, 79: 1979-1983.

Sakamoto, N., et al., (2001), "A novel Fc receptor for IgA and IgM is expressed on both hematopoietic and non-hematopoietic tissues", Eur. J. Immunol, 31: 1310-1316.

Strohl, W., et al., (2015), "Fusion Proteins for Half-Life Extension of Biologics as a Strategy to Make Biobetters", BioDrugs, 29: 215-239.

Vire, B., et al., (2011), "TOSO, the Fcμ Receptor, Is Highly Expressed on Chronic Lymphocytic Leukemia B Cells, Internalizes upon IgM Binding, Shuttles to the Lysosome, and Is Downregulated in Response to TLR Activation", J. Immunol, 187: 4040-4050.

Weinstein, J., et al., (2015), "IgM-Dependent Phagocytosis in Microglia Is Mediated by complement Receptor 3, Not Fcα/μ Receptor", The Journal of Immunology, 195: 5309-5317.

Wu, H., et al., (1999), "Humanization of a Murine Monoclonal Antibody by simultaneous Optimization of Framework and CDR Residues", J. Mol. Biol. 294: 151-162.

Yoo, E., et al., (2011), "Characterization of IgA and IgM binding internalization by surface-expressed human Fcα/μ receptor", Molecular Immunology, 48: 1818-1826.

U.S. Appl. No. 17/386,397, Specification, Claims, Abstract and Drawings as filed Jul. 27, 2021 with U.S. Patent Office.

U.S. Appl. No. 17/812,614, Specification, Claims, Abstract and Drawings as filed Jul. 14, 2022 with U.S. Patent Office.

U.S. Appl. No. 17/635,078, Specification, Claims, Abstract and Drawings as filed Feb. 14, 2022 with U.S. Patent Office.

U.S. Appl. No. 17/758,207, Specification, Claims, Abstract and Drawings as filed Jun. 29, 2022 with U.S. Patent Office.

U.S. Appl. No. 17/996,760, Specification, Claims, Abstract and Drawings as filed Oct. 20, 2022 with U.S. Patent Office.

U.S. Appl. No. 18/052,388, Specification, Claims, Abstract and Drawings as filed Nov. 3, 2022 with U.S. Patent Office.

U.S. Appl. No. 17/998,307, Specification, Claims, Abstract and Drawings as filed Nov. 9, 2022 with U.S. Patent Office.

U.S. Appl. No. 18/054,776, Specification, Claims, Abstract and Drawings as filed Nov. 11, 2022 with U.S. Patent Office.

U.S. Appl. No. 18/055,340, Specification, Claims, Abstract and Drawings as filed Nov. 14, 2022 with U.S. Patent Office.

Vire, B., et al., (2011), "TOSO, the Fcμ Receptor, Is Highly Expressed on Chronic Lymphocytic Leukemia B Cells, Internalizes upon IgM Binding, Shuttles to the Lysosome, and Is Downregulated in Response to TLR Activation" The Journal of Immunology, 187: 4040-4050.

Grevys, A., et al., (2022), "Antibody variable sequences have a pronounced effect on cellular transport and plasma half-life", iScience 25, 103746, 21 pages.

U.S. Appl. No. 18/252,759, Specification, Claims, Abstract and Drawings as filed May 12, 2023 with U.S. Patent Office.

U.S. Appl. No. 18/261,145, Specification, Claims, Abstract and Drawings as filed Jul. 12, 2023 with U.S. Patent Office.

U.S. Appl. No. 18/463,194, Specification, Claims, Abstract and Drawings as filed Sep. 7, 2023 with U.S. Patent Office.

U.S. Appl. No. 18/719,191 Specification, Claims, Abstract and Drawings as filed Jun. 12, 2024 with U.S. Patent Office.

U.S. Appl. No. 19/106,184 Specification, Claims, Abstract and Drawings as filed Feb. 24, 2025 with U.S. Patent Office.

U.S. Appl. No. 19/106,186 Specification, Claims, Abstract and Drawings as filed Feb. 24, 2025 with U.S. Patent Office.

\* cited by examiner

FIGURE 1A

```
Human        GSASAPTLFPLVSCENSPSDTSSVAVGCLAQDFLPDSITLSWKYKNNSDISS-TRGFPSV  59
Mouse        ASQSFPNVFPLVSCESPLSDKNLVAMGCLARDFLPSTISFTWNYQNNTEVIQGIRTFPTL  60
Cynomolgus   ESAGPFKWEPSVSSPNAPLDTNEVAVGCLAQDFLPDSITFSWKFKNNSDISKGVWGFPSV  60
Rhesus       GSASAPTLFPLVSCENAPLDTNEVAVGCLAQDFLPDSITFSWKFKNNSNISKGVWGFPSV  60
Chimpanzee   GSASAPTLFPLVSCENSPSDTSSVAVGCLAQDFLPDSITFSWKYKNNSDISS-TRGFPSV  59
Orangutan    GSASAPTLFPLVSCENSLSDTSSVAVGCLAQDFLPDSITFSWKYKNNSDISS-TRGFPSV  59

Human        LRGGKYAATSQVLLPSKDVMQGTDEHVVCKVQHPNGNKEKNVPLPVIAELPPKVSVFVPP  119
Mouse        RTGGKYLATSQVLLSPKSILEGSDEYLVCKIHYGGKNRDLHVPIPAVAEMNPNVNVFVPP  120
Cynomolgus   LRGGKYAATSQVLLASKDVMQGTDEHVVCKVQHPNGNKEQNVPLPVVAERPPNVSVFVPP  120
Rhesus       LRGGKYAATSQVLLASKDVMQGTDEHVVCKVQHPNGNKEQNVPLPVLAERPPNVSVFVPP  120
Chimpanzee   LRGGKYAATSQVLLPSKEVMQGTDEHVVCKVQHPNGNKEKNVPLPVTAELPPKVSIFVPP  119
Orangutan    LTGSKYVATSQVLLPSKDVMQGTDEHVVCKVQHPNGNKEKNVPLPVIAELPPKVSIFIPP  119

Human        RDGFFGN-PRKSKLICQATGFSPRQIQVSWLREGKQVGSGVTTDQVQAEAKESGPTTYKV  178
Mouse        RDGFSGPAPRKSKLICEATNFTPKPITVSWLKDGKLVESGFTTDPVTIENKGSTPQTYKV  180
Cynomolgus   RDGFVGN-PRESKLICQATGFSPRQIEVSWLRDGKQVGSGITTDRVEAEAKESGPTTFKV  179
Rhesus       RDGFVGN-PRESKLICQATGFSPRQIEVSWLREGKQVGSGITTDRVEAEAKESGPTTFKV  179
Chimpanzee   RDGFFGN-PRSSKLICQATGFSPRQIQVSWLREGKQVGSGVTTDQVQAEAKQSGPTTYKV  178
Orangutan    RDGFFGS-PRKSKLICQATGFSPRQIQVSWLREGKQVASGITTDQVQAEAKESGPTTYKV  178

Human        TSTLTIKESDWLGQSMFTCRVDHRGLTFQQNASSMCVPDQDTA-IRVFAIPPSFASIFLT  237
Mouse        ISTLTISEIDWLNLNVYTCRVDHRGLTFLKNVSSTCAASPSTD-ILNFTIPPSFADIFLS  239
Cynomolgus   TSTLTVSERDWLSQSVFTCRVDHRGLTFQKNVSSVCGPNPDTA-IRVFAIPPSFASIFLT  238
Rhesus       TSTLTVSERDWLSQSVFTCRVDHRGLTFQKNVSSVCGPNPDTA-IRVFAIPPSFASIFLT  238
Chimpanzee   TSTLTIKESDWLSQSVFTCRVDHRGLTFQQNASSMCSPGESRHSHPGLCHPPSFASIFLT  238
Orangutan    TSTLTINESDWLSQSMFTCRVDHRGLTFQKNASSMCSPNPNTA-IRVFAIPPSFASIFLT  237

Human        KSTKLTCLVTDLTTYDSVTISWTRQNGEAVKTHTNISESHPNATFSAVGEASICEDDWNS  297
Mouse        KSANLTCLVSNLATYETLSISWASQSGEPLETKIKIMESHPNGTFSAKGVASVCVEDWNN  299
Cynomolgus   KSTKLTCLVTDLATYDSVTITWTRQNGEALKTHTNISESHPNGTFSAVGEASICEDDWNS  298
Rhesus       KSTKLTCLVTDLATYDSVTITWTRQNGEALKTHTNISESHPNGTFSAVGEASICEDDWNS  298
Chimpanzee   KSTKLACLVTDLTTYDSLTISWTRQNGEAVKTHTNISESHPNATFSAVGEASICEDDWNS  298
Orangutan    KSTKLTCLVTDLASYDSMTISWTRQNGEAVKTHTNISESHPNATFSAVGEASICEDDWNS  297

Human        GERFTCTVTHTDLPSPLKQTISRPKGVALHRPDVYLLPPAREQLNIRESATITCLVTGFS  357
Mouse        RKEFVCTVTHRDLPSPQKKFISKPNEVHKHPPAVYLLPPAREQLNIRESATVTCLVKGFS  359
Cynomolgus   GERFRCTVTHTDLPSPLKQTISRPKGVAMHRPDVYLLPPAREQLNIRESATITCLVTGFS  358
Rhesus       GERFRCTVTHTDLPSPLKQTISRPKGVAMHRPDVYLLPPAREQLNIRESATITCLVTGFS  358
Chimpanzee   GERFTCTVTHTDLPSPLKQTISRPKEVALHRPDVYLLPPAREQLNIRELATITCLVTGFS  358
Orangutan    GERFTCTVTHADLPSPLKQTISRPKGVALHRPDVYLLPPAREQLNIRESATITCLVTGFS  357

Human        PADVFVQWMQRGQPLSPEKYVTSAPMPEPQAPGRYFAHSILTVSEEWNTGETYTCV-AH  416
Mouse        PADISVQWKQRGQLLPQEKYVTSAPMPEPGAPGFYFTHSILTVTEEWNSGETYTCVVGH  419
Cynomolgus   PADIFVQWMQRGQPLSPEKYVTSAPMPEPQAPGRYFAHSILTVSEEDWNTGETYTCVVAH  418
Rhesus       PADIFVQWMQRGQPLSPEKYVTSAPMPEPQAPGRYFAHSILTVSEEDWNTGETYTCVVAH  418
Chimpanzee   PADVFVQWMQRGQPLSPEKYVTSAPMPEPQAPGRYFAHSILTVSEEWNTGETYTCVVAH  418
Orangutan    PADVFVQWMQRGQPLSPEKYVTSAPMPEPQAPGRYFAHSILTVSEEDWNTGETYTCVVAH  417
```

FIGURE 1B

```
Human        EALPNRVTERTVDKSTGKPTLYNVSLV-------MSDTAGTCY------------------ 452
Mouse        EALPHLVTERTVDKSTGKPTLYNVSLI-------MSDTGGTCY------------------ 455
Cynomolgus   EALPNRVTERTVDKSTGK-PTLYNV---SLVILWTTLSTFVALFVLTLLYSGIVTFIKVR- 474
Rhesus       EALPNRVTERTVDKSTEGEVSADEE--GFENLWATASTFIVLFLLSLFYSTTVTLF---- 472
Chimpanzee   EALPNRVTERTVDKSTGKTHPVQRVPGHVRHSWHLLLTLLACPQAQGGRPLCVCACKLTV 478
Orangutan    EALPNRVTERTVDKSTGKPTLYNVSLV-------MSDTAGTCY------------------ 453

Human        --- 452
Mouse        --- 455
Cynomolgus   --- 474
Rhesus       --- 472
Chimpanzee   STG 481
Orangutan    --- 453
```

Figure 2

| | IgM | IgM | IgM | IgM S401A | IgM S401A | IgM E402A | IgM E402A | IgM E403A | IgM R344A | IgM E345A |
|---|---|---|---|---|---|---|---|---|---|---|
| | VJ | VJ Y102A | VJ T103A | VJ | VJ Y102A | VJ | VJ Y102A | VJ | VJ | VJ |
| m pIgR | 100% | 10% | nd | 90% | 10% | 50% | 10% | nd | nd | nd |
| h pIgR | 100% | 10% | 100% | 90% | 10% | 40% | 10% | 60% | 100% | 50% |
| m FcαμR | 100% | 10% | nd | 80% | 10% | 50% | 10% | nd | nd | nd |
| h FcαμR | 100% | 10% | 60% | 20% | 10% | 10% | 10% | 10% | 10% | 10% |
| m FcμR | 100% | 20% | nd | 20% | 30% | 20% | 20% | nd | nd | nd |
| h FcμR | 100% | 100% | 100% | 100% | 100% | 10% | 10% | 20% | 10% | 10% |

FIGURE 4

| Antibody | | A (µg/ml) | B (µg/ml) | $t_{1/2}\alpha$ (h) | $t_{1/2}\beta$ (h) | $C_0$ (µg/ml) | $AUC_{0\text{-inf}}$ (µg/ml*h) | MRT (h) |
|---|---|---|---|---|---|---|---|---|
| IgM | J | 75 | 10 | 0.5 | 8 | 85 | 177 | 8.3 |
| IgM | J Y102A | 53 | 69 | 2.6 | 37 | 122 | 3869 | 50.4 |
| IgM | VJ | 93 | 8 | 0.2 | 5 | 101 | 89 | 4.7 |
| IgM | VJ Y102A | 76 | 38 | 7.7 | 53 | 114 | 3734 | 62.1 |
| IgM S401A | VJ | 126 | 48 | 0.3 | 17 | 175 | 1232 | 23.3 |
| IgM S401A | VJ Y102A | 76 | 96 | 1.1 | 27 | 172 | 3928 | 38.4 |
| IgM E402A | VJ | 41 | 66 | 2.4 | 22 | 107 | 2225 | 29.7 |
| IgM E402A | VJ Y102A | 35 | 114 | 0.2 | 25 | 150 | 4191 | 36.6 |
| IgM | VJH | 121 | 28 | 1.4 | 33 | 148 | 1544 | 39.8 |
| IgM | VJH Y102A | 63 | 68 | 6.8 | 35 | 131 | 4074 | 44.8 |

Figure 6

| Antibody | $t_{1/2}\,\alpha$ (h) | $t_{1/2}\,\beta$ (h) | $AUC_{0-\infty}$ ($\mu$g/ml*hr) | AUC MUT/WT |
|---|---|---|---|---|
| IgM VJ | 0.49 | 17.6 | 388 | |
| IgM VJ-N49A | 0.8 | 16.0 | 625 | 1.6 |

IgM Fc AND J-CHAIN MUTATIONS THAT AFFECT IgM SERUM HALF-LIFE

CROSS-REFERENCE TO RELATED APPLICATIONS

This application is a continuation of U.S. patent application Ser. No. 17/110,550, filed on Dec. 3, 2020 (now abandoned), which is a divisional of U.S. patent application Ser. No. 16/827,100, filed Mar. 23, 2020 (now issued as U.S. Pat. No. 10,899,835), which is a continuation of PCT Application No. PCT/US2019/020374, filed Mar. 1, 2019, which claims benefit to U.S. Provisional Application No. 62/637,186, filed on Mar. 1, 2018, the contents of each of which are hereby incorporated by reference in their entireties.

REFERENCE TO SEQUENCE LISTING SUBMITTED ELECTRONICALLY

The instant application contains a Sequence Listing which has been submitted electronically in XML format and is hereby incorporated by reference in its entirety. The XML copy, created on Dec. 28, 2023, is named 012US3-Sequence-Listing.xml and is 49 kilobytes in size.

BACKGROUND

Antibodies and antibody-like molecules that can multimerize, such as IgA and IgM antibodies, have emerged as promising drug candidates in the fields of, e.g., immunooncology and infectious diseases, allowing for improved specificity, improved avidity, and the ability to bind to multiple binding targets. See, e.g., U.S. Pat. Nos. 9,951,134 and 9,938,347, and PCT Publication Nos. WO 2016/141303, WO 2016/154593, WO 2016/168758, WO 2017/059387, WO 2017 059380, WO 2018/017888, WO 2018/017763, WO 2018/017889, and WO 2018/017761, the contents of which are incorporated herein by reference in their entireties.

The pharmacokinetics (PK) and pharmacodynamics (PD) of multivalent antibodies are complex, however, and depend on both the structure of the monoclonal antibody as well as the physiological system that it targets. Moreover, different antibody classes are typically processed within a subject via different cellular and physiological systems. For example, the IgG antibody class has a serum half-life of 20 days, whereas the half-lives for IgM and IgA antibodies are only about 5-8 days. Brekke, O H., and I. Sandlie, *Nature Reviews Drug Discovery* 2: 52-62 (2003).

Antibody molecules in vivo can bind to a variety of receptors on various cells in blood or on different tissues and organs. Binding to these receptors can influence the bioavailability and biodistribution of therapeutic antibodies and their ability to reach the targets of interest. For example, antibodies of the IgG isotype are known to have long in vivo half-lives due to binding of the recycling Fc neonatal receptor (FcRn). However, IgA and IgM isotype antibodies do not bind to this key recycling receptor. Antibodies of the IgM isotype are known to bind to the Fc μ receptor (FcμR), the Fc α/μ receptor (FcαμR), and the polymeric Ig receptor (pIgR). IgM antibodies with and without a J-chain bind to FcμR (Kubagawa, H., et al., *Curr. Top. Microbiol. Immunol.* 408:25-45 (2017)), but J-chain residues at least contribute to binding of IgM antibodies to FcαμR (Ghumra, A., et al., *Eur. J. Immunol.* 39:1147-1156 (2009)) and IgM binding to pIgR is J-chain dependent (Braathen R., et al. *J. Immunol* 178:

1589-1597 (2007)). The pIgR is responsible for transporting IgM and IgA into lumen of intestine, salivary, and tear glands (see, e.g., Braathen, R., et al., *J. Biol. Chem.* 277:42755-42762 (2002)). FcαμR is responsible for the uptake of antibody bound to foreign bodies by B cells and phagocytes (Akula, S., and Hellman, L., *Curr. Top. Microbiol. Immunol.* 408:1-23 (2017)). FcμR are important for B cell development (Nguyen, T., et al., *Nature Immunol.* 18:321-333 (2017)). We hypothesized that IgM's interaction with one or more of these receptors could affect PK/PD.

J-chain is an acidic 15-kDa polypeptide, which is associated with pentameric IgM and dimeric IgA via disulfide bonds involving the penultimate cysteine residue in the 18-amino acid secretory tailpiece (tp) at the C-terminus of the IgM μ or IgA α heavy chain. The precursor human J-chain amino acid sequence is presented as SEQ ID NO: 1, and the mature human J-chain amino acid sequence is presented as SEQ ID NO: 2. The assembly of IgM binding units into a pentameric structure is thought to involve the CO and tailpiece domains of the IgM constant region. See, e.g., Braathen, R., et al., *J. Biol. Chem.* 277:42755-42762 (2002).

Despite the advances made in the design of multimeric antibodies, there remains a need to be able to manipulate the pharmacokinetic and pharmacodynamic properties of these molecules.

SUMMARY

This disclosure provides an IgM antibody or IgM-like antibody with enhanced serum half-life, where the antibody includes five bivalent antibody binding units or variants or fragments thereof and a variant J-chain or functional fragment thereof. Each binding unit of the provided antibody includes two IgM heavy chain constant regions or multimerizing fragments or variants thereof, each associated with an antigen-binding domain or subunit thereof. In certain aspects, the variant J-chain or functional fragment thereof includes one or more single amino acid substitutions, deletions, or insertions relative to a reference J-chain identical to the variant J-chain except for the one or more single amino acid substitutions, deletions, or insertions. The provided variant J-chain can affect serum half-life of the provided IgM antibody or IgM-like antibody. For example, in certain aspects the IgM antibody or IgM-like antibody exhibits an increased serum half-life upon administration to a subject animal relative to a reference IgM antibody or IgM-like antibody that is identical except for the one or more single amino acid substitutions, deletions, or insertions in the variant J-chain, and is administered in the same way to the same animal species. In certain aspects, the variant J-chain or functional fragment thereof includes one, two, three, or four single amino acid substitutions, deletions, or insertions relative to the reference J-chain.

In certain aspects, the variant J-chain or functional fragment thereof includes an amino acid substitution at the amino acid position corresponding to amino acid Y102 of the wild-type human J-chain (SEQ ID NO: 2). For example, the amino acid corresponding to Y102 of SEQ ID NO: 2 can be substituted with alanine (A), serine (S) or arginine (R). In certain aspects, the amino acid corresponding to Y102 of SEQ ID NO: 2 is substituted with alanine (A). In certain aspects, the J-chain is a variant human J-chain and includes the amino acid sequence SEQ ID NO: 3. In certain aspects, the amino acid corresponding to Y102 of SEQ ID NO: 2 is substituted with serine (S). In certain aspects, the J-chain is a variant human J-chain and includes the amino acid sequence SEQ ID NO: 4. In certain aspects, the amino acid corresponding to Y102 of SEQ ID NO: 2 is substituted with arginine (R). In certain aspects, the J-chain is a variant human J-chain and includes the amino acid sequence SEQ ID NO: 5. In certain aspects, the variant J-chain or functional fragment thereof includes an amino acid substitution at the amino acid position corresponding to amino acid T103 of the wild-type human J-chain (SEQ ID NO: 2). For example, the amino acid corresponding to T103 of SEQ ID NO: 2 can be substituted with alanine (A). In certain aspects, the J-chain is a variant human J-chain and includes the amino acid sequence SEQ ID NO: 6. In certain aspects, the variant J-chain or functional fragment thereof includes an amino acid substitution at the amino acid position corresponding to amino acid N49 or amino acid S51 of the human J-chain (SEQ ID NO: 2), where S51 is not substituted with threonine (T), or where the J-chain includes amino acid substitutions at the amino acid positions corresponding to both amino acids N49 and S51 of the human J-chain (SEQ ID NO: 2). For example, the position corresponding to N49 of SEQ ID NO: 2 can be substituted with alanine (A), glycine (G), threonine (T), serine (S) or aspartic acid (D). In certain aspects, the position corresponding to N49 of SEQ ID NO: 2 is substituted with alanine (A). In certain aspects, the J-chain is a variant human J-chain and includes the amino acid sequence SEQ ID NO: 7. In another example, the position corresponding to S51 of SEQ ID NO: 2 can be substituted with alanine (A) or glycine (G), for example, the position corresponding to S51 of SEQ ID NO: 2 is substituted with alanine (A). In certain aspects, the J-chain is a variant human J-chain and includes the amino acid sequence SEQ ID NO: 8.

In certain aspects, in an IgM antibody or IgM-like antibody that includes a variant J-chain as provided above, the IgM heavy chain constant regions or multimerizing fragments thereof can be variant IgM heavy chain constant regions including one or more single amino acid substitutions, deletions, or insertions relative to a reference IgM heavy chain constant region identical to the variant IgM heavy chain constant regions except for the one or more single amino acid substitutions, deletions, or insertions. According to these aspects, the variant IgM heavy chain constant regions can affect serum half-life of the IgM antibody or IgM-like antibody such that the IgM antibody or IgM-like antibody exhibits a further increased serum half-life upon administration to a subject animal relative to a reference IgM antibody or IgM-like antibody that is identical except for the one or more single amino acid substitutions, deletions, or insertions in the IgM heavy chain constant regions, and is administered in the same way to the same animal species. In certain aspects, the further increase in serum half-life is additive.

This disclosure further provides an IgM antibody or IgM-like antibody with enhanced serum half-life, where the IgM antibody or IgM-like antibody includes five or six bivalent antibody binding units or variants or fragments thereof, and where each binding unit includes two variant IgM heavy chain constant regions or multimerizing fragments thereof, each associated with an antigen-binding domain or subunit thereof. According to these aspects, the variant IgM heavy chain constant regions or multimerizing fragments thereof each include one or more single amino acid substitutions, deletions, or insertions relative to a reference IgM heavy chain constant region identical to the variant IgM heavy chain constant regions except for the one or more single amino acid substitutions, deletions, or insertions. Also, according to these aspects, the variant IgM heavy chain constant regions can affect serum half-life of the IgM antibody or IgM-like antibody. In certain aspects, the IgM antibody or IgM-like antibody exhibits an increased serum half-life upon administration to a subject animal relative to a reference IgM antibody or IgM-like antibody that is identical except for the one or more single amino acid substitutions, deletions, or insertions in the IgM heavy chain constant regions, and is administered in the same way to the same animal species. In certain aspects, the variant IgM heavy chain constant regions include one, two, three, or four single amino acid substitutions, deletions, or insertions relative to the reference IgM heavy chain constant region.

In certain aspects, the variant IgM heavy chain constant regions include an amino acid substitution at the amino acid position corresponding to amino acid R344 of the wild-type human IgM constant region SEQ ID NO: 12, for example, the amino acid corresponding to R344 of SEQ ID NO: 12 can be substituted with alanine (A). In certain aspects, the variant IgM heavy chain constant regions are variant human IgM heavy chain constant regions and include the amino acid sequence SEQ ID NO: 31. In certain aspects, the variant IgM heavy chain constant regions include an amino acid substitution at the amino acid position corresponding to amino acid E345 of the wild-type human IgM constant region SEQ ID NO: 12, for example, the amino acid corresponding to E345 of SEQ ID NO: 12 can be substituted with alanine (A). In certain aspects, the variant IgM heavy chain constant regions are variant human IgM heavy chain constant regions and include the amino acid sequence SEQ ID NO: 32. In certain aspects, the variant IgM heavy chain constant regions include an amino acid substitution at the amino acid position corresponding to amino acid S401 of the wild-type human IgM constant region SEQ ID NO: 12, for example, the amino acid corresponding to S401 of SEQ ID NO: 12 can be substituted with alanine (A). In certain aspects, the variant IgM heavy chain constant regions are variant human IgM heavy chain constant regions and include the amino acid sequence SEQ ID NO: 13. In certain aspects, the variant IgM heavy chain constant regions include an amino acid substitution at the amino acid position corresponding to amino acid E402 of the wild-type human IgM constant region SEQ ID NO: 12, for example, the amino acid corresponding to E402 of SEQ ID NO: 12 can be substituted with alanine (A). In certain aspects, the variant IgM heavy chain constant regions are variant human IgM heavy chain constant regions and include the amino acid sequence SEQ ID NO: 14. In certain aspects, the variant IgM heavy chain constant regions include an amino acid substitution at the amino acid position corresponding to amino acid E403 of the wild-type human IgM constant region SEQ ID NO: 12, for example, the amino acid corresponding to E403 of SEQ ID NO: 12 can be substituted with alanine (A). In certain aspects, the variant IgM heavy chain constant regions are variant human IgM heavy chain constant regions and include the amino acid sequence SEQ ID NO: 34.

In an IgM antibody or IgM-like antibody as provided herein the increased serum half-life can include an increased alpha half-life ($t_{1/2}\alpha$), an increased beta half-life ($t_{1/2}\beta$), or an increased $t_{1/2}\alpha$ and an increased $t_{1/2}\beta$. Likewise, an IgM antibody or IgM-like antibody as provided herein can further exhibit an increased peak plasma concentration (Cmax), an increased area under the curve (AUC), a modified clearance time, or any combination thereof relative to the reference antibody.

In certain aspects, the IgM heavy chain constant regions or multimerizing fragments or variants thereof of an IgM antibody or IgM-like antibody as provided herein each include a Cμ4 domain and an IgM tailpiece (tp) domain, and can further include a CO domain, a Cµ2 domain, a Cµ1 domain, or any combination thereof.

In certain aspects, the antigen-binding domain of an IgM antibody or IgM-like antibody as provided herein can be a single-chain Fv (ScFv) fragment, or a single domain variable region (VHH). In certain aspects, the antigen-binding domain subunit of an IgM antibody or IgM-like antibody as provided herein can be a heavy chain variable region (VH).

In certain aspects, each binding unit of an IgM antibody or IgM-like antibody as provided herein can further include two light chain constant regions or fragments or variants thereof each associated with an antigen-binding domain or subunit thereof; for example, the antigen-binding domain can be a scFv fragment or the antigen-binding domain subunit can be a VL.

In certain aspects, the J-chain or functional fragment or variant thereof of an IgM antibody or IgM-like antibody as provided herein can further include one or more heterologous polypeptides directly or indirectly fused to the J-chain or functional fragment or variant thereof. In certain aspects, the one or more heterologous polypeptides can be fused to the J-chain or fragment thereof via a peptide linker. Exemplary linkers can include at least 5 amino acids, but no more than 25 amino acids, and can consist of GGGGS (SEQ ID NO: 25), GGGGSGGGGS (SEQ ID NO: 26), GGGGSGGGGSGGGGS (SEQ ID NO: 27), GGGGSGGGGSGGGGSGGGGS (SEQ ID NO: 28), or GGGGSGGGGSGGGGSGGGGSGGGGS (SEQ ID NO: 29). In certain aspects, the one or more heterologous polypeptides can be fused to the N-terminus of the J-chain or fragment or variant thereof, the C-terminus of the J-chain or fragment or variant thereof, or fused to both the N-terminus and C-terminus of the J-chain or fragment or variant thereof. Where two or more heterologous polypeptides are fused to the J-chain, the heterologous polypeptides can be the same or different. In certain aspects, the at least one heterologous polypeptide can be a binding domain, for example, an antibody or antigen-binding fragment thereof, for example, a Fab fragment, a Fab' fragment, a F(ab')2 fragment, a Fd fragment, a Fv fragment, a single-chain Fv (scFv) fragment, a disulfide-linked Fv (sdFv) fragment, or any combination thereof. In certain aspects, the antigen-binding fragment is a scFv fragment. In certain aspects, the at least one heterologous polypeptide can specifically bind to CD3ε. In certain aspects, the J-chain can be a variant of the modified J-chain of SEQ ID NO: 9 (V15J), e.g., the amino acid sequence of SEQ ID NO: 10 (V15J-Y102A), the amino acid sequence of SEQ ID NO: 23 (V15J-T103A), or the amino acid sequence of SEQ ID NO: 24 (V15J-N49A).

This disclosure further provides a composition including the IgM antibody or IgM-like antibody as provided herein, and a pharmaceutically acceptable carrier.

This disclosure further provides a J-chain or functional fragment thereof that includes one or more single amino acid substitutions, deletions, or insertions relative to a reference J-chain that is identical except for the one or more single amino acid substitutions, deletions, or insertion, where the variant J-chain can affect the serum half-life of an IgM antibody or IgM-like antibody that includes the variant J-chain. In certain aspects, the variant J-chain includes the amino acid sequence SEQ ID NO: 3, SEQ ID NO: 4, SEQ ID NO: 5, SEQ ID NO: 6, SEQ ID NO: 7, SEQ ID NO: 8, SEQ ID NO: 10, SEQ ID NO: 23, SEQ ID NO: 24, or any combination thereof.

This disclosure further provides an isolated polynucleotide including a nucleic acid encoding a subunit polypeptide of an IgM or IgM-like antibody as provided herein, where the subunit polypeptide includes (a) an IgM or IgM-like heavy chain constant region or multimerizing fragment thereof, (b) an antibody light chain, or (c) a J-chain, a modified J-chain, or functional fragment or variant thereof, or (d) any combination thereof. In certain aspects, the subunit polypeptide includes an IgM or IgM-like heavy chain constant region or multimerizing fragment thereof, for example, the subunit polypeptide can include the amino acid sequence SEQ ID NO: 12, SEQ ID NO: 13, SEQ ID NO: 14, SEQ ID NO: 15, SEQ ID NO: 31, SEQ ID NO: 32, or SEQ ID NO: 34. In certain aspects, the subunit polypeptide includes an antibody light chain. In certain aspects, the subunit polypeptide can include a J-chain, a modified J-chain, or any functional fragment or variant thereof as provided herein, for example, the subunit polypeptide can include the amino acid sequence SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, SEQ ID NO: 23, or SEQ ID NO: 24. The provided polynucleotide can include one, two, three, or more nucleic acid sequences encoding two, three or more of the subunit polypeptides. Further provided is an expression vector that includes the provided polynucleotide. Further provided is a host cell that includes the provided polynucleotide or the provided expression vector.

This disclosure further provides a method for identifying variant J-chains that can increase the serum half-life of pentameric IgM antibodies or pentameric IgM-like antibodies that include the variant J-chains. The method includes testing pentameric IgM antibodies or pentameric IgM-like antibodies that include variant J-chains or fragments thereof for increased serum half-life in a subject animal relative to a reference pentameric IgM antibody or pentameric IgM-like antibody, where the variant J-chains or fragments thereof include defined amino acid insertions, deletions, or substitutions, and where the reference pentameric IgM antibody or pentameric IgM-like antibody includes a J-chain or fragment thereof identical to the variant J-chains except for the defined amino acid insertions, deletions or substitutions; and recovering those variant J-chains or fragments thereof that confer increased serum half-life upon the pentameric IgM antibodies or pentameric IgM-like antibodies relative to the reference pentameric IgM antibody or pentameric IgM-like antibody.

This disclosure further provides a method of identifying variant J-chains that can increase the serum half-life of pentameric IgM antibodies or pentameric IgM-like antibodies including the variant J-chains. The method includes testing pentameric IgM antibodies or pentameric IgM-like antibodies that include variant J-chains or fragments thereof for their level of binding to the Fc alpha-mu receptor (FcαµR), the polymeric Ig receptor (pIgR), or both the FcαµR and the pIgR, where the variant J-chains or fragments thereof include defined amino acid insertions, deletions, or substitutions; and recovering those variant J-chains or fragments thereof that confer reduced FcαµR binding ability, reduced pIgR binding ability, or reduced FcαµR and pIgR binding ability upon the pentameric IgM antibodies or pentameric IgM-like antibodies relative to a reference pentameric IgM antibody or pentameric IgM-like antibody that includes a J-chain or fragment thereof identical to the variant J-chains except for the defined amino acid insertions, deletions or substitutions. This method can further include testing pentameric IgM antibodies or pentameric IgM-like antibodies that include the recovered variant J-chains or fragments thereof for increased serum half-life in a subject animal relative to a reference pentameric IgM antibody or pentameric IgM-like antibody that includes a J-chain or fragment thereof identical to the recovered variant J-chains or fragments thereof except for the defined amino acid insertions, deletions or substitutions.

This disclosure further provides a method for identifying variant IgM heavy chain constant regions that can increase the serum half-life of an IgM antibody or IgM-like antibody that includes the variant IgM heavy chain constant regions. The method includes testing IgM antibodies or IgM-like antibodies that include variant IgM heavy chain constant regions for increased serum half-life in a subject animal relative to a reference pentameric IgM antibody or pentameric IgM-like antibody, where the variant IgM heavy chain constant regions include defined amino acid insertions, deletions, or substitutions, and where the reference IgM antibody or IgM-like antibody includes IgM heavy chain constant regions identical to the variant IgM heavy chain constant regions except for the defined amino acid insertions, deletions or substitutions; and recovering those IgM antibodies or IgM-like antibodies including variant IgM heavy chain constant regions that confer increased serum half-life upon the IgM antibodies or IgM-like antibodies including the variant IgM heavy chain constant regions relative to the reference IgM antibody or IgM-like antibody.

This disclosure further provides a method for identifying variant IgM heavy chain constant regions that can increase the serum half-life of an IgM antibody or IgM-like antibody including the variant IgM heavy chain constant regions. The method includes testing IgM antibodies or IgM-like antibodies including variant IgM heavy chain constant regions for their level of binding to the Fc alpha-mu receptor (FcαμR), Fc mu receptor (FcμR), the polymeric Ig receptor (pIgR), any combination of two of the receptors, or all three of the receptors, where the variant IgM heavy chain constant regions include defined amino acid insertions, deletions, or substitutions; and recovering those IgM antibodies or IgM-like antibodies including variant IgM heavy chain constant regions that confer reduced FcαμR binding ability, reduced FcμR binding ability, reduced pIgR binding ability, reduced ability to bind to any two of the receptors, or reduced ability to bind to all three of the receptors, upon the IgM antibodies or IgM-like antibodies including the variant IgM heavy chain constant regions relative to a reference IgM antibody or IgM-like antibody that includes IgM heavy chain constant regions identical to the variant IgM heavy chain constant regions except for the defined amino acid insertions, deletions or substitutions. This method can further include testing the recovered IgM antibodies or IgM-like antibodies that include the variant IgM heavy chain constant regions for increased serum half-life in a subject animal relative to a reference IgM antibody or IgM-like antibody that includes IgM heavy chain constant regions identical to the variant IgM heavy chain constant regions except for the defined amino acid insertions, deletions or substitutions.

BRIEF DESCRIPTION OF THE DRAWINGS/FIGURES

FIGS. 1A-1B show an alignment of the human IgM heavy chain constant region amino acid sequence (SEQ ID NO: 12) with those of mouse (GenBank: CAC20701.1, SEQ ID NO: 16), cynomolgus monkey (GenBank: EHH62210.1, SEQ ID NO: 30), rhesus monkey (GenBank: AAD02420.1, SEQ ID NO: 17), chimpanzee (GenBank: PNI10622.1, SEQ ID NO: 18), and Sumatran orangutan (GenBank: PNJ04968.1, SEQ ID NO: 19). The amino acids corresponding to amino acids R345, E346, S401, E402, and E403 of SEQ ID NO: 12 are boxed.

FIG. 2 is a table summarizing the binding of human and mouse immunoglobulin receptors to anti-CD20/anti-CD3 bispecific IGMs comprising various mutations in the J-chain and/or in the IgM heavy chain constant region measured by ELISA. "WT" signifies anti-CD20 1.5.3 antibodies with the IgM constant regions and V15J regions as described in PCT Publication No. WO 2016/141303 prior to introduction of the alanine substitutions. The percentages indicate the extent of receptor binding relative to the "WT" starting antibody. The percentages indicate the level of receptor binding relative to an IgM pentamer comprising wild-type IgM heavy chain constant regions ("IgM," SEQ ID NO: 12) and a modified J-chain comprising a wild-type human J-chain fused at its N-terminus to an scFv that binds to CD3 ("VJ" or "V15J," SEQ ID NO: 9), which is designated as 100%.

FIGS. 3A-3E are graphs showing the binding of various anti-CD20/anti-CD3 bispecific IgMs, with amino acid substitution mutations at a position in the J-chain corresponding to amino acid Y102 of SEQ ID NO: 2, to pIgR. Each graph compares a single mutant with the "Wild-type" anti-CD20 1.5.3 IgM antibody 1.5.3VJ (closed squares). FIG. 3A: Y102A mutation (open squares); FIG. 3B: Y102F mutation (closed triangles); FIG. 3C: Y102T mutation (open triangles); FIG. 3D: Y102S mutation (open diamonds); FIG. 3E: Y102R mutation (closed diamonds).

FIG. 4 is a table summarizing pharmacokinetic data in mice for anti-CD3 monospecific IgMs and anti-CD20/anti-CD3 bispecific IGMs comprising various mutations in the J-chain and/or in the IgM heavy chain constant region as compared to controls. "WT IgM" signifies anti-CD20 1.5.3 antibodies with the IgM constant regions as described in PCT Publication No. WO 2016/141303 prior to introduction of the alanine substitutions. "WT J" and "WT VJ" and wild-type J-chains ("J") or anti-CD3 modified J-chains "VJ" regions as described in PCT Publication No. WO 2016/141303 prior to introduction of the alanine substitutions. "VJH" signifies the "VJ" anti-CD3 modified J-chain further comprising human serum albumin fused to the C-terminus (presented herein as SEQ ID NO: 11). "A" is the serum concentration of antibody measured at $t_{1/2}$Alpha; "B" is the serum concentration of antibody measured at $t_{1/2}$Beta; "$t_{1/2}$Alpha" is the alpha half-life (in hours); "$t_{1/2}$Beta" is the beta half-life measured in hours, "$C_0$" is the serum antibody concentration in μg/ml measured at zero time; $AUC_{0-inf}$" is the area under the curve from zero time to infinity measured in μg/ml*h; and "MRT" is the mean residence time in serum for the antibody measured in hours.

Figure 5:
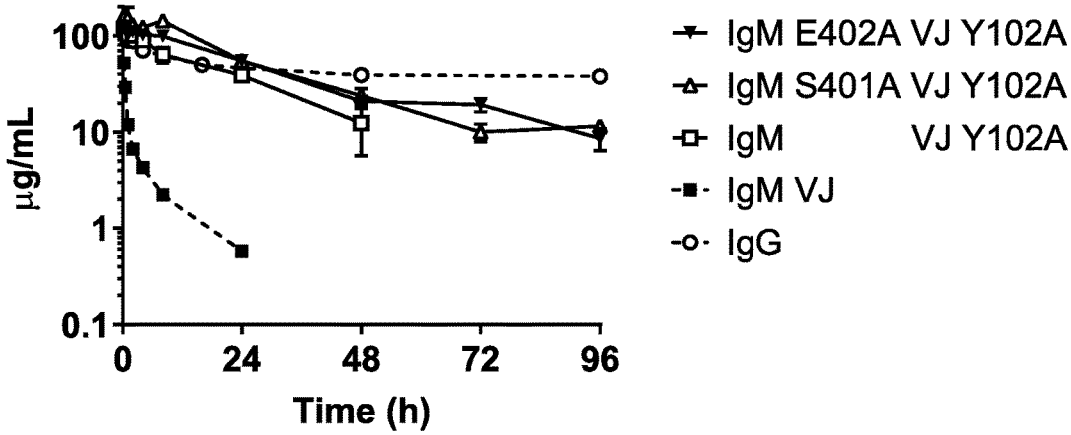

FIG. 5 is a curve showing the effect of the J-chain Y102A mutation either alone, or in combination with either the IgM heavy chain S401A or E401A mutations, on overall serum half-life of an anti-CD20/anti-CD3 IgM bispecific antibody as compared to an IgG antibody comprising the same anti-CD20 VH and VL binding regions (153 IgG). 153 IgG: open circles; IgM 1.5.3 V15J: closed squares; IgM 1.5.3 V15J-Y102A: open squares; IgM 1.5.3 S401A/V15J-Y102A: open triangles; IgM 1.5.3 E402A/V15J-Y102A: closed inverted triangles.

FIG. 6 is a table comparing pharmacokinetic parameters of IgM 1.5.3 V15J and IgM 1.5.3 V15J-N49A.

DETAILED DESCRIPTION

Definitions

It is to be noted that the term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/ blocking groups, proteolytic cleavage, or modification by non-naturally occurring amino acids. A polypeptide can be derived from a biological source or produced by recombinant technology but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations and are referred to as unfolded. As used herein, the term glycoprotein refers to a protein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides which have been separated, fractionated, or partially or substantially purified by any suitable technique.

As used herein, the term "a non-naturally occurring polypeptide" or any grammatical variants thereof, is a conditional definition that explicitly excludes, but only excludes, those forms of the polypeptide that are, or might be, determined or interpreted by a judge or an administrative or judicial body, to be "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides which retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can comprise conservative or non-conservative amino acid substitutions, deletions or additions. Derivatives are polypeptides that have been altered so as to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the antibody binds. Methods of identifying nucleotide and amino acid conservative substitutions which do not eliminate antigen-binding are well-known in the art (see, e.g., Brummell et al., *Biochem.* 32: 1180-1 187 (1993); Kobayashi et al., *Protein Eng.* 12(10): 879-884 (1999); and Burks et al., *Proc. Natl. Acad. Sci. USA* 94:412-417 (1997)).

The term "polynucleotide" is intended to encompass a singular nucleic acid as well as plural nucleic acids and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, which has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, the term "a non-naturally occurring polynucleotide" or any grammatical variants thereof, is a conditional definition that explicitly excludes, but only excludes, those forms of the nucleic acid or polynucleotide that are, or might be, determined or interpreted by a judge, or an administrative or judicial body, to be "naturally-occurring."

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions which encode secretory or signal peptides, which direct the secretion of a polypeptide encoded by a polynucleotide as disclosed herein. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

As used herein, the term "binding molecule" refers in its broadest sense to a molecule that specifically binds to a receptor, e.g., an epitope or an antigenic determinant. As described further herein, a binding molecule can comprise one of more "antigen-binding domains" described herein. A non-limiting example of a binding molecule is an antibody or antibody-like molecule as described in detail herein that retains antigen-specific binding. In certain aspects a "binding molecule" comprises an antibody or antibody-like molecule as described in detail herein.

As used herein, the terms "binding domain" or "antigen-binding domain" (can be used interchangeably) refer to a region of a binding molecule, e.g., an antibody or antibody-like molecule, that is necessary and sufficient to specifically bind to an epitope. For example, an "Fv," e.g., a variable heavy chain and variable light chain of an antibody, either as two separate polypeptide subunits or as a single chain, is considered to be a "binding domain." Other antigen-binding domains include, without limitation, the variable heavy chain (VHH) of an antibody derived from a camelid species, or six immunoglobulin complementarity determining regions (CDRs) expressed in a fibronectin scaffold. A "binding molecule," or "antibody" as described herein can include one, two, three, four, five, six, seven, eight, nine, ten, eleven, twelve or more "antigen-binding domains."

The terms "antibody" and "immunoglobulin" can be used interchangeably herein. An antibody (or a fragment, variant, or derivative thereof as disclosed herein) includes at least the variable domain of a heavy chain (for camelid species) or at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). Unless otherwise stated, the term "antibody" encompasses anything ranging from a small antigen-binding fragment of an antibody to a full sized antibody, e.g., an IgG antibody that includes two complete heavy chains and two complete light chains, an IgA antibody that includes four complete heavy chains and four complete light chains and optionally includes a J-chain and/or a secretory component, or an IgM antibody that includes ten or twelve complete heavy chains and ten or twelve complete light chains and optionally includes a J-chain or functional fragment thereof.

The term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4 or α1-α2)). It is the nature of this chain that determines the "isotype" of the antibody as IgG, IgM, IgA IgG, or IgE, respectively. The immunoglobulin subclasses (subtypes) e.g., $IgG_1$, $IgG_2$, $IgG_3$, $IgG_4$, $IgA_1$, $IgA_2$, etc. are well characterized and are known to confer functional specialization. Modified versions of each of these immunoglobulins are readily discernible to the skilled artisan in view of the instant disclosure and, accordingly, are within the scope of this disclosure.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are expressed, e.g., by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure, or a "binding unit."

The term "binding unit" is used herein to refer to the portion of a binding molecule, e.g., an antibody, antibody-like molecule, antigen-binding fragment thereof, or multimerizing fragment thereof, which corresponds to a standard "H2L2" immunoglobulin structure, i.e., two heavy chains or fragments thereof and two light chains or fragments thereof. In certain aspects, e.g., where the binding molecule is a bivalent IgG antibody or antigen-binding fragment thereof, the terms "binding molecule" and "binding unit" are equivalent. In other aspects, e.g., where the binding molecule is multimeric, e.g., a dimeric IgA antibody or IgA-like antibody, a pentameric IgM antibody or IgM-like antibody, or a hexameric IgM antibody or IgM-like antibody, the binding molecule comprises two or more "binding units." Two in the case of an IgA dimer, or five or six in the case of an IgM pentamer or hexamer, respectively. A binding unit need not include full-length antibody heavy and light chains, but will typically be bivalent, i.e., will include two "antigen-binding domains," as defined above. As used herein, certain binding molecules provided in this disclosure are "dimeric," and include two bivalent binding units that include IgA constant regions or multimerizing fragments thereof. Certain binding molecules provided in this disclosure are "pentameric" or "hexameric," and include five or six bivalent binding units that include IgM constant regions or multimerizing fragments thereof. A binding molecule, e.g., an antibody or antibody-like molecule, comprising two or more, e.g., two, five, or six binding units, is referred to herein as "multimeric."

As used herein, an "IgM-like antibody" refers to a variant antibody that still retains the ability to form hexamers, or in association with J-chain, form pentamers. An IgM-like antibody typically includes at least the Cμ4-tp domains of the IgM constant region but can include heavy chain constant region domains from other antibody isotypes, e.g., IgG, from the same species or from a different species. An IgM-like antibody can likewise be an antibody fragment in which one or more constant regions are deleted, as long as the IgM-like antibody is capable of forming hexamers and/or pentamers. Thus, an IgM-like antibody can be a hybrid IgM/IgG antibody or can be a multimerizing fragment of an IgM antibody.

The terms "valency," "bivalent," "multivalent" and grammatical equivalents, refer to the number of antigen-binding domains in given binding molecule, e.g., antibody or antibody-like molecule, or in a given binding unit. As such, the terms "bivalent", "tetravalent", and "hexavalent" in reference to a given binding molecule, e.g., an IgM antibody, IgM-like antibody or multimerizing fragment thereof, denote the presence of two antigen-binding domains, four antigen-binding domains, and six antigen-binding domains, respectively. A typical IgM antibody or IgM-like antibody where each binding unit is bivalent, can have 10 or 12 valencies. A bivalent or multivalent binding molecule, e.g., antibody or antibody-like molecule, can be monospecific, i.e., all of the antigen-binding domains are the same, or can be bispecific or multispecific, e.g., where two or more antigen-binding domains are different, e.g., bind to different epitopes on the same antigen, or bind to entirely different antigens.

The term "epitope" includes any molecular determinant capable of specific binding to an antigen-binding domain of an antibody or antibody-like molecule. In certain aspects, an epitope can include chemically active surface groupings of molecules such as amino acids, sugar side chains, phosphoryl, or sulfonyl, and, in certain aspects, can have three-dimensional structural characteristics, and/or specific charge characteristics. An epitope is a region of a target that is bound by an antigen-binding domain of an antibody.

The term "target" is used in the broadest sense to include substances that can be bound by a binding molecule, e.g., antibody or antibody-like molecule. A target can be, e.g., a polypeptide, a nucleic acid, a carbohydrate, a lipid, or other molecule. Moreover, a "target" can, for example, be a cell, an organ, or an organism that comprises an epitope bound that can be bound by a binding molecule, e.g., antibody or antibody-like molecule.

Both the light and heavy chains are divided into regions of structural and functional homology. The terms "constant" and "variable" are used functionally. In this regard, it will be appreciated that the variable domains of both the variable light (VL) and variable heavy (VH) chain portions determine antigen recognition and specificity. Conversely, the constant domains of the light chain (CL) and the heavy chain (e.g., CH1, CH2, CH3, or CH4) confer biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 (or CH4 in the case of IgM) and CL domains actually comprise the carboxy-terminus of the heavy and light chain, respectively.

A "full length IgM antibody heavy chain" is a polypeptide that includes, in N-terminal to C-terminal direction, an antibody heavy chain variable domain (VH), an antibody heavy chain constant domain 1 (CM1 or Cμ1), an antibody heavy chain constant domain 2 (CM2 or Cμ2), an antibody heavy chain constant domain 3 (CM3 or Cμ3), and an antibody heavy chain constant domain 4 (CM4 or Cμ4) that can include a tailpiece.

As indicated above, variable region(s) allows a binding molecule, e.g., antibody or antibody-like molecule, to selectively recognize and specifically bind epitopes on antigens. That is, the VL domain and VH domain, or subset of the complementarity determining regions (CDRs), of a binding molecule, e.g., an antibody or antibody-like molecule, combine to form the antigen-binding domain. More specifically, an antigen-binding domain can be defined by three CDRs on each of the VH and VL chains. Certain antibodies form larger structures. For example, IgA can form a molecule that includes two H2L2 binding units and a J-chain covalently connected via disulfide bonds, which can be further associated with a secretory component, and IgM can form a pentameric or hexameric molecule that includes five or six H2L2 binding units and optionally a J-chain covalently connected via disulfide bonds.

The six "complementarity determining regions" or "CDRs" present in an antibody antigen-binding domain are short, non-contiguous sequences of amino acids that are specifically positioned to form the antigen-binding domain as the antibody assumes its three-dimensional configuration in an aqueous environment. The remainder of the amino acids in the antigen-binding domain, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, *J. Mol. Biol.,* 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These particular regions have been described, for example, by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference. The Kabat and Chothia definitions include overlapping or subsets of amino acids when compared against each other. Nevertheless, application of either definition (or other definitions known to those of ordinary skill in the art) to refer to a CDR of an antibody or variant thereof is intended to be within the scope of the term as defined and used herein, unless otherwise indicated. The appropriate amino acids which encompass the CDRs as defined by each of the above cited references are set forth below in Table 1 as a comparison. The exact amino acid numbers which encompass a particular CDR will vary depending on the sequence and size of the CDR. Those skilled in the art can routinely determine which amino acids comprise a particular CDR given the variable region amino acid sequence of the antibody.

TABLE 1

| CDR Definitions* | | |
| --- | --- | --- |
| | Kabat | Chothia |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

*Numbering of all CDR definitions in Table 1 is according to the numbering conventions set forth by Kabat et al. (see below).

Antibody variable domains can also be analyzed, e.g., using the IMGT information system (imgt_dot_cines_dot_fr/) (IMGT®/V-Quest) to identify variable region segments, including CDRs. (See, e.g., Brochet et al., Nucl. Acids Res., 36:W503-508, 2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for all amino acid sequences in this disclosure.

The Kabat numbering system for the human IgM constant domain can be found in Kabat, et. al. "Tabulation and Analysis of Amino acid and nucleic acid Sequences of Precursors, V-Regions, C-Regions, J-Chain, T-Cell Receptors for Antigen, T-Cell Surface Antigens, β-2 Microglobulins, Major Histocompatibility Antigens, Thy-1, Complement, C-Reactive Protein, Thymopoietin, Integrins, Post-gamma Globulin, α-2 Macroglobulins, and Other Related Proteins," U.S. Dept. of Health and Human Services (1991). IgM constant regions can be numbered sequentially (i.e., amino acid #1 starting with the first amino acid of the constant region, or by using the Kabat numbering scheme. A comparison of the numbering of the human IgM constant region sequentially (presented herein as SEQ ID NO: 12) and by the Kabat system is set out below. The underlined amino acid residues are not accounted for in the Kabat system:

between the antigen-binding domain and the epitope. According to this definition, a binding molecule, e.g., antibody or antibody-like molecule, is said to "specifically bind" to an epitope when it binds to that epitope, via its antigen-binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

A binding molecule, e.g., an antibody or fragment, variant, or derivative thereof disclosed herein can be said to bind a target antigen with an off rate (k(off)) of less than or equal to $5 \times 10^{-2}$ sec$^{-1}$, $10^{-2}$ sec$^{-1}$, $5 \times 10^{-3}$ sec$^{-1}$, $10^{-3}$ sec$^{-1}$, $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$.

A binding molecule, e.g., an antibody or antigen-binding fragment, variant, or derivative disclosed herein can be said to bind a target antigen with an on rate (k(on)) of greater than or equal to $10^{-3}$ M$^{-1}$ sec$^{-1}$, $5 \times 10^{3}$ M$^{-1}$ sec$^{-1}$, $10^{4}$ M$^{-1}$ sec$^{-1}$, $5 \times 10^{4}$ M$^{-1}$ sec$^{-1}$, $10^{5}$ M$^{-1}$ sec$^{-1}$, $5 \times 10^{5}$ M$^{-1}$ sec$^{-1}$, $10^{6}$ M$^{-1}$ sec$^{-1}$, or $5 \times 10^{6}$ M$^{-1}$ sec$^{-1}$ or $10^{7}$ M$^{-1}$ sec$^{-1}$.

A binding molecule, e.g., an antibody or fragment, variant, or derivative thereof is said to competitively inhibit binding of a reference antibody or antigen-binding fragment to a given epitope if it preferentially binds to that epitope to the extent that it blocks, to some degree, binding of the reference antibody or antigen-binding fragment to the epitope. Competitive inhibition can be determined by any

```
Sequential/
KABAT numbering key for IgM heavy chain
                                          (SEQ ID NO: 12)
  1/127    GSASAPTLFP LVSCENSPSD TSSVAVGCLA QDFLPDSITF SWKYKNNSDI

51/176    SSTRGFPSVL RGGKYAATSQ VLLPSKDVMQ GTDEHVVCKV QHPNGNKEKN

101/226    VPLPVIAELP PKVSVFVPPR DGFFGNPRKS KLICQATGFS PRQIQVSWLR

151/274    EGKQVGSGVT TDQVQAEAKE SGPTTYKVTS TLTIKESDWL SQSMFTCRVD

201/324    HRGLTFQQNA SSMCVPDQDT AIRVFAIPPS FASIFLTKST KLTCLVTDLT

251/374    TYDSVTISWT RQNGEAVKTH TNISESHPNA TFSAVGEASI CEDDWNSGER

301/424    FTCTVTHTDL PSPLKQTISR PKGVALHRPD VYLLPPAREQ LNLRESATIT

351/474    CLVTGFSPAD VFVQWMQRGQ PLSPEKYVTS APMPEPQAPG RYFAHSILTV

401/524    SEEEWNTGET YTCVVAHEAL PNRVTERTVD KSTGKPTLYN VSLVMSDTAG

451/574    TCY
```

Binding molecules, e.g., antibodies, antibody-like molecules, antigen-binding fragments, variants, or derivatives thereof, and/or multimerizing fragments thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019.

By "specifically binds," it is generally meant that a binding molecule, e.g., an antibody or fragment, variant, or derivative thereof binds to an epitope via its antigen-binding domain, and that the binding entails some complementarity method known in the art, for example, competition ELISA assays. A binding molecule can be said to competitively inhibit binding of the reference antibody or antigen-binding fragment to a given epitope by at least 90%, at least 80%, at least 70%, at least 60%, or at least 50%.

As used herein, the term "affinity" refers to a measure of the strength of the binding of an individual epitope with one or more antigen-binding domains, e.g., of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of antigen-binding domains and an antigen. See, e.g., Harlow at pages 29-34. Avidity is related to both the affinity of individual antigen-binding domains in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

Binding molecules, e.g., antibodies or fragments, variants, or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross-reactive epitope generally contains many of the same complementary structural features as the inducing epitope, and in some cases, can actually fit better than the original.

A binding molecule, e.g., an antibody or fragment, variant, or derivative thereof can also be described or specified in terms of their binding affinity to an antigen. For example, a binding molecule can bind to an antigen with a dissociation constant or $K_D$ no greater than $5\times10^{-2}$ M, $10^{-2}$ M, $5\times10^{-3}$ M, 10–3 M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ m, $5\times10^{-13}$ M, $10^{-13}$ M, $5\times10^{-14}$ M, $10^{-14}$ m, $5\times10^{-15}$ M, or $10^{-15}$ M.

"Antigen-binding antibody fragments" including single-chain antibodies or other antigen-binding domains can exist alone or in combination with one or more of the following: hinge region, CH1, CH2, CH3, or CH4 domains, J-chain, or secretory component. Also included are antigen-binding fragments that can include any combination of variable region(s) with one or more of a hinge region, CH1, CH2, CH3, or CH4 domains, a J-chain, or a secretory component. Binding molecules, e.g., antibodies, or antigen-binding fragments thereof can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and can in some instances express endogenous immunoglobulins and some not, as described infra and, for example in, U.S. Pat. No. 5,939,598 by Kucherlapati et al. According to aspects of the present disclosure, an IgM or IgM-like antibody as provided herein can include an antigen-binding fragment of an antibody, e.g., a scFv fragment, so long as the IgM or IgM-like antibody is able to form a multimer, e.g., a hexamer or a pentamer.

As used herein, the term "heavy chain subunit" includes amino acid sequences derived from an immunoglobulin heavy chain, a binding molecule, e.g., an antibody or antibody-like molecule comprising a heavy chain subunit can include at least one of: a VH domain, a CH1 domain, a hinge (e.g., upper, middle, and/or lower hinge region) domain, a CH2 domain, a CH3 domain, a CH4 domain, or a variant or fragment thereof. For example, a binding molecule, e.g., an antibody, antibody-like molecule, or fragment, variant, or derivative thereof can include without limitation, in addition to a VH domain, a CH1 domain; a CH1 domain, a hinge, and a CH2 domain; a CH1 domain and a CH3 domain; a CH1 domain, a hinge, and a CH3 domain; or a CH1 domain, a hinge domain, a CH2 domain, and a CH3 domain. In certain aspects a binding molecule, e.g., an antibody, antibody-like molecule, or fragment, variant, or derivative thereof can include, in addition to a VH domain, a CH3 domain and a CH4 domain; or a CH3 domain, a CH4 domain, and a J-chain. Further, a binding molecule, e.g., antibody or antibody-like molecule, for use in the disclosure can lack certain constant region portions, e.g., all or part of a CH2 domain. It will be understood by one of ordinary skill in the art that these domains (e.g., the heavy chain subunit) can be modified such that they vary in amino acid sequence from the original immunoglobulin molecule. According to aspects of the present disclosure, an IgM or IgM-like antibody as provided herein comprises sufficient portions of an IgM heavy chain constant region to allow the IgM or IgM-like antibody to form a multimer, e.g., a hexamer or a pentamer.

As used herein, the term "light chain subunit" includes amino acid sequences derived from an immunoglobulin light chain. The light chain subunit includes at least a VL, and can further include a CL (e.g., Cκ or Cλ) domain.

Binding molecules, e.g., antibodies, antibody-like molecules, antigen-binding fragments, variants, or derivatives thereof, or multimerizing fragments thereof can be described or specified in terms of the epitope(s) or portion(s) of an antigen that they recognize or specifically bind. The portion of a target antigen that specifically interacts with the antigen-binding domain of an antibody is an "epitope," or an "antigenic determinant." A target antigen can comprise a single epitope or at least two epitopes, and can include any number of epitopes, depending on the size, conformation, and type of antigen.

As previously indicated, the subunit structures and three-dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of a typical IgG heavy chain molecule.

As used herein, the term "CH2 domain" includes the portion of a heavy chain molecule that extends, e.g., from about amino acid 244 to amino acid 360 of an IgG antibody using conventional numbering schemes (amino acids 244 to 360, Kabat numbering system; and amino acids 231-340, EU numbering system; see Kabat E A et al., op. cit. The CH3 domain extends from the CH2 domain to the C-terminal of the IgG molecule and comprises approximately 108 amino acids. Certain immunoglobulin classes, e.g., IgM, further include a CH4 region.

As used herein, the term "hinge region" includes the portion of a heavy chain molecule that joins the CH1 domain to the CH2 domain in IgG, IgA, and IgD heavy chains. This hinge region comprises approximately 25 amino acids and is flexible, thus allowing the two N-terminal antigen-binding regions to move independently.

As used herein, the term "disulfide bond" includes the covalent bond formed between two sulfur atoms. The amino acid cysteine comprises a thiol group that can form a disulfide bond or bridge with a second thiol group.

As used herein, the term "chimeric antibody" refers to an antibody in which the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The terms "multispecific antibody" or "bispecific antibody" refer to an antibody or antibody-like molecule that has antigen-binding domains for two or more different epitopes within a single antibody molecule. Other binding molecules in addition to the canonical antibody structure can be constructed with two binding specificities. Epitope binding by bispecific or multispecific antibodies can be simultaneous or sequential. Triomas and hybrid hybridomas are two examples of cell lines that can secrete bispecific antibodies. Bispecific antibodies can also be constructed by recombinant means. (Strohlein and Heiss, *Future Oncol.* 6:1387-94 (2010); Mabry and Snavely, *IDrugs.* 13:543-9 (2010)). A bispecific antibody can also be a diabody.

As used herein, the term "engineered antibody" refers to an antibody in which the variable domain in either the heavy and light chain or both is altered by at least partial replacement of one or more amino acids in either the CDR or framework regions. In certain aspects entire CDRs from an antibody of known specificity can be grafted into the framework regions of a heterologous antibody. Although alternate CDRs can be derived from an antibody of the same class or even subclass as the antibody from which the framework regions are derived, CDRs can also be derived from an antibody of different class, e.g., from an antibody from a different species. An engineered antibody in which one or more "donor" CDRs from a non-human antibody of known specificity are grafted into a human heavy or light chain framework region is referred to herein as a "humanized antibody." In certain aspects not all of the CDRs are replaced with the complete CDRs from the donor variable region and yet the antigen-binding capacity of the donor can still be transferred to the recipient variable domains. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which amino acids that neighbor each other in the sequence are contiguous in the primary structure of the polypeptide. A portion of a polypeptide that is "amino-terminal" or "N-terminal" to another portion of a polypeptide is that portion that comes earlier in the sequential polypeptide chain. Similarly, a portion of a polypeptide that is "carboxy-terminal" or "C-terminal" to another portion of a polypeptide is that portion that comes later in the sequential polypeptide chain. For example, in a typical antibody, the variable domain is "N-terminal" to the constant region, and the constant region is "C-terminal" to the variable domain.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into RNA, e.g., messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

Terms such as "treating" or "treatment" or "to treat" or "alleviating" or "to alleviate" refer to therapeutic measures that cure, slow down, lessen symptoms of, and/or halt or slow the progression of an existing diagnosed pathologic condition or disorder. Terms such as "prevent," "prevention," "avoid," "deterrence" and the like refer to prophylactic or preventative measures that prevent the development of an undiagnosed targeted pathologic condition or disorder. Thus, "those in need of treatment" can include those already with the disorder; those prone to have the disorder; and those in whom the disorder is to be prevented.

As used herein the terms "serum half-life" or "plasma half-life" refer to the time it takes (e.g., in minutes, hours, or days) following administration for the serum or plasma concentration of a drug, e.g., a binding molecule such as an antibody, antibody-like molecule or fragment thereof as described herein, to be reduced by 50%. Two half-lives can be described: the alpha half-life, a half-life, or $t_{1/2}\alpha$, which is the rate of decline in plasma concentrations due to the process of drug redistribution from the central compartment, e.g., the blood in the case of intravenous delivery, to a peripheral compartment (e.g., a tissue or organ), and the beta half-life, β half-life, or $t_{1/2}\beta$ which is the rate of decline due to the processes of excretion or metabolism.

As used herein the term "area under the plasma drug concentration-time curve" or "AUC" reflects the actual body exposure to drug after administration of a dose of the drug and is expressed in mg*h/L. This area under the curve is measured from time 0 ($t_0$) to infinity (co) and is dependent on the rate of elimination of the drug from the body and the dose administered.

As used herein, the term "mean residence time" or "MRT" refers to the average length of time the drug remains in the body.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, swine, cows, bears, and so on.

As used herein, phrases such as "a subject that would benefit from therapy" and "an animal in need of treatment" refers to a subset of subjects, from amongst all prospective subjects, which would benefit from administration of a given therapeutic agent, e.g., a binding molecule such as an antibody, comprising one or more antigen-binding domains. Such binding molecules, e.g., antibodies, can be used, e.g., for a diagnostic procedures and/or for treatment or prevention of a disease.

IgM or IgM-Like Antibodies

IgM is the first immunoglobulin produced by B cells in response to stimulation by antigen and is naturally present at around 1.5 mg/ml in serum with a half-life of about 5 days. IgM is a pentameric or hexameric molecule and thus includes five or six binding units. An IgM binding unit typically includes two light and two heavy chains. While an IgG heavy chain constant region contains three heavy chain constant domains (CHL CH2 and CH3), the heavy ($\beta$) constant region of IgM additionally contains a fourth constant domain (CH4) and includes a C-terminal "tailpiece." The human IgM constant region typically comprises the amino acid sequence SEQ ID NO: 12 (identical to, e.g., GenBank Accession Nos. pir‖S37768, CAA47708.1, and . CAA47714.1). The human C$\mu$l region ranges from about amino acid 5 to about amino acid 102 of SEQ ID NO: 12; the human C$\mu$2 region ranges from about amino acid 114 to about amino acid 205 of SEQ ID NO: 12, the human C$\mu$3 region ranges from about amino acid 224 to about amino acid 319 of SEQ ID NO: 12, the C$\mu$4 region ranges from about amino acid 329 to about amino acid 430 of SEQ ID NO: 12, and the tailpiece ranges from about amino acid 431 to about amino acid 453 of SEQ ID NO: 12. SEQ ID NO: 12 is presented below.

```
SEQ ID NO: 12:
GSASAPTLFPLVSCENSPSDTSSVAVGCLAQDFLPDSITFSWKYKNNSDIS

STRGFPSVLRGGKYAATSQVLLPSKDVMQGTDEHVVCKVQHPNGNKEKNVP

LPVIAELPPKVSVFVPPRDGFFGNPRKSKLICQATGFSPRQIQVSWLREGK

QVGSGVTTDQVQAEAKESGPTTYKVTSTLTIKESDWLSQSMFTCRVDHRGL

TFQQNASSMCVPDQDTAIRVFAIPPSFASIFLTKSTKLTCLVTDLTTYDSV

TISWTRQNGEAVKTHTNISESHPNATFSAVGEASICEDDWNSGERFTCTVT

HTDLPSPLKQTISRPKGVALHRPDVYLLPPAREQLNLRESATITCLVTGFS

PADVFVQWMQRGQPLSPEKYVTSAPMPEPQAPGRYFAHSILTVSEEEWNTG

ETYTCVVAHEALPNRVTERTVDKSTGKPTLYNVSLVMSDTAGTCY
```

Other forms of the human IgM constant region with minor sequence variations exist, including, without limitation, GenBank Accession Nos. P01871.4, CAB37838.1, and pir‖HM The amino acid substitutions, insertions, and/or deletions at positions corresponding to SEQ ID NO: 12 described and claimed elsewhere in this disclosure can likewise be incorporated into alternate human IgM sequences, as well as into IgM constant region amino acid sequences of other species, e.g., those shown in FIG. 1.

Each IgM heavy chain constant region can be associated with an antigen-binding domain, e.g., a scFv or VHH, or a subunit of an antigen-binding domain, e.g., a VH region.

Five IgM binding units can form a complex with an additional small polypeptide chain (the J-chain) to form a pentameric IgM antibody or IgM-like antibody. The precursor form of the human J-chain, SEQ ID NO: 1, is presented below. The signal peptide (underlined) extends from amino acid 1 to about amino acid 22 of SEQ ID NO: 1, and the mature human J-chain extends from about amino acid 23 to amino acid 159 of SEQ ID NO: 1. The mature human J-chain includes the amino acid sequence SEQ ID NO: 2.

```
SEQ ID NO: 1:
MKNHLLFWGVLAVFIKAVHVKAQEDERIVLVDNKCKCARITSRIIRSSEDP

NEDIVERNIRIIVPLNNRENISDPTSPLRTRFVYHLSDLCKKCDPTEVELD

NQIVTATQSNICDEDSATETCYTYDRNKCYTAVVPLVYGGETKMVETALTP

DACYPD
```

SEQ ID NO: 2 is presented below.

```
SEQ ID NO: 2:
QEDERIVLVDNKCKCARITSRIIRSSEDPNEDIVERNIRIIVPLNNRENIS

DPTSPLRTRFVYHLSDLCKKCDPTEVELDNQIVTATQSNICDEDSATETCY

TYDRNKCYTAVVPLVYGGETKMVETALTPDACYPD
```

Without the J-chain, an IgM antibody or IgM-like antibody typically assembles into a hexamer, comprising up to twelve antigen-binding domains. With a J-chain, an IgM antibody or IgM-like antibody typically assembles into a pentamer, comprising up to ten antigen-binding domains, or more, if the J-chain is a modified J-chain comprising heterologous polypeptides comprising additional antigen-binding domain(s). The assembly of five or six IgM binding units into a pentameric or hexameric IgM antibody or IgM-like antibody is thought to involve the C$\mu$4 and tailpiece domains. See, e.g., Braathen, R., et al., *J. Biol. Chem.* 277:42755-42762 (2002). Accordingly, a pentameric or hexameric IgM antibody provided in this disclosure typically includes at least the CO and/or tailpiece domains (also referred to herein collectively as C$\mu$4-tp). A "multimerizing fragment" of an IgM heavy chain constant region thus includes at least the C$\mu$4-tp domains. An IgM heavy chain constant region can additionally include a CO domain or a fragment thereof, a C$\mu$2 domain or a fragment thereof, a C$\mu$l domain or a fragment thereof, and/or other IgM heavy chain domains. In certain aspects, a binding molecule, e.g., an IgM antibody or IgM-like antibody as provided herein can include a complete IgM heavy ($\mu$) chain constant domain, e.g., SEQ ID NO: 12, or a variant, derivative, or analog thereof.

In certain aspects, the disclosure provides a pentameric IgM or IgM-like antibody comprising five bivalent binding units, where each binding unit includes two IgM heavy chain constant regions or multimerizing fragments or variants thereof, each associated with an antigen-binding domain or subunit thereof. In certain aspects, the two IgM heavy chain constant regions are human heavy chain constant regions.

Where the IgM or IgM-like antibody provided herein is pentameric, the IgM or IgM-like antibody typically further comprises a J-chain, or functional fragment or variant thereof. In certain aspects the J-chain is a modified J-chain or variant thereof that further comprises one or more heterologous moieties attached thereto, as described elsewhere herein. In certain aspects the J-chain can be mutated to affect, e.g., enhance, the serum half-life of the IgM or IgM-like antibody provided herein, as discussed elsewhere herein.

An IgM heavy chain constant region can include one or more of a Cμ1 domain or fragment or variant thereof, a Cμ2 domain or fragment or variant thereof, a Cμ3 domain or fragment or variant thereof, and/or a Cμ4 domain or fragment or variant thereof, provided that the constant region can serve a desired function in the an IgM or IgM-like antibody, e.g., associate with second IgM constant region to form an antigen-binding domain, and/or associate with other binding units (and in the case of a pentamer, a J-chain) to form a hexamer or a pentamer. In certain aspects the two IgM heavy chain constant regions or fragments or variants thereof within an individual binding unit each comprise a Cμ4 domain or fragment or variant thereof, a tailpiece (tp) or fragment or variant thereof, or a combination of a Cμ4 domain and a TP or fragment or variant thereof. In certain aspects the two IgM heavy chain constant regions or fragments or variants thereof within an individual binding unit each further comprise a Cμ3 domain or fragment or variant thereof, a Cμ2 domain or fragment or variant thereof, a Cμ1 domain or fragment or variant thereof, or any combination thereof.

Modified J-Chains

In certain aspects, the J-chain of a pentameric an IgM or IgM-like antibody as provided herein can be modified, e.g., by introduction of a heterologous moiety, or two or more heterologous moieties, e.g., polypeptides, without interfering with the ability of the IgM or IgM-like antibody to assemble and bind to its binding target(s). See U.S. Pat. No. 9,951,134, PCT Publication No. WO 2017/059387, and PCT Publication No. WO 2017/059380, each of which is incorporated herein by reference in its entirety. Accordingly, IgM or IgM-like antibodies as provided herein, including multispecific IgM or IgM-like antibodies as described elsewhere herein, can comprise a modified J-chain or functional fragment or variant thereof comprising a heterologous moiety, e.g., a heterologous polypeptide, introduced into the J-chain or fragment or variant thereof. In certain aspects, a heterologous moiety can be a peptide or polypeptide sequence fused in frame to the J-chain or chemically conjugated to the J-chain or fragment or variant thereof, where the heterologous polypeptide is directly or indirectly fused to the variant J-chain or functional fragment thereof. In certain aspects, the heterologous polypeptide is fused to the J-chain or functional fragment thereof via a peptide linker, e.g., a peptide linker consisting of least 5 amino acids, but no more than 25 amino acids. In certain aspects, the peptide linker consists of GGGGS (SEQ ID NO: 25), GGGGSGGGGS (SEQ ID NO: 26), GGGGSGGGGSGGGGS (SEQ ID NO:27), GGGGSGGGGSGGGGSGGGGS (SEQ ID NO: 28), or GGGGSGGGGSGGGGSGGGGSGGGGS (SEQ ID NO: 29). In certain aspects the heterologous moiety can be a chemical moiety conjugated to the J-chain. Heterologous moieties to be attached to a J-chain can include, without limitation, a binding moiety, e.g., an antibody or antigen-binding fragment thereof, e.g., a single chain Fv (ScFv)

molecule, a stabilizing peptide that can increase the half-life of the IgM or IgM-like antibody, or a chemical moiety such as a polymer or a cytotoxin.

In some embodiments, a modified J-chain can comprise an antigen-binding domain that can include without limitation a polypeptide (including small peptides) capable of specifically binding to a target antigen. In certain aspects, an antigen-binding domain associated with a modified J-chain can be an antibody or an antigen-binding fragment thereof, as described elsewhere herein. In certain aspects, the antigen-binding domain can be a scFv antigen-binding domain or a single-chain antigen-binding domain derived, e.g., from a camelid or condricthoid antibody. The antigen-binding domain can be introduced into the J-chain at any location that allows the binding of the antigen-binding domain to its binding target without interfering with J-chain function or the function of an associated IgM or IgA antibody. Insertion locations include but are not limited to at or near the C-terminus, at or near the N-terminus or at an internal location that, based on the three-dimensional structure of the J-chain, is accessible. In certain aspects, the antigen-binding domain can be introduced into the mature human J-chain of SEQ ID NO: 2 between cysteine residues 92 and 101 of SEQ ID NO: 2. In a further aspect, the antigen-binding domain can be introduced into the human J-chain of SEQ ID NO: 2 at or near a glycosylation site. In a further aspect, the antigen-binding domain can be introduced into the human J-chain of SEQ ID NO: 2 within about 10 amino acid residues from the C-terminus, or within about 10 amino acids from the N-terminus.

Pentameric IgM or IgM-Like Antibodies with J-Chain Mutations that Alter Serum Half-Life This disclosure provides an IgM antibody or multimerizing fragment thereof, e.g., a pentameric IgM-like antibody, or a multimerizing fragment thereof, with enhanced serum half-life. In certain aspects, the IgM or IgM-like antibody provided herein comprises five bivalent antibody binding units or variants or multimerizing fragments thereof and a variant of a J-chain or functional fragment thereof. By a "functional fragment" of a J-chain is meant a J-chain fragment (or a fragment of a variant J-chain or a modified J-chain as provided herein) that remains capable of associating with five IgM binding units to form a pentamer or associating with two IgA binding units to form a dimer. Each binding unit of the provided IgM antibody or IgM-like antibody comprises two IgM heavy chain constant regions or fragments or variants thereof (where the fragments or variants are capable of multimerization), where each constant region is associated with an antigen-binding domain or subunit thereof. As provided herein, a "variant J-chain or functional fragment thereof" can include one or more single amino acid substitutions, deletions, or insertions relative to reference J-chain or functional fragment thereof, where the reference J-chain is identical to the variant J-chain except for the one or more single amino acid substitutions, deletions, or insertions. In certain aspects the reference J-chain is a wild-type J-chain. A variant J-chain or functional fragment thereof as provided herein can affect, e.g., enhance, the serum half-life of an IgM antibody or IgM-like antibody comprising the variant J-chain or functional fragment thereof. A variant J-chain or functional fragment thereof as provided herein can likewise affect, e.g., inhibit, the ability of an IgM antibody or IgM-like antibody comprising the variant J-chain or functional fragment thereof to bind to a cognate receptor, e.g., a Fcαμ receptor (FcαμR) or a polymeric Ig receptor (pIgR). The term "one or more single amino acid substitutions, insertions, and deletions" means that each amino acid of the variant J-chain or functional fragment thereof amino acid sequence can individually be substituted, deleted, or can have a single amino acid inserted adjacent thereto relative to the reference J-chain, but the variant J-chain or functional fragment thereof must still be able to serve the function of assembling with IgM heavy chains or IgM-like heavy chains and antibody light chains to form an IgM pentamer or IgM-like pentamer.

In certain aspects the variant J-chain or functional fragment thereof as provided herein can have a single amino acid substitution, insertion or deletion, a combination of two single amino acid substitutions, insertions, or deletions (e.g., two single amino acid substitutions or one single amino acid substitution and one single amino acid insertion or deletion), a combination of three single amino acid substitutions, insertions, or deletions, a combination of four single amino acid substitutions, insertions, or deletions or more, where the one, two, three, four, or more single amino acid substitutions, insertions or deletions can affect, e.g., enhance, the serum half-life of an IgM antibody or IgM-like antibody comprising the variant J-chain or functional fragment thereof. Accordingly, a provided IgM or IgM-like antibody can exhibit an increased serum half-life upon administration to a subject animal, e.g., a mouse model, relative to a reference IgM or IgM-like antibody that is identical, except for the one or more single amino acid substitutions, deletions, or insertions in the variant J-chain or functional fragment thereof, where both the provided antibody and the reference antibody are administered in the same way to the same animal species.

In certain aspects, the serum half-life of the provided IgM or IgM-like antibody comprising the variant J-chain, e.g., the a half-life ($t_{1/2}\alpha$), the β half-life ($t_{1/2}\beta$), both the $t_{1/2}\alpha$ and the $t_{1/2}\beta$, or the overall half-life, can be increased by at least 0.1-fold, at least 0.5-fold, at least 1-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 500-fold, at least 1000-fold or more over the reference antibody. In certain aspects, the increase in serum half-life approaches that of an IgG antibody comprising the same antigen-binding domains.

In certain aspects, an IgM antibody or IgM-like antibody comprising a variant J-chain as provided herein further exhibits other modified pharmacokinetic parameters, e.g., an increased peak plasma concentration ($C_{max}$), an increased area under the curve from To to co (AUC), e.g., a modified clearance time, an increased mean residence time (MRT) or any combination thereof relative to the reference antibody. In certain aspects the AUC can be increased by at least 0.1-fold, at least 0.5-fold, at least 1-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 500-fold, at least 1000-fold or more over a reference IgM or IgM-like antibody that is identical, except for the one or more single amino acid substitutions, deletions, or insertions in the variant J-chain or functional fragment thereof, where both the provided antibody and the reference antibody are administered in the same way to the same animal species.

In certain aspects, the J-chain of the IgM antibody or IgM-like antibody as provided herein comprises an amino acid substitution at the amino acid position corresponding to amino acid Y102 of the mature wild-type human J-chain (SEQ ID NO: 2). By "an amino acid corresponding to amino acid Y102 of the mature wild-type human J-chain" is meant the amino acid in the sequence of the J-chain of any species which is homologous to Y102 in the human J-chain. The position corresponding to Y102 in SEQ ID NO: 2 is conserved in the J-chain amino acid sequences of at least 43 other species. See FIG. 4 of U.S. Pat. No. 9,951,134, which is incorporated by reference herein. As demonstrated in the Examples, certain mutations at the position corresponding to Y102 of SEQ ID NO: 2 can inhibit the binding of certain immunoglobulin receptors, e.g., the human or murine Fcαμ receptor, the murine Fcμ receptor, and/or the human or murine polymeric Ig receptor (pIg receptor) to an IgM pentamer comprising the mutant J-chain. See, e.g., FIG. 2. In certain aspects, the amino acid corresponding to Y102 of SEQ ID NO: 2 can be substituted with any amino acid. In certain aspects, the amino acid corresponding to Y102 of SEQ ID NO: 2 can be substituted with alanine (A), serine (S) or arginine (R). In a particular aspect, the amino acid corresponding to Y102 of SEQ ID NO: 2 can be substituted with alanine. In a particular aspect the J-chain or functional fragment or variant thereof is a variant human J-chain and comprises the amino acid sequence SEQ ID NO: 3. SEQ ID NO: 3 is presented below.

```
SEQ ID NO: 3:
QEDERIVLVDNKCKCARITSRIIRSSEDPNEDIVERNIRIIVPLNNRENIS

DPTSPLRTRFVYHLSDLCKKCDPTEVELDNQIVTATQSNICDEDSATETCA

TYDRNKCYTAVVPLVYGGETKMVETALTPDACYPD
```

In a particular aspect, the amino acid corresponding to Y102 of SEQ ID NO: 2 can be substituted with serine. In a particular aspect the J-chain or functional fragment or variant thereof is a variant human J-chain and comprises the amino acid sequence SEQ ID NO: 4. SEQ ID NO: 4 is presented below.

```
                                    SEQ ID NO: 4
QEDERIVLVDNKCKCARITSRIIRSSEDPNEDIVERNIRIIVPLNNRENIS

DPTSPLRTRFVYHLSDLCKKCDPTEVELDNQIVTATQSNICDEDSATETCS

TYDRNKCYTAVVPLVYGGETKMVETALTPDACYPD
```

In a particular aspect, the amino acid corresponding to Y102 of SEQ ID NO: 2 can be substituted with arginine. In a particular aspect the J-chain or functional fragment or variant thereof is a variant human J-chain and comprises the amino acid sequence SEQ ID NO: 5. SEQ ID NO: 5 is presented below.

```
                                    SEQ ID NO: 5
QEDERIVLVDNKCKCARITSRIIRSSEDPNEDIVERNIRIIVPLNNRENIS

DPTSPLRTRFVYHLSDLCKKCDPTEVELDNQIVTATQSNICDEDSATETCR

TYDRNKCYTAVVPLVYGGETKMVETALTPDACYPD
```

In certain aspects, the J-chain of the IgM antibody or IgM-like antibody as provided herein comprises an amino acid substitution at the amino acid position corresponding to amino acid T103 of the wild-type mature human J-chain (SEQ ID NO: 2). By "an amino acid corresponding to amino acid T103 of the wild-type mature human J-chain" is meant the amino acid in the sequence of the J-chain of any species which is homologous to T103 in the human J-chain. The position corresponding to T103 in SEQ ID NO: 2 is conserved in the J-chain amino acid sequences of at least 37 other species. See FIG. 4 of U.S. Pat. No. 9,951,134, which is incorporated by reference herein. As demonstrated in the Examples, certain mutations at the position corresponding to T103 in SEQ ID NO: 2 can inhibit the binding of the human Fcαμ receptor to an IgM pentamer comprising the mutant J-chain. See FIG. 2. In certain aspects, the amino acid corresponding to T103 of SEQ ID NO: 2 can be substituted with any amino acid. In a particular aspect, the amino acid corresponding to T103 of SEQ ID NO: 2 can be substituted with alanine. In a particular aspect the J-chain or functional fragment or variant thereof is a variant human J-chain and comprises the amino acid sequence SEQ ID NO: 6. SEQ ID NO: 6 is presented below.

```
SEQ ID NO: 6:
QEDERIVLVDNKCKCARITSRIIRSSEDPNEDIVERNIRIIV

PLNNRENISDPTSPLRTRFVYHLSDLCKKCDPTEVELDN

QIVTATQSNICDEDSATETCYAYDRNKCYTAVVPLVYG

GETKMVETALTPDACYPD
```

In certain aspects, the variant J-chain or functional fragment thereof of the IgM antibody or IgM-like antibody as provided herein comprises an amino acid substitution at the amino acid position corresponding to amino acid N49 or amino acid S51 of the mature wild-type human J-chain (SEQ ID NO: 2), provided that S51 is not substituted with threonine (T), or wherein the J-chain comprises amino acid substitutions at the amino acid positions corresponding to both amino acids N49 and S51 of the wild-type mature human J-chain (SEQ ID NO: 2). Again, by "an amino acid corresponding to amino acid N49 of SEQ ID NO: 2 or an amino acid corresponding to S51 of SEQ ID NO: 2 of the wild-type mature human J-chain" is meant the amino acid in the sequence of the J-chain of any species which is homologous to N49 and/or S51 in the human J-chain. The positions corresponding to N49 and S51 in SEQ ID NO: 2 are conserved in the J-chain amino acid sequences of at least 43 other species. See FIG. 4 of U.S. Pat. No. 9,951,134, which is incorporated by reference herein. The amino acids corresponding to N49 and S51 of SEQ ID NO: 2 along with the amino acid corresponding to ISO of SEQ ID NO: 2 comprise an N-linked glycosylation motif in the J-chain. Accordingly, mutations at N49 and/or S51 (with the exception of a single threonine substitution at S51) can prevent glycosylation at this motif. In certain aspects, the asparagine at the position corresponding to N49 of SEQ ID NO: 2 can be substituted with any amino acid. In certain aspects, the asparagine at the position corresponding to N49 of SEQ ID NO: 2 can be substituted with alanine (A), glycine (G), threonine (T), serine (S) or aspartic acid (D). In a particular aspect the position corresponding to N49 of SEQ ID NO: 2 can be substituted with alanine (A). In a particular aspect the J-chain is a variant human J-chain and comprises the amino acid sequence SEQ ID NO: 7. SEQ ID NO: 7 is presented below.

```
SEQ ID NO: 7:
QEDERIVLVDNKCKCARITSRIIRSSEDPNEDIVERNIRIIV

PLNNREAISDPTSPLRTRFVYHLSDLCKKCDPTEVELDN

QIVTATQSNICDEDSATETCYTYDRNKCYTAVVPLVYG

GETKMVETALTPDACYPD
```

In certain aspects, the serine at the position corresponding to S51 of SEQ ID NO: 2 can be substituted with any amino acid except threonine. In certain aspects, the serine at the position corresponding to S51 of SEQ ID NO: 2 can be substituted with alanine (A) or glycine (G). In a particular aspect the position corresponding to S51 of SEQ ID NO: 2 can be substituted with alanine (A). In a particular aspect the variant J-chain or functional fragment thereof is a variant human J-chain and comprises the amino acid sequence SEQ ID NO: 8. SEQ ID NO: 8 is presented below.

```
SEQ ID NO: 8:
QEDERIVLVDNKCKCARITSRIIRSSEDPNEDIVERNIRIIV

PLNNRENIADPTSPLRTRFVYHLSDLCKKCDPTEVELDN

QIVTATQSNICDEDSATETCYTYDRNKCYTAVVPLVYG

GETKMVETALTPDACYPD
```

In certain aspects, the variant J-chain or functional fragment thereof of the provided IgM antibody or IgM-like antibody as provided herein is a modified J-chain, e.g., as provided in U.S. Pat. No. 9,951,134. In certain aspects the modified J-chain further comprises a heterologous polypeptide, where the heterologous polypeptide is directly or indirectly fused to the variant J-chain or functional fragment thereof. In certain aspects, the heterologous polypeptide is fused to the variant J-chain or functional fragment thereof via a peptide linker, e.g., a peptide linker consisting of least 5 amino acids, but no more than 25 amino acids. In certain aspects, the peptide linker consists of GGGGS (SEQ ID NO: 25), GGGGSGGGGS (SEQ ID NO: 26), GGGGSGGGGSGGGGS (SEQ ID NO:27), GGGGSGGGGSGGGGSGGGGS (SEQ ID NO: 28), or GGGGSGGGGSGGGGSGGGGSGGGGS (SEQ ID NO: 29). The heterologous polypeptide can be fused to the N-terminus of the variant J-chain or functional fragment thereof, the C-terminus of the variant J-chain or functional fragment thereof, heterologous polypeptides can be fused to both the N-terminus and C-terminus of the variant J-chain or functional fragment thereof. In certain aspects, the heterologous polypeptide comprises an antigen-binding domain. In certain aspects, the binding domain of the heterologous polypeptide is an antibody or antigen-binding fragment thereof, e.g., a Fab fragment, a Fab' fragment, a F(ab')2 fragment, a Fd fragment, a Fv fragment, a single-chain Fv (scFv) fragment, a disulfide-linked Fv (sdFv) fragment, or any combination thereof. In certain aspects, the heterologous polypeptide can specifically bind to CD3ε, for example, the modified variant J-chain or functional fragment thereof that can increase serum half-life of the provided IgM or IgM-like antibody is a variant of the modified J-chain "V15J" (SEQ ID NO: 9) and can comprise, e.g., the amino acid sequence SEQ ID NO: 10 (V15J-Y102A), or SEQ ID NO: 23 (V15J-T103A), or SEQ ID NO: 24 (V15J-N49A). In certain aspects, the modified J-chain can comprise a heterologous polypeptide fused to the N-terminus of the J-chain, e.g., a scFv antibody fragment, that specifically binds to CD3ε, and can further comprise an additional heterologous polypeptide that affects serum half-life of an IgM antibody comprising the modified J-chain fused to the C-terminus of the J-chain, e.g., human serum albumin. In a specific aspect the modified J-chain comprises the amino acid sequence SEQ ID NO: 11 (VJH) or a variant thereof with one or more amino acid substitutions, insertions, or deletions that can affect serum half-life of a pentameric IgM antibody or IgM-like antibody comprising the J-chain, e.g., at a position corresponding to Y102 or T103 of SEQ ID NO: 2.

In certain aspects, an IgM or IgM-like antibody as provided herein comprises a variant J-chain or functional fragment thereof as provided herein comprising the amino acid sequence SEQ ID NO: 3, SEQ ID NO: 4, SEQ ID NO: 5, SEQ ID NO: 6, SEQ ID NO: 7, SEQ ID NO: 8, SEQ ID NO: 10, SEQ ID NO: 23, SEQ ID NO: 24, or any combination thereof.

In certain aspects, an IgM or IgM-like antibody comprising a variant J-chain as provided herein further comprises variant IgM heavy chain constant regions comprising one or more single amino acid substitutions, deletions, or insertions relative to a reference IgM heavy chain constant region identical to the variant IgM heavy chain constant regions except for the one or more single amino acid substitutions, deletions, or insertions, where the variant IgM heavy chain constant regions can likewise affect the serum half-life of the provided IgM antibody or IgM-like antibody. Such an IgM antibody or IgM-like antibody can, in certain aspects, exhibit a further increased serum half-life upon administration to an animal relative to a reference IgM antibody or IgM-like antibody that is identical except for the one or more single amino acid substitutions, deletions, or insertions in IgM heavy chain constant regions, and is administered in the same way to the same animal species. According to this aspect, the reference IgM antibody or IgM-like antibody can be an IgM antibody or IgM-like antibody comprising a variant J-chain as provided herein, e.g., a variant J-chain comprising the amino acid sequence SEQ ID NO: 3, SEQ ID NO: 4, SEQ ID NO: 5, SEQ ID NO: 6, SEQ ID NO: 7, SEQ ID NO: 8, SEQ ID NO: 10, SEQ ID NO: 23, SEQ ID NO: 24, or any combination thereof. In certain aspects the increased serum half-life can be additive, or greater than additive, or less than additive. Exemplary variant IgM heavy chain constant regions are provided elsewhere herein and include without limitation variant human IgM heavy chain constant regions comprising the amino acid sequence SEQ ID NO: 13, SEQ ID NO: 14, SEQ ID NO: 31, SEQ ID NO: 32, or SEQ ID NO: 34.

In certain aspects, the serum half-life of the IgM or IgM-like antibody comprising a variant J-chain as provided herein and variant IgM heavy chain constant regions as provided herein comprises an increase in serum half-life over a reference antibody comprising just the variant J-chain or just the variant IgM constant regions that is additive of the individual increases in serum half-life, is greater than additive, or is less than additive.

J-Chain Variants that Affect IgM Serum Half-Life

This disclosure provides an isolated variant J-chain or functional fragment thereof that, as part of a pentameric IgM antibody or a pentameric IgM-like antibody, can increase the serum half-life of that antibody. The provided variant J-chain or functional fragment thereof can be of any species and comprises one or more single amino acid substitutions, deletions, or insertions relative to a reference J-chain identical to the variant J-chain except for the one or more single amino acid substitutions, insertions, or deletions. The term "one or more single amino acid substitutions, insertions, and deletions" means that each amino acid of the variant J-chain amino acid sequence can individually be substituted, deleted, or can have a single amino acid inserted adjacent thereto, but the variant J-chain or functional fragment thereof must still be able to serve the function of assembling with IgM heavy chains or IgM-like heavy chains and antibody light chains to form an IgM pentamer or IgM-like pentamer. In certain aspects the variant J-chain or functional fragment thereof as provided herein can have a single amino acid substitution, insertion or deletion, a combination of two single amino acid substitutions, insertions, or deletions (e.g., two single amino acid substitutions or one single amino acid substitution and one single amino acid insertion or deletion), a combination of three single amino acid substitutions, insertions, or deletions, a combination of four single amino acid substitutions, insertions, or deletions or more, where the one, two, three, four, or more single amino acid substitutions, insertions or deletions can individually or collectively affect the serum half-life of an IgM antibody or IgM-like antibody comprising the variant J-chain or functional fragment thereof. In certain aspects, the one or more single amino acid substitutions, insertions, or deletions inhibit an IgM antibody or IgM-like antibody comprising the variant J-chain from interacting, e.g., binding to a receptor, e.g., a FcapR or a pIgR.

In certain aspects, the serum half-life, e.g., the a half-life, the β half-life, or the overall half-life, of an IgM or IgM-like antibody comprising the provided variant J-chain or functional fragment thereof as provided herein can be increased by at least 0.1-fold, at least 0.5-fold, at least 1-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 500-fold, at least 1000-fold or more over the reference antibody. In certain aspects, the increase in serum half-life approaches that of an IgG antibody comprising the same antigen-binding domains.

In certain aspects, an IgM antibody or IgM-like antibody comprising a provided variant J-chain further exhibits other modified pharmacokinetic parameters, e.g., an increased peak plasma concentration ($C_{max}$), an increased area under the curve from To to ∞ (AUC), a modified clearance time, an increased mean residence time (MRT) or any combination thereof relative to the reference antibody. In certain aspects the AUC can be increased by at least 0.1-fold, at least 0.5-fold, at least 1-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 500-fold, at least 1000-fold or more over a reference IgM or IgM-like antibody that is identical, except for the one or more single amino acid substitutions, deletions, or insertions in the variant J-chain or functional fragment thereof, where both the provided antibody and the reference antibody are administered in the same way to the same animal species.

In certain aspects, the isolated variant J-chain or functional fragment thereof as provided herein comprises an amino acid substitution at the amino acid position corresponding to amino acid Y102 of the mature wild-type human J-chain (SEQ ID NO: 2). By "an amino acid corresponding to amino acid Y102 of the mature wild-type human J-chain" is meant the amino acid in the sequence of the J-chain of any species which is homologous to Y102 in the human J-chain. The position corresponding to Y102 in SEQ ID NO: 2 is conserved in the J-chain amino acid sequences of at least 43 other species. See FIG. 4 of U.S. Pat. No. 9,951,134, which is incorporated by reference herein. As described in the Examples below, certain amino acid substitutions at the position corresponding to Y102 of SEQ ID NO: 2 inhibit the variant J-chain from binding to the Fc alpha-mu (Fcαμ) receptor and to the polymeric Ig receptor (pIg receptor or pIgR). In certain aspects, the amino acid corresponding to Y102 of SEQ ID NO: 2 can be substituted with any amino acid. In certain aspects, the amino acid corresponding to Y102 of SEQ ID NO: 2 can be substituted with alanine (A), serine (S) or arginine (R). In a particular aspect, Y102 of SEQ ID NO: 2 can be substituted with alanine. In a particular aspect the variant J-chain or functional fragment thereof is a variant human J-chain and comprises the amino acid sequence SEQ ID NO: 3. In a particular aspect, the amino acid corresponding to Y102 of SEQ ID NO: 2 can be substituted with serine. In a particular aspect the variant J-chain or functional fragment thereof is a variant human J-chain and comprises the amino acid sequence SEQ ID NO: 4. In a particular aspect, the amino acid corresponding to Y102 of SEQ ID NO: 2 can be substituted with arginine. In a particular aspect the variant J-chain or functional fragment thereof is a variant human J-chain and comprises the amino acid sequence SEQ ID NO: 5.

In certain aspects, the isolated variant J-chain or functional fragment thereof as provided herein comprises an amino acid substitution at the amino acid position corresponding to amino acid T103 of the mature wild-type human J-chain (SEQ ID NO: 2). By "an amino acid corresponding to amino acid T103 of the mature wild-type human J-chain" is meant the amino acid in the sequence of the J-chain of any species which is homologous to T103 in the human J-chain. The position corresponding to T103 in SEQ ID NO: 2 is conserved in the J-chain amino acid sequences of at least 37 other species. See FIG. 4 of U.S. Pat. No. 9,951,134, which is incorporated by reference herein. As described in the Examples below, amino acid substitutions at the position corresponding to T103 of SEQ ID NO: 2 inhibit the variant J-chain from binding to the immunoglobulin Fcαμ receptor. In certain aspects, the amino acid corresponding to T103 of SEQ ID NO: 2 can be substituted with any amino acid. In certain aspects, the amino acid corresponding to T103 of SEQ ID NO: 2 can be substituted with alanine (A). In a particular aspect the variant J-chain or functional fragment thereof is a variant human J-chain and comprises the amino acid sequence SEQ ID NO: 6.

In certain aspects, this disclosure provides an isolated variant J-chain or functional fragment thereof comprises an amino acid substitution at the amino acid position corresponding to amino acid N49 or amino acid S51 of the mature human J-chain (SEQ ID NO: 2), provided that S51 is not substituted with threonine (T) or wherein the J-chain comprises amino acid substitutions at the amino acid positions corresponding to both amino acids N49 and S51 of the mature wild-type human J-chain (SEQ ID NO: 2). Again, by "an amino acid corresponding to amino acid N49 of SEQ ID NO: 2 of an amino acid corresponding to S51 of SEQ ID NO: 2 of the wild-type human J-chain" is meant the amino acid in the sequence of the J-chain of any species which is homologous to N49 and/or S51 in the human J-chain. The positions corresponding to N49 and S51 in SEQ ID NO: 2 are conserved in the J-chain amino acid sequences of at least 43 other species. See FIG. 4 of U.S. Pat. No. 9,951,134, which is incorporated herein by reference. The amino acids corresponding to N49 and S51 of SEQ ID NO: 2 along with the amino acid corresponding to 150 of SEQ ID NO: 2 comprise an N-linked glycosylation motif in the J-chain, and mutations at N49 and/or S51 (with the exception of a threonine substitution at S51) can thus prevent possible glycosylation at this motif. In certain aspects, the asparagine at the position corresponding to N49 of SEQ ID NO: 2 can be substituted with any amino acid. In certain aspects, the asparagine at the position corresponding to N49 of SEQ ID NO: 2 can be substituted with alanine (A), glycine (G), threonine (T), serine (S) or aspartic acid (D). In a particular aspect the position corresponding to N49 of SEQ ID NO: 2 can be substituted with alanine (A). In a particular aspect the variant J-chain or functional fragment thereof is a variant human J-chain and comprises the amino acid sequence SEQ ID NO: 7. In certain aspects, the serine at the position corresponding to S51 of SEQ ID NO: 2 can be substituted with any amino acid (except threonine). In certain aspects, the serine at the position corresponding to S51 of SEQ ID NO: 2 can be substituted with alanine (A) or glycine (G). In a particular aspect the position corresponding to S51 of SEQ ID NO: 2 can be substituted with alanine (A). In a particular aspect the variant J-chain or functional fragment thereof is a variant human J-chain and comprises the amino acid sequence SEQ ID NO: 8.

In certain aspects, the variant J-chain or functional fragment thereof as provided herein comprises the amino acid sequence SEQ ID NO: 3, SEQ ID NO: 4, SEQ ID NO: 5, SEQ ID NO: 6, SEQ ID NO: 7, SEQ ID NO: 8, SEQ ID NO: 10, SEQ ID NO: 23, SEQ ID NO: 24, or any combination thereof.

Variant IgM Constant Regions Conferring Increased Serum Half-Life

This disclosure further provides an IgM antibody or IgM-like antibody with enhanced serum half-life, where the IgM antibody or IgM-like antibody comprises five or six bivalent antibody binding units or variants or fragments thereof, wherein each binding unit comprises two variant IgM heavy chain constant regions or multimerizing fragments thereof, each associated with an antigen-binding domain or subunit thereof. The variant IgM heavy chain constant regions or multimerizing fragments thereof as provided each comprise one or more single amino acid substitutions, deletions, or insertions relative to a reference IgM heavy chain constant region identical to the variant IgM heavy chain constant regions except for the one or more single amino acid substitutions, deletions, or insertions. In certain aspects, the variant IgM heavy chain constant regions can affect, e.g., increase, serum half-life of the provided IgM antibody or IgM-like antibody either alone, or in combination with a variant J-chain, variant modified J-chain, or functional fragment thereof as provided elsewhere in this disclosure. By "a reference IgM heavy chain constant region" is meant an IgM heavy chain constant region that is identical to the variant IgM heavy chain constant region except for the one or more single amino acid substitutions, deletions, or insertions. In certain aspects, a variant IgM constant region or multimerizing fragment thereof, when expressed as part of either a pentameric or a hexameric IgM antibody or IgM-like antibody as provided herein confers increased serum half-life to the IgM antibody or IgM-like antibody when administered to a subject animal, relative to a reference IgM antibody or IgM-like antibody administered in the same way to the same animal, where the reference IgM antibody or IgM-like antibody is identical except for the one or more single amino acid substitutions, deletions, or insertions in the IgM heavy chain constant regions, and is administered in the same way to the same animal species. In certain aspects, the variant IgM constant region includes one or more amino acid substitutions, insertions, or deletions, e.g., in the Cμ4 domain, relative to the reference IgM constant region. Assays for measuring serum half-life are well known to those of ordinary skill in the art, and exemplary assays are described herein and in, e.g., in U.S.

Patent Appl. Publication No. US-2018-0265596-A1, which is incorporated herein by reference in its entirety.

In certain aspects, a variant IgM heavy chain constant region or multimerizing fragment thereof that confers increased serum half-life to an IgM antibody or IgM-like antibody as provided herein can further increase the serum half-life of a provided pentameric IgM antibody or IgM-like antibody with a variant J-chain that likewise increases the serum half-life of the IgM antibody or IgM-like antibody, such as the variant J-chains provided elsewhere herein. In certain aspects the increase in serum half-life is additive. In certain aspects the increase in serum half-life is greater than additive or less than additive.

As provided herein, a variant IgM constant region or multimerizing fragment thereof can include one or more single amino acid substitutions, deletions, or insertions that affect serum half-life of an IgM antibody or IgM-like antibody comprising the variant IgM constant region or fragment. The term "one or more single amino acid substitutions, insertions, and deletions" means that each amino acid of the variant IgM constant region or multimerizing fragment thereof can individually be substituted, deleted, or can have a single amino acid inserted adjacent thereto, but the variant IgM constant region or multimerizing fragment thereof must still be able to serve the function within an IgM or IgM-like binding molecule, e.g., antibody, to form an IgM pentamer or hexamer or IgM-like pentamer or hexamer. In certain aspects the variant IgM constant region or multimerizing fragment thereof as provided herein can have a single amino acid substitution, insertion or deletion, a combination of two single amino acid substitutions, insertions, and/or deletions (e.g., two single amino acid substitutions or one single amino acid substitution and one single amino acid insertion or deletion), a combination of three single amino acid substitutions, insertions, and/or deletions, a combination of four single amino acid substitutions, insertions, and/or deletions or more, where the one, two, three, four, or more single amino acid substitutions, insertions and/or deletions can affect the serum half-life of an IgM antibody or IgM-like antibody comprising the variant IgM constant region or multimerizing fragment thereof. Accordingly, the provided IgM antibody or IgM-like antibody exhibits an increased serum half-life upon administration to an animal relative to a reference IgM antibody or IgM-like antibody that is identical, except for the one or more single amino acid substitutions, deletions, and/or insertions in the variant IgM constant region or multimerizing fragment thereof, where both the provided antibody and the reference antibody are administered in the same way to the same animal species.

In certain aspects, the serum half-life of the IgM or IgM-like antibody, e.g., the a half-life, the β half-life, or the overall half-life, can be increased by at least 0.1-fold, at least 0.5-fold, at least 1-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 500-fold, at least 1000-fold or more over the reference antibody. In certain aspects, the increase in serum half-life approaches that of an IgG antibody comprising the same antigen-binding domains. In certain aspects a variant IgM constant region or multimerizing fragment thereof can be combined with other IgM antibody or IgM-like antibody modifications to further increase serum half-life, e.g., a variant IgM constant region or multimerizing fragment thereof as provided herein can be combined with a J-chain comprising amino acid substitutions, deletions, and/or insertions as described elsewhere herein to provide an additive or greater than additive, e.g., synergistic, increase in serum half-life.

In certain aspects, an IgM antibody or IgM-like antibody comprising a variant IgM constant region or multimerizing fragment thereof as provided herein further exhibits other modified pharmacokinetic parameters, e.g., an increased peak plasma concentration ($C_{max}$), an increased area under the curve from To to co (AUC), a modified clearance time, an increased mean residence time (MRT) or any combination thereof relative to the reference antibody.

In certain aspects, a variant IgM constant region or multimerizing fragment thereof of an IgM antibody or IgM-like antibody as provided herein comprises an amino acid substitution at the amino acid position corresponding to amino acid S401 of the wild-type human IgM constant region (SEQ ID NO: 12), which in turn corresponds to amino acid S524 according to the Kabat numbering system. By "an amino acid corresponding to amino acid S401 of the wild-type human IgM constant region" is meant the amino acid in the sequence of the IgM constant region of any species which is homologous to S401 in the human IgM constant region. The position corresponding to S401 in SEQ ID NO: 12 is conserved in the IgM constant region amino acid sequences of some species, e.g., non-human primates, but not in other species, e.g., mouse. See FIG. 1. In certain aspects, S401 of SEQ ID NO: 12 can be substituted with any amino acid. In certain aspects, S401 of SEQ ID NO: 12 can be substituted with alanine (A). In a particular aspect the variant IgM constant region is a variant human IgM constant region comprising an S401A mutation, presented herein as SEQ ID NO: 13. SEQ ID NO: 13 is presented below, with the S401A mutation in bold underline:

```
SEQ ID NO: 13
GSASAPTLFPLVSCENSPSDTSSVAVGCLAQDFLPDSITFS

WKYKNNSDISSTRGFPSVLRGGKYAATSQVLLPSKDVM

QGTDEHVVCKVQHPNGNKEKNVPLPVIAELPPKVSVFV

PPRDGFFGNPRKSKLICQATGFSPRQIQVSWLREGKQVG

SGVTTDQVQAEAKESGPTTYKVTSTLTIKESDWLSQSMF

TCRVDHRGLTFQQNASSMCVPDQDTAIRVFAIPPSFASIF

LTKSTKLTCLVTDLTTYDSVTISWTRQNGEAVKTHTNIS

ESHPNATFSAVGEASICEDDWNSGERFTCTVTHTDLPSP

LKQTISRPKGVALHRPDVYLLPPAREQLNLRESATITCLV

TGFSPADVFVQWMQRGQPLSPEKYVTSAPMPEPQAPGR

YFAHSILTVAEEEWNTGETYTCVVAHEALPNRVTERTV

DKSTGKPTLYNVSLVMSDTAGTCY
```

In certain aspects, a variant IgM constant region or multimerizing fragment thereof of an IgM antibody or IgM-like antibody as provided herein comprises an amino acid substitution at the amino acid position corresponding to amino acid E402 of the wild-type human IgM constant region (SEQ ID NO: 12), which in turn corresponds to amino acid E525 according to the Kabat numbering system. By "an amino acid corresponding to amino acid E402 of the wild-type human IgM constant region" is meant the amino acid in the sequence of the IgM constant region of any species which is homologous to E402 in the human IgM constant region. The position corresponding to E402 in SEQ ID NO: 12 is conserved in the IgM constant region amino acid sequences of some species, e.g., non-human primates and mouse. See FIG. 1. In certain aspects, E402 of SEQ ID NO: 12 can be substituted with any amino acid. In certain aspects, E402 of SEQ ID NO: 12 can be substituted with alanine (A). In a particular aspect the variant IgM constant region is a variant human IgM constant region comprising an E402A mutation, presented herein as SEQ ID NO: 14. SEQ ID NO: 14 is presented below with the E402A mutation in bold underline:

```
SEQ ID NO: 14:
GSASAPTLFPLVSCENSPSDTSSVAVGCLAQDFLPDSITFS

WKYKNNSDISSTRGFPSVLRGGKYAATSQVLLPSKDVM

QGTDEHVVCKVQHPNGNKEKNVPLPVIAELPPKVSVFV

PPRDGFFGNPRKSKLICQATGFSPRQIQVSWLREGKQVG

SGVTTDQVQAEAKESGPTTYKVTSTLTIKESDWLSQSMF

TCRVDHRGLTFQQNASSMCVPDQDTAIRVFAIPPSFASIF

LTKSTKLTCLVTDLTTYDSVTISWTRQNGEAVKTHTNIS

ESHPNATFSAVGEASICEDDWNSGERFTCTVTHTDLPSP

LKQTISRPKGVALHRPDVYLLPPAREQLNLRESATITCLV

TGFSPADVFVQWMQRGQPLSPEKYVTSAPMPEPQAPGR

YFAHSILTVSAEEWNTGETYTCVVAHEALPNRVTERTV

DKSTGKPTLYNVSLVMSDTAGTCY
```

In certain aspects, a variant IgM constant region or multimerizing fragment thereof of an IgM antibody or IgM-like antibody as provided herein comprises an amino acid substitution at the amino acid position corresponding to amino acid E403 of the wild-type human IgM constant region (SEQ ID NO: 12), which in turn corresponds to amino acid E526 according to the Kabat numbering system. By "an amino acid corresponding to amino acid E403 of the wild-type human IgM constant region" is meant the amino acid in the sequence of the IgM constant region of any species which is homologous to E403 in the human IgM constant region. The position corresponding to E403 in SEQ ID NO: 12 is conserved in the IgM constant region amino acid sequences of some species, e.g., non-human primates and mouse. See FIG. 1. In certain aspects, E403 of SEQ ID NO: 12 can be substituted with any amino acid. In certain aspects, E403 of SEQ ID NO: 12 can be substituted with alanine (A). In a particular aspect the variant IgM constant region is a variant human IgM constant region comprising an E403A mutation, presented herein as SEQ ID NO: 34. SEQ ID NO: 34 is presented below with the E403A mutation in bold underline:

```
SEQ ID NO: 34:
GSASAPTLFPLVSCENSPSDTSSVAVGCLAQDFLPDSITFS

WKYKNNSDISSTRGFPSVLRGGKYAATSQVLLPSKDVM

QGTDEHVVCKVQHPNGNKEKNVPLPVIAELPPKVSVFV

PPRDGFFGNPRKSKLICQATGFSPRQIQVSWLREGKQVG

SGVTTDQVQAEAKESGPTTYKVTSTLTIKESDWLSQSMF

TCRVDHRGLTFQQNASSMCVPDQDTAIRVFAIPPSFASIF

LTKSTKLTCLVTDLTTYDSVTISWTRQNGEAVKTHTNIS
```

```
ESHPNATFSAVGEASICEDDWNSGERFTCTVTHTDLPSP

LKQTISRPKGVALHRPDVYLLPPAREQLNLRESATITCLV

TGFSPADVFVQWMQRGQPLSPEKYVTSAPMPEPQAPGR

YFAHSILTVSEAEWNTGETYTCVVAHEALPNRVTERTV

DKSTGKPTLYNVSLVMSDTAGTCY
```

In certain aspects, a variant IgM constant region or multimerizing fragment thereof of an IgM antibody or IgM-like antibody as provided herein comprises an amino acid substitution at the amino acid position corresponding to amino acid R344 of the wild-type human IgM constant region (SEQ ID NO: 12), which in turn corresponds to amino acid R467 according to the Kabat numbering system. By "an amino acid corresponding to amino acid R344 of the wild-type human IgM constant region" is meant the amino acid in the sequence of the IgM constant region of any species which is homologous to R344 in the human IgM constant region. The position corresponding to R344 in SEQ ID NO: 12 is conserved in the IgM constant region amino acid sequences of some species, e.g., non-human primates and mouse. See FIG. 1. In certain aspects, R344 of SEQ ID NO: 12 can be substituted with any amino acid. In certain aspects, R344 of SEQ ID NO: 12 can be substituted with alanine (A). In a particular aspect the variant IgM constant region is a variant human IgM constant region comprising an R344A mutation, presented herein as SEQ ID NO: 31. SEQ ID NO: 31 is presented below with the R344A mutation in bold underline:

```
SEQ ID NO: 31
GSASAPTLFPLVSCENSPSDTSSVAVGCLAQDFLPDSITFS

WKYKNNSDISSTRGFPSVLRGGKYAATSQVLLPSKDVM

QGTDEHVVCKVQHPNGNKEKNVPLPVIAELPPKVSVFV

PPRDGFFGNPRKSKLICQATGFSPRQIQVSWLREGKQVG

SGVTTDQVQAEAKESGPTTYKVTSTLTIKESDWLSQSMF

TCRVDHRGLTFQQNASSMCVPDQDTAIRVFAIPPSFASIF

LTKSTKLTCLVTDLTTYDSVTISWTRQNGEAVKTHTNIS

ESHPNATFSAVGEASICEDDWNSGERFTCTVTHTDLPSP

LKQTISRPKGVALHRPDVYLLPPAREQLNLAESATITCLV

TGFSPADVFVQWMQRGQPLSPEKYVTSAPMPEPQAPGR

YFAHSILTVSEEEWNTGETYTCVVAHEALPNRVTERTV

DKSTGKPTLYNVSLVMSDTAGTCY
```

In certain aspects, a variant IgM constant region or multimerizing fragment thereof of an IgM antibody or IgM-like antibody as provided herein comprises an amino acid substitution at the amino acid position corresponding to amino acid E345 of the wild-type human IgM constant region (SEQ ID NO: 12), which in turn corresponds to amino acid E468 according to the Kabat numbering system. By "an amino acid corresponding to amino acid E345 of the wild-type human IgM constant region" is meant the amino acid in the sequence of the IgM constant region of any species which is homologous to E345 in the human IgM constant region. The position corresponding to E345 in SEQ ID NO: 12 is conserved in the IgM constant region amino acid sequences of some species, e.g., non-human primates and mouse. See FIG. 1. In certain aspects, E345 of SEQ ID NO: 12 can be substituted with any amino acid. In certain aspects, E345 of SEQ ID NO: 12 can be substituted with alanine (A). In a particular aspect the variant IgM constant region is a variant human IgM constant region comprising an E345A mutation, presented herein as SEQ ID NO: 32. SEQ ID NO: 32 is presented below with the E345A mutation in bold underline:

```
SEQ ID NO: 32
GSASAPTLFPLVSCENSPSDTSSVAVGCLAQDFLPDSITFS

WKYKNNSDISSTRGFPSVLRGGKYAATSQVLLPSKDVM

QGTDEHVVCKVQHPNGNKEKNVPLPVIAELPPKVSVFV

PPRDGFFGNPRKSKLICQATGFSPRQIQVSWLREGKQVG

SGVTTDQVQAEAKESGPTTYKVTSTLTIKESDWLSQSMF

TCRVDHRGLTFQQNASSMCVPDQDTAIRVFAIPPSFASIF

LTKSTKLTCLVTDLTTYDSVTISWTRQNGEAVKTHTNIS

ESHPNATFSAVGEASICEDDWNSGERFTCTVTHTDLPSP

LKQTISRPKGVALHRPDVYLLPPAREQLNLRASATITCL

VTGFSPADVFVQWMQRGQPLSPEKYVTSAPMPEPQAPG

RYFAHSILTVSEEEWNTGETYTCVVAHEALPNRVTERTV

DKSTGKPTLYNVSLVMSDTAGTCY
```

Variant Human IgM Constant Regions with Reduced CDC Activity

In certain aspects, a variant human IgM constant region, when expressed as part of an IgM antibody or IgM-like antibody as provided herein can additionally exhibit reduced complement-dependent cytotoxicity (CDC) activity to cells in the presence of complement, relative to a reference IgM antibody or IgM-like antibody with a corresponding reference human IgM constant region identical, except for the mutations conferring reduced CDC activity. These CDC mutations can be combined with any of the mutations conferring increased serum half-life as provided herein. By "corresponding reference human IgM constant region" is meant a human IgM constant region or portion thereof, e.g., a Cµ3 domain, that is identical to the variant IgM constant region except for the modification or modifications in the constant region affecting CDC activity. In certain aspects, the variant human IgM constant region includes one or more amino acid substitutions, e.g., in the Cµ3 domain, relative to a wild-type human IgM constant region as described, e.g., in PCT Application No. PCT/US2018/026474, which is incorporated herein by reference in its entirety. Assays for measuring CDC are well known to those of ordinary skill in the art, and exemplary assays are described e.g., in PCT Application No. PCT/US2018/026474.

In certain aspects, a variant human IgM constant region conferring reduced CDC activity includes an amino acid substitution corresponding to the wild-type human IgM constant region at position P311 of SEQ ID NO: 12. In other aspects the variant IgM constant region as provided herein contains an amino acid substitution corresponding to the wild-type human IgM constant region at position P313 of SEQ ID NO: 12. In other aspects the variant IgM constant region as provided herein contains a combination of substitutions corresponding to the wild-type human IgM constant region at positions P311 of SEQ ID NO: 12 and P313 of SEQ ID NO: 12. The variant IgM constant region at amino acid position P311 of SEQ ID NO: 12 can be substituted, e.g., with alanine (P311A), serine (P311S), or glycine (P311G). The variant IgM constant region at amino acid position P313 of SEQ ID NO: 12 can be substituted, e.g., with alanine (P313A), serine (P313S), or glycine (P313G). The variant IgM constant region at amino acid positions P311 and P313 of SEQ ID NO: 12 can be substituted with alanine (P311A) and serine (P313S), respectively (SEQ ID NO: 15) or any combination of alanine, serine, and/or glycine. SEQ ID NO: 15 is presented below with the P311A and P313 S mutations in bold underline:

```
SEQ ID NO: 15
GSASAPTLFPLVSCENSPSDTSSVAVGCLAQDFLPDSITFS

WKYKNNSDISSTRGFPSVLRGGKYAATSQVLLPSKDVM

QGTDEHVVCKVQHPNGNKEKNVPLPVIAELPPKVSVFV

PPRDGFFGNPRKSKLICQATGFSPRQIQVSWLREGKQVG

SGVTTDQVQAEAKESGPTTYKVTSTLTIKESDWLSQSMF

TCRVDHRGLTFQQNASSMCVPDQDTAIRVFAIPPSFASIF

LTKSTKLTCLVTDLTTYDSVTISWTRQNGEAVKTHTNIS

ESHPNATFSAVGEASICEDDWNSGERFTCTVTHTDLASS

LKQTISRPKGVALHRPDVYLLPPAREQLNLRESATITCLV

TGFSPADVFVQWMQRGQPLSPEKYVTSAPMPEPQAPGR

YFAHSILTVSEEEWNTGETYTCVVAHEALPNRVTERTV

DKSTGKPTLYNVSLVMSDTAGTCY
```

In one aspect, an IgM antibody or IgM-like antibody as provided herein that includes a variant human IgM constant region that comprises amino acid substitutions at P311 and/or P313, e.g., P311A, P311S, P311G, P313A, P313S, and/or P313G or any combination thereof, has a maximum CDC achieved in a dose-response assay decreased by at least 10%, 20%, 30%, 40%, 50%, 60%, 70%, 80% or 90% relative to a binding molecule that includes a corresponding wild-type IgM constant region.

Polynucleotides, Vectors, and Host Cells

The disclosure further provides a polynucleotide, e.g., an isolated, recombinant, and/or non-naturally-occurring polynucleotide, comprising a nucleic acid sequence that encodes a polypeptide subunit of IgM or IgM-like antibody as provided herein. By "polypeptide subunit" is meant a portion of a binding molecule, binding unit, IgM antibody, IgM-like antibody, or antigen-binding domain that can be independently translated. Examples include, without limitation, an antibody variable domain, e.g., a VH or a VL, a J chain, a secretory component, a single chain Fv, an antibody heavy chain, an antibody light chain, an antibody heavy chain constant region, an antibody light chain constant region, and/or any fragment, variant, or derivative thereof.

In certain aspects, the polypeptide subunit can comprise an IgM heavy chain constant region or IgM-like heavy chain constant region or multimerizing fragment thereof, which can be fused to an antigen-binding domain or a subunit thereof, e.g., to the VH portion of an antigen-binding domain, all as provided herein. In certain aspects the polynucleotide can encode a polypeptide subunit comprising a human IgM heavy chain constant region, a human IgM-like heavy chain constant region or multimerizing fragment thereof, e.g., SEQ ID NO: 12 SEQ ID NO: 13, SEQ ID NO: 14, SEQ ID NO: 15, SEQ ID NO: 31, SEQ ID NO: 32, or SEQ ID NO: 34, any of which can be fused to an antigen-binding domain or subunit thereof, e.g., the C-terminal end of a VH.

In certain aspects, the polypeptide subunit can comprise an antibody VL portion of an antigen-binding domain as described elsewhere herein. In certain aspects the polypeptide subunit can comprise an antibody light chain constant region, e.g., a human antibody light chain constant region, or fragment thereof, which can be fused to the C-terminal end of a VL.

In certain aspects the polypeptide subunit can comprise a J-chain, a modified J-chain, or any functional fragment or variant thereof, as provided herein. In certain aspects the polypeptide subunit can comprise a human J-chain or functional fragment or variant thereof, including modified J-chains. In certain aspects the J-chain can comprise the amino acid sequence SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, SEQ ID NO: 23, or SEQ ID NO: 24.

In certain aspects a polynucleotide as provided herein, e.g., an expression vector such as a plasmid, can include a nucleic acid sequence encoding one polypeptide subunit, e.g., an IgM heavy chain or IgM-like heavy chain, a light chain, or a J-chain, or can include two or more nucleic acid sequences encoding two or more or all three polypeptide subunits of an IgM antibody or IgM-like antibody as provided herein. Alternatively, the nucleic acid sequences encoding the three polypeptide subunits can be on separate polynucleotides, e.g., separate expression vectors. The disclosure provides such single or multiple expression vectors. The disclosure also provides one or more host cells encoding the provided polynucleotide(s) or expression vector(s).

Thus, to form the antigen-binding domains, the nucleic acid sequences encoding the variable regions of antibodies can be inserted into expression vector templates for IgM or IgM-like structures, in particular those encoding variant IgM heavy chain constant regions as provided herein such as SEQ ID NO: 13, SEQ ID NO: 14, SEQ ID NO: 31, SEQ ID NO: 32, or SEQ ID NO: 34, and can be further combined a polynucleotide encoding a J-chain or functional fragment or variant thereof as provided herein, e.g., encoding SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, SEQ ID NO: 23, or SEQ ID NO: 24, more specifically encoding a variant J-chain comprising the amino acid sequence SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, SEQ ID NO: 23, or SEQ ID NO: 24, thereby creating IgM antibodies or IgM-like antibodies having five or six binding units, and possessing an increased serum half-life relative to an IgM or IgM-like antibody of identical structure except for the one or more single amino acid substitutions, insertions, or deletions in the IgM heavy chain constant region and/or in the J-chain as described elsewhere herein. In brief, nucleic acid sequences encoding the heavy and light chain variable domain sequences can be synthesized or amplified from existing molecules and inserted into one or more vectors in the proper orientation and in frame such that upon expression, the vector will yield the desired full length heavy or light chain. Vectors useful for these purposes are known in the art. Such vectors can also comprise enhancer and other sequences needed to achieve expression of the desired chains. Multiple vectors or single vectors can be used and can further encode the variant J-chain or functional fragment thereof. This vector or these vectors can be transfected into host cells and then the heavy and/or light chains and the variant J-chain or functional fragment thereof are expressed, the IgM or IgM-like antibodies are assembled, and purified. Upon expression the chains form fully functional multimeric IgM or IgM-like antibodies possessing enhanced serum half-life. The fully assembled multimeric IgM or IgM-like antibodies can then be purified by standard methods. The expression and purification processes can be performed at commercial scale, if needed.

The disclosure further provides a composition comprising two or more polynucleotides, where the two or more polynucleotides collectively can encode an IgM or IgM-like antibody with enhanced serum half-life as described above. In certain aspects the composition can include a polynucleotide encoding a wild-type or variant IgM or IgM-like heavy chain or multimerizing fragment thereof, e.g., a wild-type or variant human IgM heavy chain comprising a constant region amino acid sequence of SEQ ID NO: 12, SEQ ID NO: 13, SEQ ID NO: 14, SEQ ID NO: 15, SEQ ID NO: 31, SEQ ID NO: 32, or SEQ ID NO: 34 as described above where the IgM or IgM-like heavy chain further comprises an antigen-binding domain or a subunit thereof, e.g., a VH domain. The composition can further include a polynucleotide encoding a light chain or fragment thereof, e.g., a human kappa or lambda light chain that comprises at least a VL of an antigen-binding domain. A polynucleotide composition as provided can further include a polynucleotide encoding a J-chain, e.g., a variant J-chain or functional fragment thereof with at least one single amino acid substitution, insertion or deletion that can enhance serum half-life of the IgM or IgM-like antibody, e.g., a variant and/or modified J-chain comprising the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 10, SEQ ID NO: 23, or SEQ ID NO: 24. In certain aspects the polynucleotides making up a composition as provided herein can be situated on two, three, or more separate vectors, e.g., expression vectors. Such vectors are provided by the disclosure. In certain aspects two or more of the polynucleotides making up a composition as provided herein can be situated on a single vector, e.g., an expression vector. Such a vector is provided by the disclosure.

The disclosure further provides a host cell, e.g., a prokaryotic or eukaryotic host cell, comprising a polynucleotide or two or more polynucleotides encoding an IgM or IgM-like antibody as provided herein, or any subunit thereof, a polynucleotide composition as provided herein, or a vector or two, three, or more vectors that collectively encode the IgM or IgM-like antibody as provided herein, or any subunit thereof.

In a related aspect, the disclosure provides a method of producing an IgM or IgM-like antibody with increased serum half-life as provided by this disclosure, where the method comprises culturing a host cell as provided herein and recovering the IgM or IgM-like antibody.

Methods of Identifying Variant J-Chains and/or Variant IgM Heavy Chain Constant Regions that can Confer Increased Serum Half-Life This disclosure further provides various methods for identifying variant antibody subunits that can increase the serum half-life of an antibody, e.g., an IgM antibody or IgM-like antibody, comprising the subunit. These methods utilize standard methods of molecular biology and site-directed mutagenesis that will be familiar to the person of ordinary skill in the art. Exemplary methodology is provided in the Examples section.

In certain aspects, this disclosure provides a method of identifying variant J-chains that can increase the serum half-life of pentameric IgM antibodies, pentameric IgM-like antibodies, dimeric IgA antibodies, and/or dimeric IgA-like antibodies comprising the variant J-chains. The method includes testing pentameric IgM antibodies or pentameric IgM-like antibodies, or alternatively dimeric IgA antibodies or dimeric IgA-like antibodies, assembled to include variant J-chains or fragments thereof for increased serum half-life in a subject animal relative to a reference antibody, where the reference antibody is identical to the test antibodies except for the variant J-chains. According to these aspects, a series of variant J-chains or fragments thereof comprising defined amino acid insertions, deletions, or substitutions are constructed and tested relative to a reference J-chain, e.g., a J-chain, a modified J-chain, and/or a functional fragment thereof identical to the variant J-chains except for the defined amino acid insertions, deletions, or substitutions. In certain aspects, the variant J-chains can include one, two, three, four, or more defined single amino acid substitutions, insertions, or deletions as described elsewhere herein. In certain aspects, limited regions of the J-chain are targeted for mutagenesis, e.g., those regions necessary or contributory for binding to certain immunoglobulin receptors, e.g., the Fc alpha-mu receptor (FcαμR), the polymeric Ig receptor (pIgR), the Fc-mu receptor (FcμR), two or more of the receptors, or all three of the receptors as described in more detail in Examples 1 and 2. In certain aspects the entire length of the J-chain can be subjected to mutagenesis, e.g., by individually substituting the amino acid at each position of a J-chain, e.g., SEQ ID NO: 2 with another amino acid, e.g., alanine, serine, or threonine. The mutated J-chains can then be co-expressed, e.g., with a reference IgM heavy chain and an antibody light chain, and the resulting pentameric IgM antibodies analyzed for proper assembly, antigen-binding, and any other desired functions. The resulting IgM antibodies or IgM-like antibodies can then be assessed for increased serum half-life in a subject animal, e.g., in a mouse model as described in the Examples. Those J-chains that confer increased serum half-life upon the respective IgM antibodies or IgM-like antibodies are then recovered and further characterized as necessary. This method can also be applied to identify variant J-chains that can confer increased serum half-life upon a dimeric IgA antibody or IgA-like antibody comprising the variant J-chains, using similar methods.

In certain aspects, this disclosure provides a method of identifying variant J-chains that can increase the serum half-life of pentameric IgM antibodies, pentameric IgM-like antibodies, dimeric IgA antibodies, and/or dimeric IgA-like antibodies comprising the variant J-chains. The method includes testing pentameric IgM antibodies or pentameric IgM-like antibodies, or alternatively dimeric IgA antibodies or dimeric IgA-like antibodies, assembled to include variant J-chains or fragments thereof for reduced binding to certain immunoglobulin receptors, e.g., the Fc alpha-mu receptor (FcαμR), the polymeric Ig receptor (pIgR), the Fc-mu receptor (FcμR), two or more of the receptors, or all three of the receptors. Regions of the J-chain to be subjected to mutagenesis can be targeted by determining those regions necessary or contributory to receptor binding, e.g., as described in Example 1. Alternatively, amino acids along the entire length of the J-chain can be subjected to mutagenesis and the resulting antibodies comprising the variant J-chains tested for receptor binding. Reduced receptor binding can be measured by any suitable assay, e.g., via the ELISA assays described in Example 2. The variant J-chains or fragments thereof are constructed to include defined amino acid insertions, deletions, or substitutions as described above and elsewhere herein. Those variant J-chains conferring reduced antibody binding to one or more of the receptors can then be recovered and further characterized as necessary. The method can further include testing pentameric IgM antibodies or pentameric IgM-like antibodies, or dimeric IgA antibodies or dimeric IgA-like antibodies comprising the recovered variant J-chains or fragments thereof for increased serum half-life in a subject animal, e.g., in a mouse model as described in the Examples, relative to reference antibodies identical except for the defined amino acid substitutions, deletions, or insertions in the variant J-chains or fragments thereof. This method can also be applied to identify variant J-chains that can confer increased serum half-life upon a dimeric IgA antibody or IgA-like antibody comprising the variant J-chains, using similar methods.

The disclosure further provides a method of identifying variant IgM heavy chain constant regions (or variant IgA heavy chain constant regions) that can increase the serum half-life of an IgM antibody or IgM-like antibody (or IgA antibody or IgA-like antibody) comprising the variant IgM (or IgA) heavy chain constant regions. The method for IgM includes testing IgM antibodies or IgM-like antibodies comprising variant IgM heavy chain constant regions for increased serum half-life in a subject animal relative to a reference IgM antibody or IgM-like antibody, wherein the variant IgM heavy chain constant regions comprise defined amino acid insertions, deletions, or substitutions, and wherein the reference IgM antibody or IgM-like antibody comprises IgM heavy chain constant regions identical to the variant IgM heavy chain constant regions except for the defined amino acid insertions, deletions or substitutions. The method further includes recovering those IgM antibodies or IgM-like antibodies comprising variant IgM heavy chain constant regions that confer increased serum half-life upon the IgM antibodies or IgM-like antibodies comprising the variant IgM heavy chain constant regions relative to reference IgM antibodies or IgM-like antibodies. Any number of variant IgM or IgM-like heavy chain constant regions comprising, e.g., one, two, three, four, or more defined single amino acid substitutions, insertions, or deletions can be tested. Regions of the IgM or IgM-like heavy chain constant regions to be subjected to mutagenesis can be determined empirically, e.g., by identifying those regions, e.g., in the Cμ4 domain, that are either required for or contribute to binding to various immunoglobulin receptors such as the Fc alpha-mu receptor (FcαμR), Fc mu receptor (FcμR), the polymeric Ig receptor (pIgR), any combination of two of the receptors, or all three of the receptors, as described in the Examples. Alternatively, the entire length of selected Cμ domains or the entire IgM heavy chain constant region, can be subjected to mutagenesis, e.g., via substituting amino acids at each position with a different amino acid, e.g., alanine, serine, or threonine. The variant IgM heavy chain constant regions are then assembled with other antibody subunits, e.g., an antibody light chain and optionally a J-chain, and proper assembly and antigen-binding are tested. The test antibodies can then be evaluated for increased serum half-life in a subject animal, e.g., a mouse model as described in the Examples. This method can also be applied to identify variant IgA or IgA-like heavy chain constant regions that can confer increased serum half-life upon a dimeric IgA antibody or IgA-like antibody comprising the variant constant regions, using similar methods.

The disclosure further provides a method of identifying variant IgM heavy chain constant regions (or alternatively variant IgA heavy chain constant regions) that can increase the serum half-life of an IgM antibody or IgM-like antibody (or an IgA antibody or IgA-like antibody) comprising the variant heavy chain constant regions. The method for IgM includes testing IgM antibodies or IgM-like antibodies comprising variant IgM heavy chain constant regions for reduced binding to the Fc alpha-mu receptor (FcαμR), Fc mu receptor (FcμR), the polymeric Ig receptor (pIgR), any combination of two of the receptors, or all three of the receptors relative to a reference IgM antibody or IgM-like antibody, wherein the variant IgM heavy chain constant regions comprise defined amino acid insertions, deletions, or substitutions, and wherein the reference IgM antibody or IgM-like antibody comprises IgM heavy chain constant regions identical to the variant IgM heavy chain constant regions except for the defined amino acid insertions, deletions or substitutions. The method further includes recovering those IgM antibodies or IgM-like antibodies comprising variant IgM heavy chain constant regions that confer reduced FcαμR binding ability, reduced FcμR binding ability, reduced pIgR binding ability, reduced ability to bind to any two of the receptors, or reduced ability to bind to all three of the receptors, upon the IgM antibodies or IgM-like antibodies comprising the variant IgM heavy chain constant regions relative to reference IgM antibody or IgM-like antibody. Any number of variant IgM or IgM-like heavy chain constant regions comprising, e.g., one, two, three, four, or more defined single amino acid substitutions, insertions, or deletions can be tested. Regions of the IgM or IgM-like heavy chain constant regions to be subjected to mutagenesis can be determined empirically, e.g., by identifying those regions, e.g., in the Cμ4 domain, that are either required for or contribute to binding to various immunoglobulin receptors such as the Fc alpha-mu receptor (FcαμR), Fc mu receptor (FcμR), the polymeric Ig receptor (pIgR), any combination of two of the receptors, or all three of the receptors, as described in the Examples. Alternatively, the entire length of selected Cμ domains or the entire IgM heavy chain constant region, can be subjected to mutagenesis, e.g., via substituting amino acids at each position with a different amino acid, e.g., alanine, serine, or threonine. The variant IgM heavy chain constant regions are then assembled with other antibody subunits, e.g., an antibody light chain and optionally a J-chain, and proper assembly and antigen-binding are tested. The variant IgM heavy chain constant regions are then assembled with other antibody subunits, e.g., an antibody light chain and optionally a J-chain, and proper assembly and antigen-binding are tested. Reduced receptor binding can be measured by any suitable assay, e.g., via the ELISA assays described in Example 2. Test antibodies comprising the recovered variant IgM or IgM-like heavy chain constant regions can then be evaluated for increased serum half-life in a subject animal, e.g., a mouse model as described in the Examples. This method can also be applied to identify variant IgA or IgA-like heavy chain constant regions that can confer increased serum half-life upon a dimeric IgA antibody or IgA-like antibody comprising the variant constant regions, using similar methods.

Methods of Use

The disclosure further provides a method of treating a disease or disorder in a subject in need of treatment, comprising administering to the subject a therapeutically effective amount of an IgM or IgM-like antibody as provided herein. By "therapeutically effective dose or amount" or "effective amount" is intended an amount of an IgM or IgM-like antibody, that when administered brings about a positive immunotherapeutic response with respect to treatment of subject.

Effective doses of compositions for treatment of cancer vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated. Treatment dosages can be titrated using routine methods known to those of skill in the art to optimize safety and efficacy.

The subject to be treated can be any animal, e.g., mammal, in need of treatment, in certain aspects, the subject is a human subject.

In its simplest form, a preparation to be administered to a subject is an IgM or IgM-like antibody as provided herein, or a multimeric antigen-binding fragment thereof, administered in conventional dosage form, which can be combined with a pharmaceutical excipient, carrier or diluent as described elsewhere herein.

The compositions of the disclosure can be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Pharmaceutical Compositions and Administration Methods

Methods of preparing and administering an IgM or IgM-like antibody as provided herein to a subject in need thereof are well known to or are readily determined by those skilled in the art in view of this disclosure. The route of administration of can be, for example, intratumoral, oral, parenteral, by inhalation or topical. The term parenteral as used herein includes, e.g., intravenous, intraarterial, intraperitoneal, intramuscular, subcutaneous, rectal, or vaginal administration. While these forms of administration are contemplated as suitable forms, another example of a form for administration would be a solution for injection, in particular for intratumoral, intravenous, or intraarterial injection or drip. A suitable pharmaceutical composition can comprise a buffer (e.g. acetate, phosphate or citrate buffer), a surfactant (e.g. polysorbate), optionally a stabilizer agent (e.g. human albumin), etc.

As discussed herein, an IgM or IgM-like antibody as provided herein can be administered in a pharmaceutically effective amount for the treatment of a subject in need thereof. In this regard, it will be appreciated that the disclosed IgM or IgM-like antibody can be formulated so as to facilitate administration and promote stability of the active agent. Pharmaceutical compositions accordingly can comprise a pharmaceutically acceptable, non-toxic, sterile carrier such as physiological saline, non-toxic buffers, preservatives and the like. A pharmaceutically effective amount of an IgM or IgM-like antibody as provided herein means an amount sufficient to achieve effective binding to a target and to achieve a therapeutic benefit. Suitable formulations are described in Remington's Pharmaceutical Sciences, e.g., 21$^{st}$ Edition (Lippincott Williams & Wilkins) (2005).

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an IgM or IgM-like antibody that can be combined with carrier materials to produce a single dosage form will vary depending, e.g., upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, an IgM or IgM-like antibody as provided herein can be administered to a subject in need of therapy in an amount sufficient to produce a therapeutic effect. An IgM or IgM-like antibody as provided herein can be administered to the subject in a conventional dosage form prepared by combining the antibody or multimeric antigen-binding fragment, variant, or derivative thereof of the disclosure with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables.

This disclosure also provides for the use of an IgM or IgM-like antibody as provided herein in the manufacture of a medicament for treating, preventing, or managing cancer.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Green and Sambrook, ed. (2012) Molecular Cloning A Laboratory Manual (4th ed.; Cold Spring Harbor Laboratory Press); Sambrook et al., ed. (1992) Molecular Cloning: A Laboratory Manual, (Cold Springs Harbor Laboratory, NY); D. N. Glover and B. D. Hames, eds., (1995) DNA Cloning 2d Edition (IRL Press), Volumes 1-4; Gait, ed. (1990) Oligonucleotide Synthesis (IRL Press); Mullis et al. U.S. Pat. No. 4,683,195; Hames and Higgins, eds. (1985) Nucleic Acid Hybridization (IRL Press); Hames and Higgins, eds. (1984) Transcription And Translation (IRL Press); Freshney (2016) Culture Of Animal Cells, 7th Edition (Wiley-Blackwell); Woodward, J., Immobilized Cells And Enzymes (IRL Press) (1985); Perbal (1988) A Practical Guide To Molecular Cloning; 2d Edition (Wiley-Interscience); Miller and Calos eds. (1987) Gene Transfer Vectors For Mammalian Cells, (Cold Spring Harbor Laboratory); S. C. Makrides (2003) Gene Transfer and Expression in Mammalian Cells (Elsevier Science); Methods in Enzymology, Vols. 151-155 (Academic Press, Inc., N.Y.); Mayer and Walker, eds. (1987) Immunochemical Methods in Cell and Molecular Biology (Academic Press, London); Weir and Blackwell, eds.; and in Ausubel et al. (1995) Current Protocols in Molecular Biology (John Wiley and Sons).

General principles of antibody engineering are set forth, e.g., in Strohl, W. R., and L. M. Strohl (2012), Therapeutic Antibody Engineering (Woodhead Publishing). General principles of protein engineering are set forth, e.g., in Park and Cochran, eds. (2009), Protein Engineering and Design (CDC Press). General principles of immunology are set forth, e.g., in: Abbas and Lichtman (2017) Cellular and Molecular Immunology 9th Edition (Elsevier). Additionally, standard methods in immunology known in the art can be followed, e.g., in Current Protocols in Immunology (Wiley Online Library); Wild, D. (2013), The Immunoassay Handbook 4th Edition (Elsevier Science); Greenfield, ed. (2013), Antibodies, a Laboratory Manual, 2d Edition (Cold Spring Harbor Press); and Ossipow and Fischer, eds., (2014), Monoclonal Antibodies: Methods and Protocols (Humana Press).

All of the references cited above, as well as all references cited herein, are incorporated herein by reference in their entireties.

The following examples are offered by way of illustration and not by way of limitation.

EXAMPLES

We hypothesized that the interaction between IgM and one or more of its Ig receptors, the Fc μ receptor (FcμR), the Fc α/μ receptor (FcαμR), and/or the polymeric Ig receptor (pIgR), contributed to the particular pharmacokinetics and pharmacodynamics observed for IgM antibodies in vivo. Accordingly, we set out to identify specific regions of IgM involved in binding to these receptors, and asked whether alterations to these regions, e.g., amino acid substitutions, could modulate, e.g., inhibit receptor binding to an IgM antibody comprising the alterations. We then tested whether certain of these alterations affected the in vivo plasma availability of the IgM antibodies comprising the alterations.

Example 1: Screening J-Chain and Fcµ Peptide Arrays for Receptor Binding

In order to identify the regions on IgM constant regions and J-chain where FcµR, FcαµR, and/or pIgR bind, we used a peptide array-based technology (PEPperPRINT; WWW_dot_pepperprint_dot_com). A complete set of peptides based on the amino acid sequence of human J chain (SEQ ID NO: 2) and the CO and CO domains of human IgM (about amino acid 224 to about amino acid 430 of SEQ ID NO: 12) were synthesized and immobilized on solid supports, as follows. The sequences of IgM µ3, µ4 and J-chain were elongated with neutral GSGSGSG linkers (SEQ ID NO: 33) at the N- and the C-terminus to avoid truncated peptides. The elongated protein sequences were translated into 9 and 13 amino acid peptides with peptide-peptide overlaps of 8 and 12 amino acids, respectively. After peptide synthesis, all peptides were cyclized via a thioether linkage between a C-terminal cysteine side chain thiol group and an appropriately modified N-terminus. The resulting IgM peptide microarrays contained 844 different peptides printed in duplicate (1,688 peptide spots), along with control peptides. The constrained peptides with one residue increments were probed with 1, 10, or 100 µg/mL of recombinant human pIgR (amino acids 19-638 of SEQ ID NO: 20, available from R&D Systems), human FcαµR (amino acids 18-251 of SEQ ID NO: 21, available from R&D Systems), and human FcapR (amino acids 17 to 450 of SEQ ID NO: 22, available from R&D Systems), each with a 6X HIS tag in incubation buffer (PBS, pH 7.4 with 0.005% Tween 20 and 10% Rockland blocking buffer (MB-070)) was followed by staining with secondary antibody mouse anti-6x-His Epitope Tag DyLight680 and with the control antibodies as well as read-out at scanning intensities of 7/7 (red/green).

Quantification of spot intensities and peptide annotation were based on the 16-bit gray scale tiff files at scanning intensities of 7/7 that exhibit a higher dynamic range than the 24-bit colorized tiff files; microarray image analysis was done with PEPSLIDE® Analyzer. A software algorithm breaks down fluorescence intensities of each spot into raw, foreground and background signal (see "Raw Data" tabs) and calculates averaged median foreground intensities and spot-to-spot deviations of spot duplicates. Based on averaged median foreground intensities, an intensity map was generated.

Averaged spot intensities of the assays were plotted with the target proteins against the protein sequence from the N-terminus of IgM µ3-chain to the C-terminus of IgM J-chain to visualize overall spot intensities and signal-to-noise ratios. The intensity plots were correlated with peptide and intensity maps as well as with visual inspection of the microarray scans to identify the main interactions of the target proteins.

Utilizing the raw data, key regions of the J-chain as well as IgM HC constant regions that bound to the receptors in the PEPperPRINT platform were identified.

Human FcαµR bound to the following underlined regions of the mature J-chain, SEQ ID NO: 2:

```
  1 QEDERIVLVD NKCKCARITS RIIRSSEDPN EDIVERNIRI IVPLNNRENI

51 SDPTSPLRTR FVYHLSDLCK KCDPTEVELD NQIVTATQSN ICDEDSATET

101 CYTYDRNKCY TAVVPLVYGG ETKMVETALT PDACYPD
```

Accordingly, regions of the mature human J-chain that contribute to binding of human FcαµR can include, e.g., amino acids within and/or amino acids overlapping with and/or amino acids comprising, consisting of, or consisting essentially of amino acids 1 to 10 of SEQ ID NO: 2, amino acids within and/or amino acids overlapping with and/or amino acids comprising, consisting of, or consisting essentially of amino acids 87 to 105 of SEQ ID NO: 2, and/or amino acids within and/or amino acids overlapping with and/or amino acids comprising, consisting of, or consisting essentially of amino acids 125 to 137 of SEQ ID NO: 2. As those of ordinary skill in the art will appreciate, pentameric IgM antibodies or IgM-like antibodies comprising variant J-chains with mutations, e.g., amino acid insertions, deletions, and/or substitutions, within these regions, overlapping with these regions, and/or corresponding to these regions (e.g., in a J-chain amino acid sequence from another species) can be tested for inhibition of FcαµR binding, e.g., as described in Example 2, and/or for enhancement of serum half-life, e.g., as described in Example 3.

Human pIgR bound to the following double underlined regions of the mature J-chain, SEQ ID NO: 2:

```
  1 QEDERIVLVD NKCKCARITS RIIRSSEDPN EDIVERNIRI IVPLNNRENI

51 SDPTSPLRTR FVYHLSDLCK KCDPTEVELD NQIVTATQSN ICDEDSATET

101 CYTYDRNKCY TAVVPLVYGG ETKMVETALT PDACYPD
```

Accordingly, regions of the mature human J-chain that contribute to binding of human pIgR can include, e.g., amino acids within and/or amino acids overlapping with and/or amino acids comprising, consisting of, or consisting essentially of amino acids 12 to 24 of SEQ ID NO: 2, and/or amino acids within and/or amino acids overlapping with and/or amino acids comprising, consisting of, or consisting essentially of amino acids 93 to 105 of SEQ ID NO: 2. As those of ordinary skill in the art will appreciate, pentameric IgM antibodies or IgM-like antibodies comprising variant J-chains with mutations, e.g., amino acid insertions, deletions, and/or substitutions, within these regions, overlapping with these regions, and/or corresponding to these regions (e.g., in a J-chain amino acid sequence from another species) can be tested for inhibition of pIgR binding, e.g., as described in Example 2, and/or for enhancement of serum half-life, e.g., as described in Example 3.

Human FcµR bound to the following squiggly underlined regions of the mature J-chain, SEQ ID NO: 2:

```
  1 QEDERIVLVD NKCKCARITS RIIRSSEDPN EDIVERNIRI IVPLNNRENI
    ~~~~~

51 SDPTSPLRTR FVYHLSDLCK KCDPTEVELD NQIVTATQSN ICDEDSATET
                                      ~~~~~~~~~~~~~~~~~

101 CYTYDRNKCY TAVVPLVYGG ETKMVETALT PDACYPD
    ~~~~~                 ~~~~~~~~~~~~~~~
```

Accordingly, regions of the mature human J-chain that contribute to binding of human FcµR can include, e.g., amino acids within and/or amino acids overlapping with and/or amino acids comprising, consisting of, or consisting essentially of amino acids 1 to 4 of SEQ ID NO: 2, amino acids within and/or amino acids overlapping with and/or amino acids comprising, consisting of, or consisting essentially of amino acids 87 to 105 of SEQ ID NO: 2, and/or amino acids within and/or amino acids overlapping with and/or amino acids comprising, consisting of, or consisting essentially of amino acids 125 to 137 of SEQ ID NO: 2. As those of ordinary skill in the art will appreciate, pentameric IgM antibodies or IgM-like antibodies comprising variant J-chains with mutations, e.g., amino acid insertions, dele-tions, and/or substitutions, within these regions, overlapping with these regions, and/or corresponding to these regions (e.g., in a J-chain amino acid sequence from another species) can be tested for inhibition of FcµR binding, e.g., as described in Example 2, and/or for enhancement of serum half-life, e.g., as described in Example 3.

Human FcαµR bound to the following underlined regions of Cµ3 and CO of the human IgM constant region, SEQ ID NO: 12 (numbering for SEQ ID NO: 12/KABAT provided):

Sequential (SEQ ID NO: 12)/KABAT Numbering
Key for IgM Heavy Chain

```
  1/127 GSASAPTLFP LVSCENSPSD TSSVAVGCLA QDFLPDSITF SWKYKNNSDI

51/176 SSTRGFPSVL RGGKYAATSQ VLLPSKDVMQ GTDEHVVCKV QHPNGNKEKN

101/226 VPLPVIAELP PKVSVFVPPR DGFFGNPRKS KLICQATGFS PRQIQVSWLR

151/274 EGKQVGSGVT TDQVQAEAKE SGPTTYKVTS TLTIKESDWL SQSMFTCRVD

201/324 HRGLTFQQNA SSMCVPDQDT AIRVFAIPPS FASIFLTKST KLTCLVTDLT

251/374 TYDSVTISWT RQNGEAVKTH TNISESHPNA TFSAVGEASI CEDDWNSGER

301/424 FTCTVTHTDL PSPLKQTISR PKGVALHRPD VYLLPPAREQ LNLRESATIT

351/474 CLVTGFSPAD VFVQWMQRGQ PLSPEKYVTS APMPEPQAPG RYFAHSILTV

401/524 SEEEWNTGET YTCVVAHEAL PNRVTERTVD KSTGKPTLYN VSLVMSDTAG

451/574 TCY
```

Accordingly, regions of the human IgM constant region that contribute to binding of human FcapR can include, e.g., amino acids within and/or amino acids overlapping with and/or amino acids comprising, consisting of, or consisting essentially of amino acids 241 to 253 of SEQ ID NO: 12, amino acids within and/or amino acids overlapping with and/or amino acids comprising, consisting of, or consisting essentially of amino acids 282 to 294 of SEQ ID NO: 12, amino acids within and/or amino acids overlapping with and/or amino acids comprising, consisting of, or consisting essentially of amino acids 342 to 354 of SEQ ID NO: 12, and/or amino acids within and/or amino acids overlapping with and/or amino acids comprising, consisting of, or consisting essentially of amino acids 393 to 415 of SEQ ID NO: 12. As those of ordinary skill in the art will appreciate, IgM antibodies or IgM-like antibodies comprising IgM heavy chain constant regions with mutations, e.g., amino acid insertions, deletions, and/or substitutions, within these regions, overlapping with these regions, and/or corresponding to these regions (e.g., in an IgM heavy chain constant region amino acid sequence from another species such as those shown in FIG. 1) can be tested for inhibition of FcapR binding, e.g., as described in Example 2, and/or for enhancement of serum half-life, e.g., as described in Example 3.

Human pIgR bound to the following double underlined regions of Cμ3 and CO of the human IgM constant region, SEQ ID NO: 12 (numbering for SEQ ID NO: 12/KABAT provided):

```
  1/127  GSASAPTLFP  LVSCENSPSD  TSSVAVGCLA  QDFLPDSITF  SWKYKNNSDI

51/176  SSTRGFPSVL  RGGKYAATSQ  VLLPSKDVMQ  GTDEHVVCKV  QHPNGNKEKN

101/226  VPLPVIAELP  PKVSVFVPPR  DGFFGNPRKS  KLICQATGFS  PRQIQVSWLR

151/274  EGKQVGSGVT  TDQVQAEAKE  SGPTTYKVTS  TLTIKESDWL  SQSMFTCRVD

201/324  HRGLTFQQNA  SSMCVPDQDT  AIRVFAIPPS  FASIFLTKST  KLTCLVTDLT

251/374  TYDSVTISWT  RQNGEAVKTH  TNISESHPNA  TFSAVGEASI  CEDDWNSGER

301/424  FTCTVTHTDL  PSPLKQTISR  PKGVALHRPD  VYLLPPAREQ  LNLRESATIT

351/474  CLVTGFSPAD  VFVQWMQRGQ  PLSPEKYVTS  APMPEPQAPG  RYFAHSILTV

401/524  SEEEWNTGET  YTCVVAHEAL  PNRVTERTVD  KSTGKPTLYN  VSLVMSDTAG

451/574  TCY
```

Accordingly, regions of the human IgM constant region that contribute to binding of human pIgR can include, e.g., amino acids within and/or amino acids overlapping with and/or amino acids comprising, consisting of, or consisting essentially of amino 232 to 244 of SEQ ID NO: 12, amino acids within and/or amino acids overlapping with and/or amino acids comprising, consisting of, or consisting essentially of amino acids 287 to 304 of SEQ ID NO: 12, and/or amino acids within and/or amino acids overlapping with and/or amino acids comprising, consisting of, or consisting essentially of amino acids 397 to 413 of SEQ ID NO: 12. As those of ordinary skill in the art will appreciate, IgM antibodies or IgM-like antibodies comprising IgM heavy chain constant regions with mutations, e.g., amino acid insertions, deletions, and/or substitutions, within these regions, overlapping with these regions, and/or corresponding to these regions (e.g., in an IgM heavy chain constant region amino acid sequence from another species such as those shown in FIG. 1) can be tested for inhibition of pIgR binding, e.g., as described in Example 2, and/or for enhancement of serum half-life, e.g., as described in Example 3.

Human FcμR bound to the following squiggly underlined regions of Cμ3 and Cμ4 of the human IgM constant region, SEQ ID NO: 12 (numbering for SEQ ID NO: 12/KABAT provided):

```
  1/127  GSASAPTLFP  LVSCENSPSD  TSSVAVGCLA  QDFLPDSITF  SWKYKNNSDI

51/176  SSTRGFPSVL  RGGKYAATSQ  VLLPSKDVMQ  GTDEHVVCKV  QHPNGNKEKN

101/226  VPLPVIAELP  PKVSVFVPPR  DGFFGNPRKS  KLICQATGFS  PRQIQVSWLR

151/274  EGKQVGSGVT  TDQVQAEAKE  SGPTTYKVTS  TLTIKESDWL  SQSMFTCRVD

201/324  HRGLTFQQNA  SSMCVPDQDT  AIRVFAIPPS  FASIFLTKST  KLTCLVTDLT
```

-continued

```
251/374 TYDSVTISWT RQNGEAVKTH TNIISESHPNA TFSAVGEASI CEDDWNSGER

301/424 FTCTVTHTDL PSPLKQTISR PKGVALHRPD VYLLPPAREQ LNLRESATIT

351/474 CLVTGFSPAD VFVQWMQRGQ PLSPEKYVTS APMPEPQAPG RYFAHSILTV

401/524 SEEEWNTGET YTCVVAHEAL PNRVTERTVD KSTGKPTLYN VSLVMSDTAG

451/574 TCY
```

Accordingly, regions of the human IgM constant region that contribute to binding of human FcµR can include, e.g., amino acids within and/or amino acids overlapping with and/or amino acids comprising, consisting of, or consisting essentially of amino acids 282 to 305 of SEQ ID NO: 12, and/or amino acids within and/or amino acids overlapping with and/or amino acids comprising, consisting of, or consisting essentially of amino acids 393 to 417 of SEQ ID NO: 12. As those of ordinary skill in the art will appreciate, IgM antibodies or IgM-like antibodies comprising IgM heavy chain constant regions with mutations, e.g., amino acid insertions, deletions, and/or substitutions, within these regions, overlapping with these regions, and/or corresponding to these regions (e.g., in an IgM heavy chain constant region amino acid sequence from another species such as those shown in FIG. 1) can be tested for inhibition of FcµR binding, e.g., as described in Example 2, and/or for enhancement of serum half-life, e.g., as described in Example 3.

Example 2: Construction of Alanine Scanning IgM J-Chain and Fc Mutants, and Screening for Receptor Binding Inhibition by ELISA The J-chains and IgM constant regions of the monospecific anti-CD20 IgM antibody 1.5.3 as a monospecific pentamer (with the mature human J-chain of SEQ ID NO: 2), and the bispecific anti-CD20 IgM antibody 1.5.3 IgM as a bispecific pentamer (with the "V15J" J-chain, SEQ ID NO: 9), both as as described in PCT Publ. No. WO 2016/141303, were subjected to alanine-scanning mutagenesis to determine whether certain regions identified via the PEPper-PRINT analysis (Example 1) could be modified to reduce or inhibit binding of FcαµR, FcµR, and/or pIgR. Mutants tested included J-chain alanine substitutions at positions corresponding to positions Y102 and T103 of the human mature J-chain of SEQ ID NO: 2 (Y102A and T103A). The modified "V15J" J-chain comprising the Y102A mutation is presented as SEQ ID NO: 10, the modified "V15J" J-chain comprising the T103A mutation is presented as SEQ ID NO: 23. SEQ ID NO: 9, SEQ ID NO: 10, and SEQ ID NO: 23 are presented below.

```
SEQ ID NO: 9:
QVQLVQSGAEVKKPGASVKVSCKASGYTFISYTMHWV

RQAPGQGLEWMGYINPRSGYTHYNQKLKDKATLTADK

SASTAYMELSSLRSEDTAVYYCARSAYYDYDGFAYWG

QGTLVTVSSGGGGSGGGGSGGGGSDIQMTQSPSSLSASV

GDRVTITCSASSSVSYMNWYQQKPGKAPKRLIYDTSKL

ASGVPSRFSGSGSGTDFTLTISSLQPEDFATYYCQQWSSN
```

```
PPTFGGGTKLEIKGGGGSGGGGSGGGGSQEDERIVLVDN

KCKCARITSRIIRSSEDPNEDIVERNIRIIVPLNNRENISDPT

SPLRTRFVYHLSDLCKKCDPTEVELDNQIVTATQSNICD

EDSATETCYTYDRNKCYTAVVPLVYGGETKMVETALTP

DACYPD
```

```
SEQ ID NO: 10:
QVQLVQSGAEVKKPGASVKVSCKASGYTFISYTMHWV

RQAPGQGLEWMGYINPRSGYTHYNQKLKDKATLTADK

SASTAYMELSSLRSEDTAVYYCARSAYYDYDGFAYWG

QGTLVTVSSGGGGSGGGGSGGGGSDIQMTQSPSSLSASV

GDRVTITCSASSSVSYMNWYQQKPGKAPKRLIYDTSKL

ASGVPSRFSGSGSGTDFTLTISSLQPEDFATYYCQQWSSN

PPTFGGGTKLEIKGGGGSGGGGSGGGGSQEDERIVLVDN

KCKCARITSRIIRSSEDPNEDIVERNIRIIVPLNNRENISDPT

SPLRTRFVYHLSDLCKKCDPTEVELDNQIVTATQSNICD

EDSATETCATYDRNKCYTAVVPLVYGGETKMVETALTP

DACYPD
```

```
SEQ ID NO: 23:
QVQLVQSGAEVKKPGASVKVSCKASGYTFISYTMHWV

RQAPGQGLEWMGYINPRSGYTHYNQKLKDKATLTADK

SASTAYMELSSLRSEDTAVYYCARSAYYDYDGFAYWG

QGTLVTVSSGGGGSGGGGSGGGGSDIQMTQSPSSLSASV

GDRVTITCSASSSVSYMNWYQQKPGKAPKRLIYDTSKL

ASGVPSRFSGSGSGTDFTLTISSLQPEDFATYYCQQWSSN

PPTFGGGTKLEIKGGGGSGGGGSGGGGSQEDERIVLVDN

KCKCARITSRIIRSSEDPNEDIVERNIRIIVPLNNRENISDPT

SPLRTRFVYHLSDLCKKCDPTEVELDNQIVTATQSNICD

EDSATETCYAYDRNKCYTAVVPLVYGGETKMVETALT

PDACYPD
```

Mutants tested on the human IgM constant region included alanine mutations at positions corresponding to R344, E345, S401 and E402 of SEQ ID NO: 12 (R344A, SEQ ID NO: 31, E345A, SEQ ID NO: 32, S401A, SEQ ID NO: 13, E402A, SEQ ID NO: 14, and E403A, SEQ ID NO: 34). Two variant IgM constant region mutations, SEQ ID NO: 13 and SEQ ID NO: 14, were tested for their effect on in vivo half-life of IgMs comprising the mutations, with both the "wild-type" V15J J-chain (SEQ ID NO: 9), and with the V15J J-chain comprising the Y102A mutation (SEQ ID NO: 10), see Example 3).

DNA fragments encoding the heavy, light, and J-chains of the selected mutants were synthesized by a commercial vendor. The DNA constructs were transformed into competent bacteria and plated on LB plates with multiple selective antibiotics. Several bacterial colonies were picked, and DNA preparations were made by standard molecular biology techniques. The constructs encoding the heavy chain and light chains were verified by sequencing. The plasmid constructs encoding the heavy chains, light chains, and J-chain were cotransfected into HEK293/Expi293/CHO cells, and cells that expressed the CD20 IgM antibodies were selected, all according to standard methods. Antibodies present in the cell supernatants were recovered using Capture Select IgM (Catalog 2890.05, BAC, Thermo Fisher) according to the manufacturer's protocol. Antibodies were evaluated on SDS-polyacrylamide gel electrophoresis under non-reducing conditions to show assembly as previously described, e.g., in PCT Publication No. WO 2016/141303. Each of the mutants was verified for expression and assembly, and the bispecific constructs were verified to retain their ability to facilitate T-cell-mediated cytotoxicity.

Receptor binding to certain of the IgM mutants and corresponding IgM and IgG controls were measured by ELISA as follows. White opaque 96-well polystyrene ELISA plates were coated with 1 pg/mL of polymeric immunoglobulin receptor (mouse PIGR: R&D systems, Cat #2800-PG; human PIGR: Cat #2717-PG), human Fc alpha/mu receptor (R&D systems, Cat #9278-FC-050) or Human Fc mu receptor/Protein (Sino Biological, Cat #13556-H02H or R&D systems, Cat #9494-MU-050) in 100 μL PBS overnight at 4° C. Plates were then washed 5 times with 0.05% PBS-Tween and blocked with 2% BSA-PBS at room temperature for 2 hours. After blocking and 5 times of washing, 100 μL of serial diluted IgM or IgG proteins in 2% BSA-PBS were added to the wells and incubated at room temperature for 2 hours. The plates were then washed 5 times and incubated with HRP conjugated mouse anti-human kappa (SouthernBiotech, Cat #9230-05. 1:6000 diluted in 2% BSA-PBS) for 30 min. After the secondary incubation, the plates were washed 10 times before adding 100 μL of SuperSignal chemiluminescent substrate (ThermoFisher, Cat #37070) to each well. Luminescent signals were measured, and the data was plotted and analyzed with GraphPad Prism using a 4-parameter logistic model.

Binding of various mutant IgMs to the human and mouse receptors is summarized in FIG. 2. The T103A mutation in the J-chain inhibited human FcαμR binding but not human pIgR nor human FcμR binding (data not shown).

Bispecific anti-CD20/anti-CD3 antibodies with additional amino acid substitutions in the V15J modified J-chain at the amino acid position corresponding to Y102 of SEQ ID NO: 2 were also evaluated for their effect on binding to the pIgR receptor. The tyrosine at position 102 was substituted with aspartic acid (Y102D), phenylalanine (Y102F), arginine (Y102R), serine (Y102S), and threonine (Y102T). The mutations were incorporated into anti-CD20/anti-CD3 bispecific antibodies as described above. Except for the IgM comprising the Y102D mutation which exhibited reduced expression, the mutant IgMs all expressed and assembled as expected. The results of binding to pIgR are shown in FIGS. 3A-3E. The Y102F and Y102T mutations permitted binding to pIgR, whereas like the Y102A mutation, the Y102S and Y102R mutations disrupted pIgR binding.

Example 3: Pharmacokinetic Analysis of Anti-CD20 Antibodies Comprising Selected Mutations that Affect Receptor Binding This example demonstrates that certain amino acid substitutions in the J-chain or the IgM constant region of pentameric IgM monospecific or bispecific antibodies can increase the serum half-life of those antibodies. The J-chains and IgM constant regions of the monospecific anti-CD20 IgM antibody 1.5.3 as a monospecific pentamer (with the mature J-chain of SEQ ID NO: 2), and the bispecific anti-CD20 IgM antibody 1.5.3 IgM as a bispecific pentamer (with the "V15J" J-chain, SEQ ID NO: 9), both as described in PCT Publ. No. WO 2016/141303, were subjected to alanine-scanning mutagenesis and tested for alterations to pharmacokinetic parameters in mice. Mutants tested included J-chain alanine substitutions at positions corresponding to positions Y102 and T103 of the human mature J-chain of SEQ ID NO: 2 (Y102A and T103A). The modified "V15J" J-chain comprising the Y102A mutation is presented as SEQ ID NO: 10.

Pharmacokinetic parameters were measured for various IgM antibodies in an in vivo mouse model as follows. Balb/c mice were injected with 100 μg of each antibody via intravenous infusion. Approximately zero time and at each time point 500 μL of blood was collected by terminal cardiac puncture, with 3 mice per time point, and 8 or 15 time points total for each antibody. A standard ELISA assay was used to measure the serum concentration of each antibody in the blood at each time point. Quality metrics were verified on all ELISAs, and PK parameters, including $T_{1/2\text{-}alpha}$, $T_{1/2\text{-}beta}$, and the area under the concentration curve from time zero to infinity ($AUC_{0\text{-}\infty}$, measured in μg/ml*hr) were derived using standard curve fitting techniques (Win Non Lin, Phoenix Software). The PK results, including alpha and beta half-lives and AUC are presented in FIG. 4. The results show that the mutation corresponding to Y102 in the mature human J-chain SEQ ID NO: 2, as well as mutations corresponding to S401 and E401 in the human IgM constant region, either alone or in combination, could improve the PK parameters of the resulting IgM antibodies.

FIG. 5 shows compares the serum concentrations over time of certain of the bispecific mutant IgM antibodies compared to an IgG antibody comprising the same VH and VL regions. As shown by these results, the serum half-life of IgMs with a single Y102A mutation in the J-chain or with the Y102A mutation plus an additional mutation in the IgM heavy chain approach that of a comparable IgG antibody.

Example 4: Half-Life Extension of IgM Antibody Molecule Comprising N49A Variant Human J-Chain This example demonstrates that another single amino acid substitution in the human J-chain can increase the serum half-life of an IgM antibody comprising the variant J-chain. A previously described modified J-chain comprising a mature human J-chain with a heterologous antigen-binding domain that binds to CD3 fused to its N-terminus via a 15-amino acid linker ("V15J," SEQ ID NO: 9, see U.S. Pat. No. 9,951,134) was mutated using standard techniques to introducing an alanine substitution at the position corresponding to N49 of the wild-type mature human J-chain (SEQ ID NO: 2), to produce the modified J-chain "V15J-N49A" (SEQ ID NO: 24). SEQ ID NO: 24 is presented below.

SEQ ID NO: 24:

QVQLVQSGAEVKKPGASVKVSCKASGYTFISYTMHWV

RQAPGQGLEWMGYINPRSGYTHYNQKLKDKATLTADK

SASTAYMELSSLRSEDTAVYYCARSAYYDYDGFAYWG

QGTLVTVSSGGGGSGGGGSGGGGSDIQMTQSPSSLSASV

GDRVTITCSASSSVSYMNWYQQKPGKAPKRLIYDTSKL

ASGVPSRFSGSGSGTDFTLTISSLQPEDFATYYCQQWSSN

PPTFGGGTKLEIKGGGGSGGGGSGGGGSQEDERIVLVDN

KCKCARITSRIIRSSEDPNEDIVERNIRIIVPLNNREAISDPT

SPLRTRFVYHLSDLCKKCDPTEVELDNQIVTATQSNICD

EDSATETCYTYDRNKCYTAVVPLVYGGETKMVETALTP

DACYPD

This J-chain construct was used to produce 1.5.3 V15J and 1.5.3 V15J-N49A, exemplary pentameric IgM antibodies that bind to CD20. The CD20 antigen-binding domain and methods for making the IgM antibody were described in PCT Publ. No. WO/2016/141303. The antibodies were tested for proper assembly, antigen binding, and the ability of the CD3 binders to activate T-cells.

Pharmacokinetic (PK) studies were conducted in Balb/c mice as described in Example 3 to assess clearance of the IgM antibodies. Quality metrics were verified on all ELISAs, and PK parameters, including $T_{1/2\text{-}alpha}$, $T_{1/2\text{-}beta}$, and the area under the concentration curve from time zero to infinity ($AUC_{0\text{-}\infty}$, measured in μg/ml*hr) were derived using standard curve fitting techniques (Win Non Lin, Phoenix Software).

The results are shown in FIG. 6. As shown, IgM 1.5.3 V15J-N49A showed an increased $T_{1/2\text{-}alpha}$ by almost 50%, and the area under the concentration curve was 1.6 times higher.

The breadth and scope of the present disclosure should not be limited by any of the above-described exemplary embodiments but should be defined only in accordance with the following claims and their equivalents.

---

What is claimed is:

1. A polynucleotide encoding an IgM antibody with enhanced serum half-life comprising:
   a nucleic acid encoding an IgM heavy chain that comprises an IgM heavy chain constant region fused to a single chain Fv (scFv), a single domain variable region (VHH), or a heavy chain variable region (VH),
   a nucleic acid encoding an antibody light chain that comprises a human antibody light chain constant region fused to a light chain variable region (VL), and
   a nucleic acid encoding a variant J chain that comprises the amino acid sequence of SEQ ID NO: 2 except for: an alanine (A), serine(S), or arginine (R) substitution at amino acid Y102 of SEQ ID NO: 2, an alanine (A) substitution at amino acid T103 of SEQ ID NO: 2, an alanine (A) substitution at amino acid N49 of SEQ ID NO: 2, or a combination thereof;
   wherein the IgM antibody encoded by the polynucleotide exhibits an increased serum half-life upon administration to a subject animal relative to a reference IgM antibody that is identical except that the J chain comprises SEQ ID NO: 2, and wherein the IgM antibody and the reference IgM antibody are administered in the same way to the same animal species.

2. The polynucleotide of claim 1, wherein the IgM heavy chain constant region is a human IgM constant region comprising the amino acid sequence SEQ ID NO: 12.

3. The polynucleotide of claim 1, wherein the IgM heavy chain constant region is a variant human IgM constant region that is identical to a human IgM heavy chain constant region except for: an alanine (A) substitution at a position corresponding to amino acid S401 of SEQ ID NO: 12, an alanine (A) substitution at a position corresponding to amino acid E402 of SEQ ID NO: 12, or alanine (A) substitutions at positions corresponding to amino acids S401 and E402 of SEQ ID NO: 12.

4. The polynucleotide of claim 3, wherein the IgM heavy chain constant region comprises the amino acid sequence SEQ ID NO: 13 or SEQ ID NO: 14.

5. The polynucleotide of claim 1, wherein the variant J chain comprises the amino acid sequence of SEQ ID NO: 2 except for an alanine (A) substitution at amino acid Y102 of SEQ ID NO: 2.

6. The polynucleotide of claim 5, wherein the variant J chain comprises the amino acid sequence SEQ ID NO: 3.

7. The polynucleotide of claim 1, wherein the variant J chain comprises the amino acid sequence of SEQ ID NO: 2 except for a serine(S) substitution at amino acid Y102 of SEQ ID NO: 2.

8. The polynucleotide of claim 7, wherein the variant J chain comprises the amino acid sequence SEQ ID NO: 4.

9. The polynucleotide of claim 1, wherein the variant J chain comprises the amino acid sequence of SEQ ID NO: 2 except for an arginine (R) substitution at amino acid Y102 of SEQ ID NO: 2.

10. The polynucleotide of claim 9, wherein the variant J chain comprises the amino acid sequence SEQ ID NO: 5.

11. The polynucleotide of claim 1, wherein the variant J chain comprises the amino acid sequence of SEQ ID NO: 2 except for an alanine (A) substitution at amino acid T103 of SEQ ID NO: 2.

12. The polynucleotide of claim 11, wherein the variant J chain comprises the amino acid sequence SEQ ID NO: 6.

13. The polynucleotide of claim 1, wherein the variant J chain further comprises a heterologous polypeptide fused thereto.

14. An expression vector comprising the polynucleotide of claim 1.

15. A host cell comprising the polynucleotide of claim 1.

16. A method of producing an IgM antibody with enhanced serum half-life, comprising culturing the host cell of claim 15, and recovering the IgM antibody.

17. A polynucleotide encoding an IgM antibody with enhanced serum half-life comprising:

a nucleic acid encoding a variant IgM heavy chain that comprises an IgM heavy chain constant region fused to a single chain Fv (scFv), a single domain variable region (VHH), or a heavy chain variable region (VH), wherein the variant IgM heavy chain constant region is identical to a human IgM heavy chain constant region except for: an alanine (A) substitution at a position corresponding to amino acid S401 of SEQ ID NO: 12, an alanine (A) substitution at a position corresponding to amino acid E402 of SEQ ID NO: 12, or alanine (A) substitutions at positions corresponding to amino acids S401 and E402 of SEQ ID NO: 12; and a nucleic acid encoding an antibody light chain comprising a human antibody light chain constant region fused to a light chain variable region (VL);

wherein the IgM antibody encoded by the polynucleotide exhibits an increased serum half-life upon administration to a subject animal relative to a reference IgM antibody that is identical except that the IgM heavy chain constant region comprises SEQ ID NO: 12, and wherein the IgM antibody and the reference IgM antibody are administered in the same way to the same animal species.

18. The polynucleotide of claim 17, further comprising a nucleic acid encoding a J chain that comprises the amino acid sequence of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 10, SEQ ID NO: 23, or SEQ ID NO: 24.

19. The polynucleotide of claim 17, wherein the variant IgM heavy chain constant regions comprise an alanine (A) substitution at the position corresponding to amino acid S401 of SEQ ID NO: 12.

20. The polynucleotide of claim 19, wherein the variant IgM heavy chain constant region comprises the amino acid sequence SEQ ID NO: 13.

21. The polynucleotide of claim 17, wherein the variant IgM heavy chain constant regions comprise an alanine (A) substitution at the position corresponding to E402 of SEQ ID NO: 12.

22. The polynucleotide of claim 21, wherein the variant IgM heavy chain constant region comprises the amino acid sequence SEQ ID NO: 14.

23. The polynucleotide of claim 17, wherein the J chain further comprises a heterologous polypeptide fused thereto.

24. An expression vector comprising the polynucleotide of claim 17.

25. A host cell comprising the polynucleotide of claim 17.

26. A method of producing an IgM antibody with enhanced serum half-life, comprising culturing the host cell of claim 25, and recovering the IgM antibody.

* * * * *

SEQUENCE LISTING

```
Sequence total quantity: 34
SEQ ID NO: 1              moltype = AA  length = 159
FEATURE                  Location/Qualifiers
source                   1..159
                         mol_type = protein
                         organism = Homo sapiens
SEQUENCE: 1
MKNHLLFWGV LAVFIKAVHV KAQEDERIVL VDNKCKCARI TSRIIRSSED PNEDIVERNI   60
RIIVPLNNRE NISDPTSPLR TRFVYHLSDL CKKCDPTEVE LDNQIVTATQ SNICDEDSAT  120
ETCYTYDRNK CYTAVVPLVY GGETKMVETA LTPDACYPD                         159

SEQ ID NO: 2              moltype = AA  length = 137
FEATURE                  Location/Qualifiers
source                   1..137
                         mol_type = protein
                         organism = Homo sapiens
SEQUENCE: 2
QEDERIVLVD NKCKCARITS RIIRSSEDPN EDIVERNIRI IVPLNNRENI SDPTSPLRTR   60
FVYHLSDLCK KCDPTEVELD NQIVTATQSN ICDEDSATET CYTYDRNKCY TAVVPLVYGG  120
ETKMVETALT PDACYPD                                                 137

SEQ ID NO: 3              moltype = AA  length = 137
FEATURE                  Location/Qualifiers
REGION                   1..137
                         note = Description of Artificial Sequence: Synthetic
                         polypeptide
source                   1..137
                         mol_type = protein
                         organism = synthetic construct
SEQUENCE: 3
QEDERIVLVD NKCKCARITS RIIRSSEDPN EDIVERNIRI IVPLNNRENI SDPTSPLRTR   60
FVYHLSDLCK KCDPTEVELD NQIVTATQSN ICDEDSATET CATYDRNKCY TAVVPLVYGG  120
ETKMVETALT PDACYPD                                                 137

SEQ ID NO: 4              moltype = AA  length = 137
FEATURE                  Location/Qualifiers
REGION                   1..137
                         note = Description of Artificial Sequence: Synthetic
                         polypeptide
source                   1..137
                         mol_type = protein
                         organism = synthetic construct
SEQUENCE: 4
QEDERIVLVD NKCKCARITS RIIRSSEDPN EDIVERNIRI IVPLNNRENI SDPTSPLRTR   60
FVYHLSDLCK KCDPTEVELD NQIVTATQSN ICDEDSATET CSTYDRNKCY TAVVPLVYGG  120
ETKMVETALT PDACYPD                                                 137

SEQ ID NO: 5              moltype = AA  length = 137
FEATURE                  Location/Qualifiers
```

```
REGION                   1..137
                         note = Description of Artificial Sequence: Synthetic
                          polypeptide
source                   1..137
                         mol_type = protein
                         organism = synthetic construct
SEQUENCE: 5
QEDERIVLVD NKCKCARITS RIIRSSEDPN EDIVERNIRI IVPLNNRENI SDPTSPLRTR   60
FVYHLSDLCK KCDPTEVELD NQIVTATQSN ICDEDSATET CRTYDRNKCY TAVVPLVYGG  120
ETKMVETALT PDACYPD                                                137

SEQ ID NO: 6             moltype = AA  length = 137
FEATURE                  Location/Qualifiers
REGION                   1..137
                         note = Description of Artificial Sequence: Synthetic
                          polypeptide
source                   1..137
                         mol_type = protein
                         organism = synthetic construct
SEQUENCE: 6
QEDERIVLVD NKCKCARITS RIIRSSEDPN EDIVERNIRI IVPLNNRENI SDPTSPLRTR   60
FVYHLSDLCK KCDPTEVELD NQIVTATQSN ICDEDSATET CYAYDRNKCY TAVVPLVYGG  120
ETKMVETALT PDACYPD                                                137

SEQ ID NO: 7             moltype = AA  length = 137
FEATURE                  Location/Qualifiers
REGION                   1..137
                         note = Description of Artificial Sequence: Synthetic
                          polypeptide
source                   1..137
                         mol_type = protein
                         organism = synthetic construct
SEQUENCE: 7
QEDERIVLVD NKCKCARITS RIIRSSEDPN EDIVERNIRI IVPLNNREAI SDPTSPLRTR   60
FVYHLSDLCK KCDPTEVELD NQIVTATQSN ICDEDSATET CYTYDRNKCY TAVVPLVYGG  120
ETKMVETALT PDACYPD                                                137

SEQ ID NO: 8             moltype = AA  length = 137
FEATURE                  Location/Qualifiers
REGION                   1..137
                         note = Description of Artificial Sequence: Synthetic
                          polypeptide
source                   1..137
                         mol_type = protein
                         organism = synthetic construct
SEQUENCE: 8
QEDERIVLVD NKCKCARITS RIIRSSEDPN EDIVERNIRI IVPLNNRENI ADPTSPLRTR   60
FVYHLSDLCK KCDPTEVELD NQIVTATQSN ICDEDSATET CYTYDRNKCY TAVVPLVYGG  120
ETKMVETALT PDACYPD                                                137

SEQ ID NO: 9             moltype = AA  length = 393
FEATURE                  Location/Qualifiers
REGION                   1..393
                         note = Description of Artificial Sequence: Synthetic
                          polypeptide
source                   1..393
                         mol_type = protein
                         organism = synthetic construct
SEQUENCE: 9
QVQLVQSGAE VKKPGASVKV SCKASGYTFI SYTMHWVRQA PGQGLEWMGY INPRSGYTHY   60
NQKLKDKATL TADKSASTAY MELSSLRSED TAVYYCARSA YYDYDGFAYW GQGTLVTVSS  120
GGGGSGGGGS GGGGSDIQMT QSPSSLSASV GDRVTITCSA SSSVSYMNWY QQKPGKAPKR  180
LIYDTSKLAS GVPSRFSGSG SGTDFTLTIS SLQPEDFATY YCQQWSSNPP TFGGGTKLEI  240
KGGGGSGGGG SGGGGSQEDE RIVLVDNKCK CARITSRIIR SSEDPNEDIV ERNIRIIVPL  300
NNRENISDPT SPLRTRFVYH LSDLCKKCDP TEVELDNQIV TATQSNICDE DSATETCYTY  360
DRNKCYTAVV PLVYGGETKM VETALTPDAC YPD                              393

SEQ ID NO: 10            moltype = AA  length = 393
FEATURE                  Location/Qualifiers
REGION                   1..393
                         note = Description of Artificial Sequence: Synthetic
                          polypeptide
source                   1..393
                         mol_type = protein
                         organism = synthetic construct
SEQUENCE: 10
QVQLVQSGAE VKKPGASVKV SCKASGYTFI SYTMHWVRQA PGQGLEWMGY INPRSGYTHY   60
NQKLKDKATL TADKSASTAY MELSSLRSED TAVYYCARSA YYDYDGFAYW GQGTLVTVSS  120
GGGGSGGGGS GGGGSDIQMT QSPSSLSASV GDRVTITCSA SSSVSYMNWY QQKPGKAPKR  180
```

```
LIYDTSKLAS GVPSRFSGSG SGTDFTLTIS SLQPEDFATY YCQQWSSNPP TFGGGTKLEI  240
KGGGGSGGGG SGGGGSQEDE RIVLVDNKCK CARITSRIIR SSEDPNEDIV ERNIRIIVPL  300
NNRENISDPT SPLRTRFVYH LSDLCKKCDP TEVELDNQIV TATQSNICDE DSATETCATY  360
DRNKCYTAVV PLVYGGETKM VETALTPDAC YPD                                393

SEQ ID NO: 11              moltype = AA  length = 1012
FEATURE                    Location/Qualifiers
REGION                     1..1012
                           note = Description of Artificial Sequence: Synthetic
                            polypeptide
source                     1..1012
                           mol_type = protein
                           organism = synthetic construct
SEQUENCE: 11
MGWSYIILFL VATATGVHSQ VQLVQSGAEV KKPGASVKVS CKASGYTFIS YTMHWVRQAP  60
GQGLEWMGYI NPRSGYTHYN QKLKDKATLT ADKSASTAYM ELSSLRSEDT AVYYCARSAY  120
YDYDGFAYWG QGTLVTVSSG GGGSGGGGSG GGGSDIQMTQ SPSSLSASVG DRVTITCSAS  180
SSVSYMNWYQ QKPGKAPKRL IYDTSKLASG VPSRFSGSGS GTDFTLTISS LQPEDFATYY  240
CQQWSSNPPT FGGGTKVEIK GGGGSGGGGS GGGGSQEDER IVLVDNKCKC ARITSRIIRS  300
SEDPNEDIVE RNIRIIVPLN NRENISDPTS PLRTRFVYHL SDLCKKCDPT EVELDNQIVT  360
ATQSNICDED SATETCYTYD RNKCYTAVVP LVYGGETKMV ETALTPDACY PDGGGGSGGG  420
GSGGGGSDAH KSEVAHRFKD LGEENFKALV LIAFAQYLQQ CPFEDHVKLV NEVTEFAKTC  480
VADESAENCD KSLHTLFGDK LCTVATLRET YGEMADCCAK QEPERNECFL QHKDDNPNLP  540
RLVRPEVDVM CTAFHDNEET FLKKYLYEIA RRHPYFYAPE LLFFAKRYKA AFTECCQAAD  600
KAACLLPKLD ELRDEGKASS AKQRLKCASL QKFGERAFKA WAVARLSQRF PKAEFAEVSK  660
LVTDLTKVHT ECCHGDLLEC ADDRADLAKY ICENQDSISS KLKECCEKPL LEKSHCIAEV  720
ENDEMPADLP SLAADFVESK DVCKNYAEAK DVFLGMFLYE YARRHPDYSV VLLLRLAKTY  780
ETTLEKCCAA ADPHECYAKV FDEFKPLVEE PQNLIKQNCE LFKQLGEYKF QNALLVRYTK  840
KVPQVSTPTL VEVSRNLGKV GSKCCKHPEA KRMPCAEDYL SVVLNQLCVL HEKTPVSDRV  900
TKCCTESLVN RRPCFSALEV DETYVPKEFN AETFTFHADI CTLSEKERQI KKQTALVELV  960
KHKPKATKEQ LKAVMDDFAA FVEKCCKADD KETCFAEEGK KLVAASQAAL GL           1012

SEQ ID NO: 12              moltype = AA  length = 453
FEATURE                    Location/Qualifiers
source                     1..453
                           mol_type = protein
                           organism = Homo sapiens
SEQUENCE: 12
GSASAPTLFP LVSCENSPSD TSSVAVGCLA QDFLPDSITF SWKYKNNSDI SSTRGFPSVL  60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL SQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
FTCTVTHTDL PSPLKQTISR PKGVALHRPD VYLLPPAREQ LNLRESATIT CLVTGFSPAD  360
VFVQWMQRGQ PLSPEKYVTS APMPEPQAPG RYFAHSILTV SEEEWNTGET YTCVVAHEAL  420
PNRVTERTVD KSTGKPTLYN VSLVMSDTAG TCY                                453

SEQ ID NO: 13              moltype = AA  length = 453
FEATURE                    Location/Qualifiers
REGION                     1..453
                           note = Description of Artificial Sequence: Synthetic
                            polypeptide
source                     1..453
                           mol_type = protein
                           organism = synthetic construct
SEQUENCE: 13
GSASAPTLFP LVSCENSPSD TSSVAVGCLA QDFLPDSITF SWKYKNNSDI SSTRGFPSVL  60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL SQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
FTCTVTHTDL PSPLKQTISR PKGVALHRPD VYLLPPAREQ LNLRESATIT CLVTGFSPAD  360
VFVQWMQRGQ PLSPEKYVTS APMPEPQAPG RYFAHSILTV AEEEWNTGET YTCVVAHEAL  420
PNRVTERTVD KSTGKPTLYN VSLVMSDTAG TCY                                453

SEQ ID NO: 14              moltype = AA  length = 453
FEATURE                    Location/Qualifiers
REGION                     1..453
                           note = Description of Artificial Sequence: Synthetic
                            polypeptide
source                     1..453
                           mol_type = protein
                           organism = synthetic construct
SEQUENCE: 14
GSASAPTLFP LVSCENSPSD TSSVAVGCLA QDFLPDSITF SWKYKNNSDI SSTRGFPSVL  60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL SQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
```

-continued

```
FTCTVTHTDL PSPLKQTISR PKGVALHRPD VYLLPPAREQ LNLRESATIT CLVTGFSPAD  360
VFVQWMQRGQ PLSPEKYVTS APMPEPQAPG RYFAHSILTV SAEEWNTGET YTCVVAHEAL  420
PNRVTERTVD KSTGKPTLYN VSLVMSDTAG TCY                                453

SEQ ID NO: 15            moltype = AA   length = 453
FEATURE                  Location/Qualifiers
REGION                   1..453
                         note = Description of Artificial Sequence: Synthetic
                          polypeptide
source                   1..453
                         mol_type = protein
                         organism = synthetic construct
SEQUENCE: 15
GSASAPTLFP LVSCENSPSD TSSVAVGCLA QDFLPDSITF SWKYKNNSDI SSTRGFPSVL  60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL SQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
FTCTVTHTDL ASSLKQTISR PKGVALHRPD VYLLPPAREQ LNLRESATIT CLVTGFSPAD  360
VFVQWMQRGQ PLSPEKYVTS APMPEPQAPG RYFAHSILTV SEEEWNTGET YTCVVAHEAL  420
PNRVTERTVD KSTGKPTLYN VSLVMSDTAG TCY                                453

SEQ ID NO: 16            moltype = AA   length = 455
FEATURE                  Location/Qualifiers
source                   1..455
                         mol_type = protein
                         organism = Mus musculus
SEQUENCE: 16
ASQSFPNVFP LVSCESPLSD KNLVAMGCLA RDFLPSTISF TWNYQNNTEV IQGIRTFPTL  60
RTGGKYLATS QVLLSPKSIL EGSDEYLVCK IHYGGKNRDL HVPIPAVAEM NPNVNVFVPP  120
RDGFSGPAPR KSKLICEATN FTPKPITVSW LKDGKLVESG FTTDPVTIEN KGSTPQTYKV  180
ISTLTISEID WLNLNVYTCR VDHRGLTFLK NVSSTCAASP STDILNFTIP PSFADIFLSK  240
SANLTCLVSN LATYETLSIS WASQSGEPLE TKIKIMESHP NGTFSAKGVA SVCVEDWNNR  300
KEFVCTVTHR DLPSPQKKFI SKPNEVHKHP PAVYLLPPAR EQLNLRESAT VTCLVKGFSP  360
ADISVQWKQR GQLLPQEKYV TSAPMPEPGA PGFYFTHSIL TVTEEEWNSG ETYTCVVGHE  420
ALPHLVTERT VDKSTGKPTL YNVSLIMSDT GGTCY                              455

SEQ ID NO: 17            moltype = AA   length = 472
FEATURE                  Location/Qualifiers
source                   1..472
                         mol_type = protein
                         organism = Macaca mulatta
SEQUENCE: 17
GSASAPTLFP LVSCENAPLD TNEVAVGCLA QDFLPDSITF SWKFKNNSNI SKGVWGFPSV  60
LRGGKYAATS QVLLASKDVM QGTDEHVVCK VQHPNGNKEQ NVPLPVLAER PPNVSVFVPP  120
RDGFVGNPRE SKLICQATGF SPRQIEVSWL REGKQVGSGI TTDRVEAEAK ESGPTTFKVT  180
STLTVSERDW LSQSVFTCRV DHRGLTFQKN VSSVCGPNPD TAIRVFAIPP SFASIFLTKS  240
TKLTCLVTDL ATYDSVTITW TRQNGEALKT HTNISESHPN GTFSAVGEAS ICEDDWNSGE  300
RFRCTVTHTD LPSPLKQTIS RPKGVAMHRP DVYLLPPARE QLNLRESATI TCLVTGFSPA  360
DIFVQWMQRG QPLSPEKYVT SAPMPEPQAP GRYFAHSILT VSEEDWNTGE TYTCVVAHEA  420
LPNRVTERTV DKSTEGEVSA DEEGFENLWA TASTFIVLFL LSLFYSTTVT LF           472

SEQ ID NO: 18            moltype = AA   length = 488
FEATURE                  Location/Qualifiers
source                   1..488
                         mol_type = protein
                         organism = Pan troglodytes
SEQUENCE: 18
TTVTVSSGSA SAPTLFPLVS CENSPSDTSS VAVGCLAQDF LPDSITFSWK YKNNSDISST  60
RGFPSVLRGG KYAATSQVLL PSKEVMQGTD EHVVCKVQHP NGNKEKNVPL PVTAELPPKV  120
SIFVPPRDGF FGNPRSSKLI CQATGFSPRQ IQVSWLREGK QVGSGVTTDQ VQAEAKQSGP  180
TTYKVTSTLT IKESDWLSQS VFTCRVDHRG LTFQQNASSM CSPGESRHSS PGLCHPPSFA  240
SIFLTKSTKL ACLVTDLTTY DSLTISWTRQ NGEAVKTHTN ISESHPNATF SAVGEASICE  300
DDWNSGERFT CTVTHTDLPS PLKQTISRPK EVALHRPDVY LLPPAREQLN LRELATITCL  360
VTGFSPADVF VQWMQRGQPL SPEKYVTSAP MPEPQAPGRY FAHSILTVSE EEWNTGETYT  420
CVVAHEALPN RVTERTVDKS TGKTHPVQRV PGHVRHSWHL LLTLLACPQA QGGRPLCVCA  480
CKLTVSTG                                                            488

SEQ ID NO: 19            moltype = AA   length = 453
FEATURE                  Location/Qualifiers
source                   1..453
                         mol_type = protein
                         organism = Pongo abelii
SEQUENCE: 19
GSASAPTLFP LVSCENSLSD TSSVAVGCLA QDFLPDSITF SWKYKNNSDI SSTRGFPSVL  60
TGSKYVATSQ VLLPSKDVMQ GTDEHVVCKV QHPNGNKEKN VPLPVIAELP PKVSIFIPPR  120
DGFFGSPRKS KLICQATGFS PRQIQVSWLR EGKQVASGIT TDQVQAEAKE SGPTTYKVTS  180
TLTINESDWL SQSMFTCRVD HRGLTFQKNA SSMCSPNPNT AIRVFAIPPS FASIFLTKST  240
KLTCLVTDLA SYDSMTISWT RQNGEAVKTH TNISESHPNA TFSAVGEASI CEDDWNSGER  300
```

-continued

```
FTCTVTHADL PSPLKQTISR PKGVALHRPD VYLLPPAREQ LNLRESATIT CLVTGFSPAD   360
VFVQWMQRGQ PLSPEKYVTS APMPEPQAPG RYFAHSILTV SEEDWNTGET YTCVVAHEAL   420
PNRVTERTVD KSTGKPTLYN VSLVMSDTAG TCY                                453

SEQ ID NO: 20            moltype = AA  length = 764
FEATURE                  Location/Qualifiers
source                   1..764
                         mol_type = protein
                         organism = Homo sapiens
SEQUENCE: 20
MLLFVLTCLL AVFPAISTKS PIFGPEEVNS VEGNSVSITC YYPPTSVNRH TRKYWCRQGA   60
RGGCITLISS EGYVSSKYAG RANLTNFPEN GTFVVNIAQL SQDDSGRYKC GLGINSRGLS   120
FDVSLEVSQG PGLLNDTKVY TVDLGRTVTI NCPFKTENAQ KRKSLYKQIG LYPVLVIDSS   180
GYVNPNYTGR IRLDIQGTGQ LLFSVVINQL RLSDAGQYLC QAGDDSNSNK KNADLQVLKP   240
EPELVYEDLR GSVTFHCALG PEVANVAKFL CRQSSGENCD VVVNTLGKRA PAFEGRILLN   300
PQDKDGSFSV VITGLRKEDA GRYLCGAHSD GQLQEGSPIQ AWQLFVNEES TIPRSPTVVK   360
GVAGSSVAVL CPYNRKESKS IKYWCLWEGA QNGRCPLLVD SEGWVKAQYE GRLSLLEEPG   420
NGTFTVILNQ LTSRDAGFYW CLTNGDTLWR TTVEIKIIEG EPNLKVPGNV TAVLGETLKV   480
PCHFPCKFSS YEKYWCKWNN TGCQALPSQD EGPSKAFVNC DENSRLVSLT LNLVTRADEG   540
WYWCGVKQGH FYGETAAVYV AVEERKAAGS RDVSLAKADA APDEKVLDSG FREIENKAIQ   600
DPRLFAEEKA VADTRDQADG SRASVDSGSS EEQGGSSRAL VSTLVPLGLV LAVGAVAVGV   660
ARARHRKNVD RVSIRSYRTD ISMSDFENSR EFGANDNMGA SSITQETSLG GKEEFVATTE   720
STTETKEPKK AKRSSKEEAE MAYKDFLLQS STVAAEAQDG PQEA                    764

SEQ ID NO: 21            moltype = AA  length = 390
FEATURE                  Location/Qualifiers
source                   1..390
                         mol_type = protein
                         organism = Homo sapiens
SEQUENCE: 21
MDFWLWPLYF LPVSGALRIL PEVKVEGELG GSVTIKCPLP EMHVRIYLCR EMAGSGTCGT   60
VVSTTNFIKA EYKGRVTLKQ YPRKNLFLVE VTQLTESDSG VYACGAGMNT DRGKTQKVTL   120
NVHSEYEPSW EEQPMPETPK WFHLPYLFQM PAYASSSKFV TRVTTPAQRG KVPPVHHSSP   180
TTQITHRPRV SRASSVAGDK PRTFLPSTTA SKISALEGLL KPQTPSYNHH TRLHRQRALD   240
YGSQSGREGQ GFHILIPTIL GLFLLALLGL VVKRAVERRK ALSRRARRLA VRMRALESSQ   300
RPRGSPRPRS QNNIYSACPR RARGADAAGT GEAPVPGPGA PLPPAPLQVS ESPWLHAPSL   360
KTSCEYVSLY HQPAAMMEDS DSDDYINVPA                                    390

SEQ ID NO: 22            moltype = AA  length = 532
FEATURE                  Location/Qualifiers
source                   1..532
                         mol_type = protein
                         organism = Homo sapiens
SEQUENCE: 22
MPLFLILCLL QGSSFALPQK RPHPRWLWEG SLPSRTHLRA MGTLRPSSPL CWREESSFAA   60
PNSLKGSRLV SGEPGGAVTI QCHYAPSSVN RHQRKYWCRL GPPRWICQTI VSTNQYTHHR   120
YRDRVALTDF PQRGLFVVRL SQLSPDDIGC YLCGIGSENN MLFLSMNLTI SAGPASTLPT   180
ATPAAGELTM RSYGTASPVA NRWTPGTTQT LGQGTAWDTV ASTPGTSKTT ASAEGRRTPG   240
ATRPAAPGTG SWAEGSVKAP APIPESPPSK SRSMSNTTEG VWEGTRSSVT NRARASKDRR   300
EMTTTKADRP REDIEGVRIA LDAAKKVLGT IGPPALVSET LAWEILPQAT PVSKQQSQGS   360
IGETTPAAGM WTLGTPAADV WILGTPAADV WTSMEAASGE GSAAGDLDAA TGDRGPQATL   420
SQTPAVGPWG PPGKESSVKR TFPEDESSSR TLAPVSTMLA LFMLMALVLL QRKLWRRRTS   480
QEAERVTLIQ MTHFLEVNPQ ADQLPHVERK MLQDDSLPAG ASLTAPERNP GP           532

SEQ ID NO: 23            moltype = AA  length = 393
FEATURE                  Location/Qualifiers
REGION                   1..393
                         note = Description of Artificial Sequence: Synthetic
                         polypeptide
source                   1..393
                         mol_type = protein
                         organism = synthetic construct
SEQUENCE: 23
QVQLVQSGAE VKKPGASVKV SCKASGYTFI SYTMHWVRQA PGQGLEWMGY INPRSGYTHY   60
NQKLKDKATL TADKSASTAY MELSSLRSED TAVYYCARSA YYDYDGFAYW GQGTLVTVSS   120
GGGGSGGGGS GGGGSDIQMT QSPSSLSASV GDRVTITCSA SSSVSYMNWY QQKPGKAPKR   180
LIYDTSKLAS GVPSRFSGSG SGTDFTLTIS SLQPEDFATY YCQQWSSNPP TFGGGTKLEI   240
KGGGGSGGGG SGGGGSQEDE RIVLVDNKCK CARITSRIIR SSEDPNEDIV ERNIRIIVPL   300
NNRENISDPT SPLRTRFVYH LSDLCKKCDP TEVELDNQIV TATQSNICDE DSATETCYAY   360
DRNKCYTAVV PLVYGGETKM VETALTPDAC YPD                                393

SEQ ID NO: 24            moltype = AA  length = 393
FEATURE                  Location/Qualifiers
REGION                   1..393
                         note = Description of Artificial Sequence: Synthetic
                         polypeptide
source                   1..393
                         mol_type = protein
                         organism = synthetic construct
```

```
SEQUENCE: 24
QVQLVQSGAE VKKPGASVKV SCKASGYTFI SYTMHWVRQA PGQGLEWMGY INPRSGYTHY 60
NQKLKDKATL TADKSASTAY MELSSLRSED TAVYYCARSA YYDYDGFAYW GQGTLVTVSS 120
GGGGSGGGGS GGGGSDIQMT QSPSSLSASV GDRVTITCSA SSSVSYMNWY QQKPGKAPKR 180
LIYDTSKLAS GVPSRFSGSG SGTDFTLTIS SLQPEDFATY YCQQWSSNPP TFGGGTKLEI 240
KGGGGSGGGG SGGGGSQEDE RIVLVDNKCK CARITSRIIR SSEDPNEDIV ERNIRIIVPL 300
NNREAISDPT SPLRTRFVYH LSDLCKKCDP TEVELDNQIV TATQSNICDE DSATETCYTY 360
DRNKCYTAVV PLVYGGETKM VETALTPDAC YPD 393

SEQ ID NO: 25          moltype = AA   length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 25
GGGGS                                                           5

SEQ ID NO: 26          moltype = AA   length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 26
GGGGSGGGGS                                                     10

SEQ ID NO: 27          moltype = AA   length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 27
GGGGSGGGGS GGGGS                                              15

SEQ ID NO: 28          moltype = AA   length = 20
FEATURE                Location/Qualifiers
REGION                 1..20
                       note = Description of Artificial Sequence: Synthetic peptide
source                 1..20
                       mol_type = protein
                       organism = synthetic construct
SEQUENCE: 28
GGGGSGGGGS GGGGSGGGGS                                         20

SEQ ID NO: 29          moltype = AA   length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 29
GGGGSGGGGS GGGGSGGGGS GGGGS                                   25

SEQ ID NO: 30          moltype = AA   length = 487
FEATURE                Location/Qualifiers
source                 1..487
                       mol_type = protein
                       organism = Macaca fascicularis
SEQUENCE: 30
FWGQGALVTV SSGESAGPFK WEPSVSSPNA PLDTNEVAVG CLAQDFLPDS ITFSWKFKNN 60
SDISKGVWGF PSVLRGGKYA ATSQVLLASK DVMQGTDEHV VCKVQHPNGN KEQNVPLPVV 120
AERPPNVSVF VPPRDGFVGN PRESKLICQA TGFSPRQIEV SWLRDGKQVG SGITTDRVEA 180
EAKESGPTTF KVTSTLTVSE RDWLSQSVFT CRVDHRGLTF QKNVSSVCGP NPDTAIRVFA 240
IPPSFASIFL TKSTKLTCLV TDLATYDSVT ITWTRQNGEA LKTHTNISES HPNGTFSAVG 300
EASICEDDWN SGERFRCTVT HTDLPSPLKQ TISRPKGVAM HRPDVYLLPP AREQLNLRES 360
ATITCLVTGF SPADIFVQWM QRGQPLSPEK YVTSAPMPEP QAPGRYFAHS ILTVSEEDWN 420
TGETYTCVVA HEALPNRVTE RTVDKSTGKP TLYNVSLVIL WTTLSTFVAL FVLTLLYSGI 480
VTFIKVR 487

SEQ ID NO: 31          moltype = AA   length = 453
FEATURE                Location/Qualifiers
```

-continued

```
REGION                  1..453
                        note = Description of Artificial Sequence: Synthetic
                         polypeptide
source                  1..453
                        mol_type = protein
                        organism = synthetic construct
SEQUENCE: 31
GSASAPTLFP LVSCENSPSD TSSVAVGCLA QDFLPDSITF SWKYKNNSDI SSTRGFPSVL  60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL SQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
FTCTVTHTDL PSPLKQTISR PKGVALHRPD VYLLPPAREQ LNLAESATIT CLVTGFSPAD  360
VFVQWMQRGQ PLSPEKYVTS APMPEPQAPG RYFAHSILTV SEEEWNTGET YTCVVAHEAL  420
PNRVTERTVD KSTGKPTLYN VSLVMSDTAG TCY                                453

SEQ ID NO: 32           moltype = AA  length = 453
FEATURE                 Location/Qualifiers
REGION                  1..453
                        note = Description of Artificial Sequence: Synthetic
                         polypeptide
source                  1..453
                        mol_type = protein
                        organism = synthetic construct
SEQUENCE: 32
GSASAPTLFP LVSCENSPSD TSSVAVGCLA QDFLPDSITF SWKYKNNSDI SSTRGFPSVL  60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL SQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
FTCTVTHTDL PSPLKQTISR PKGVALHRPD VYLLPPAREQ LNLRASATIT CLVTGFSPAD  360
VFVQWMQRGQ PLSPEKYVTS APMPEPQAPG RYFAHSILTV SEEEWNTGET YTCVVAHEAL  420
PNRVTERTVD KSTGKPTLYN VSLVMSDTAG TCY                                453

SEQ ID NO: 33           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 33
GSGSGSG                                                             7

SEQ ID NO: 34           moltype = AA  length = 453
FEATURE                 Location/Qualifiers
REGION                  1..453
                        note = Description of Artificial Sequence: Synthetic
                         polypeptide
source                  1..453
                        mol_type = protein
                        organism = synthetic construct
SEQUENCE: 34
GSASAPTLFP LVSCENSPSD TSSVAVGCLA QDFLPDSITF SWKYKNNSDI SSTRGFPSVL  60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL SQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
FTCTVTHTDL PSPLKQTISR PKGVALHRPD VYLLPPAREQ LNLRESATIT CLVTGFSPAD  360
VFVQWMQRGQ PLSPEKYVTS APMPEPQAPG RYFAHSILTV SEAEWNTGET YTCVVAHEAL  420
PNRVTERTVD KSTGKPTLYN VSLVMSDTAG TCY                                453
```